United States Patent
Yabe et al.

(10) Patent No.: US 8,324,403 B2
(45) Date of Patent: Dec. 4, 2012

(54) ORGANIC COMPOUND, CHARGE-TRANSPORTING MATERIAL, AND ORGANIC ELECTROLUMINESCENT ELEMENT

(75) Inventors: Masayoshi Yabe, Yokohama (JP); Hideki Sato, Yokohama (JP)

(73) Assignees: Pioneer Corporation, Tokyo (JP); Mitsubishi Chemical Corporation, Tokyo (JP)

( * ) Notice: Subject to any disclaimer, the term of this patent is extended or adjusted under 35 U.S.C. 154(b) by 1180 days.

(21) Appl. No.: 11/722,760

(22) PCT Filed: Dec. 9, 2005

(86) PCT No.: PCT/JP2005/022635
§ 371 (c)(1),
(2), (4) Date: Jun. 25, 2007

(87) PCT Pub. No.: WO2006/067976
PCT Pub. Date: Jun. 29, 2006

(65) Prior Publication Data
US 2008/0145699 A1   Jun. 19, 2008
US 2009/0191426 A2   Jul. 30, 2009

(51) Int. Cl.
*C07D 401/00* (2006.01)
*C07D 401/02* (2006.01)
*C07D 403/00* (2006.01)
*C09K 11/06* (2006.01)

(52) U.S. Cl. ............ 548/440; 546/276.7; 544/180; 544/242; 544/336; 540/1

(58) Field of Classification Search ............ 428/690
See application file for complete search history.

(56) References Cited

U.S. PATENT DOCUMENTS
6,660,410 B2   12/2003   Hosokawa
(Continued)

FOREIGN PATENT DOCUMENTS
EP   0 517 542   12/1992
(Continued)

OTHER PUBLICATIONS
Zhang, Q.; Chen, J.; Cheng, Y.; Wang, L.; Ma, D.; Jing, X.; Wang, F. J. Mater. Chem., 2004, 14, 895-900.*
(Continued)

*Primary Examiner* — Marie R. Yamnitzky
*Assistant Examiner* — J. L. Yang
(74) *Attorney, Agent, or Firm* — Oblon, Spivak, McClelland, Maier & Neustadt, L.L.P.

(57) ABSTRACT

There are provided an organic having both excellent hole transporting property and satisfactory electron transporting and showing excellent durability against electric oxidation/reduction and a high triplet excitation level, and a charge transporting material and an organic electroluminescent device each using the organic compound. The organic compound is represented by following Formula (I):

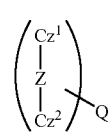

(I)

wherein $Cz^1$ and $Cz^2$ each represent a carbazolyl group; Z represents a direct bond or an arbitrary linkage group enabling the conjugation of nitrogen atoms in the carbazole rings of $Cz^1$ and $Cz^2$ with each other; and Q represents a direct bond connecting to "G" in following Formula (II):

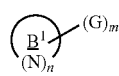

(II)

13 Claims, 2 Drawing Sheets

U.S. PATENT DOCUMENTS

| | | | |
|---|---|---|---|
| 2003/0205696 A1 | 11/2003 | Thoms et al. | |
| 2004/0086745 A1* | 5/2004 | Iwakuma et al. | 428/690 |
| 2004/0137263 A1* | 7/2004 | Burn et al. | 428/690 |
| 2004/0212042 A1* | 10/2004 | Sagisaka et al. | 257/552 |
| 2004/0247933 A1 | 12/2004 | Thoms | |
| 2005/0127823 A1 | 6/2005 | Iwakuma et al. | |
| 2005/0249976 A1 | 11/2005 | Iwakuma et al. | |
| 2006/0180806 A1* | 8/2006 | Arakane et al. | 257/40 |
| 2006/0257684 A1 | 11/2006 | Arakane et al. | |
| 2007/0104976 A1 | 5/2007 | Iwakuma et al. | |
| 2007/0159083 A1 | 7/2007 | Matsuura et al. | |
| 2007/0172698 A1 | 7/2007 | Iwakuma et al. | |

FOREIGN PATENT DOCUMENTS

| | | |
|---|---|---|
| EP | 1 205 527 A1 | 5/2002 |
| EP | 1 486 550 A1 | 12/2004 |
| EP | 1 489 155 | 12/2004 |
| EP | 1 551 206 | 7/2005 |
| EP | 1 672 961 A1 | 6/2006 |
| EP | 1 718 121 | 11/2006 |
| EP | 1 724 323 | 11/2006 |
| EP | 1 857 521 A1 | 11/2007 |
| EP | 1 885 008 A1 | 2/2008 |
| EP | 1 887 640 A1 | 2/2008 |
| JP | 6 1972 | 1/1994 |
| JP | 2000 169448 | 6/2000 |
| JP | 2000-169448 | 6/2000 |
| JP | 2000169448 A * | 6/2000 |
| JP | 2000-186066 | 7/2000 |
| JP | 2000 186066 | 7/2000 |
| JP | 2002-8860 | 1/2002 |
| JP | 2003-022893 | 1/2003 |
| JP | 2003 22893 | 1/2003 |
| JP | 2003-317966 | 11/2003 |
| JP | 2004-171808 | 6/2004 |
| JP | 2004-217557 | 8/2004 |
| JP | 2004-311404 | 11/2004 |
| JP | 2005-268199 | 9/2005 |
| TW | 200304937 A | 10/2003 |
| TW | 200417279 A | 9/2004 |
| TW | 200524464 A | 7/2005 |
| TW | 200533239 A | 10/2005 |
| TW | 200541401 A | 12/2005 |
| WO | WO 01/72927 A1 | 10/2001 |
| WO | 03 078541 | 9/2003 |
| WO | WO 2004/034751 A1 | 4/2004 |
| WO | 2004 066685 | 8/2004 |
| WO | WO 2004/066685 A1 * | 8/2004 |
| WO | WO 2004/113468 A1 | 12/2004 |
| WO | WO 2005022962 A1 * | 3/2005 |
| WO | 2005 057987 | 6/2005 |
| WO | 2005 076669 | 8/2005 |
| WO | 2005 079118 | 8/2005 |
| WO | 2005 084083 | 9/2005 |
| WO | 2005 085387 | 9/2005 |

OTHER PUBLICATIONS

Machine English translation JP 2000-169448 A. May 20, 2011.*
M. A. Baldo, et al., "Very High-Efficiency Green Organic Light-Emitting Devices Based on Electrophosphorescence", Applied Physics Letters, vol. 75, No. 1, pp. 4-6, 1999.
Third Party's Opinion issued Feb. 8, 2012, in European Patent Application No. 05814748.9.
Office Action issued Jun. 9, 2011, in China patent Application No. 200580044718.X (with English translation).
Japanese Office Action issued Jan. 31, 2012 in patent application No. 2005-355790.
Office Action issued Apr. 16, 2012, in Taiwanese Patent Application No. 094145599 filed Dec. 21, 2005 (with English translation).
Office Action issued Jun. 11, 2012, in European Patent Application No. 05814748.9 filed Dec. 9, 2005.

* cited by examiner

[Fig.1]
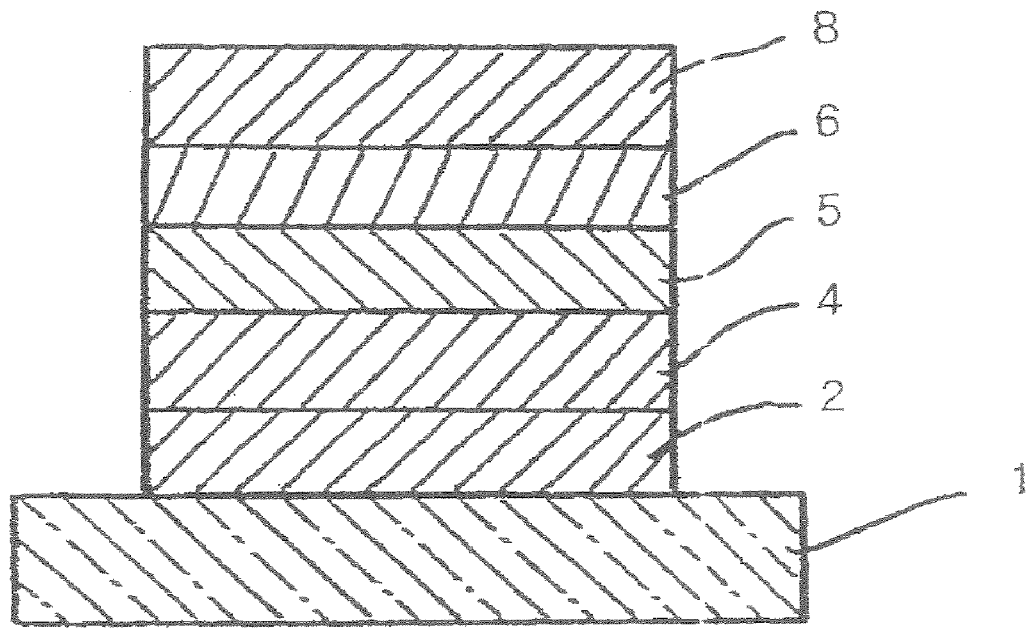
[Fig.2]
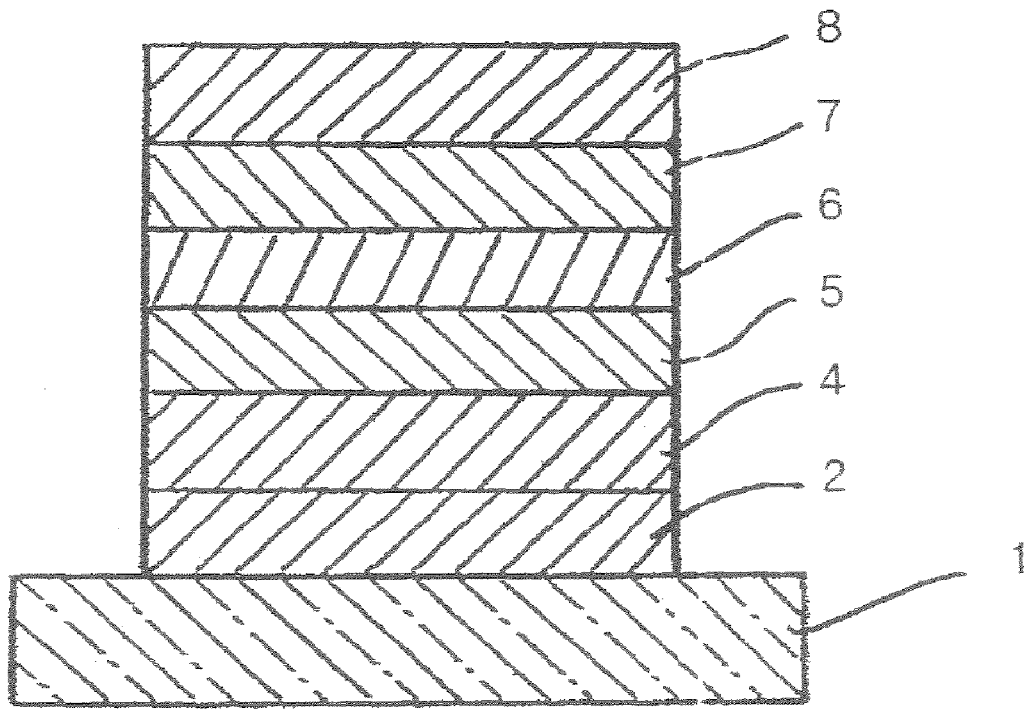

[Fig.3]
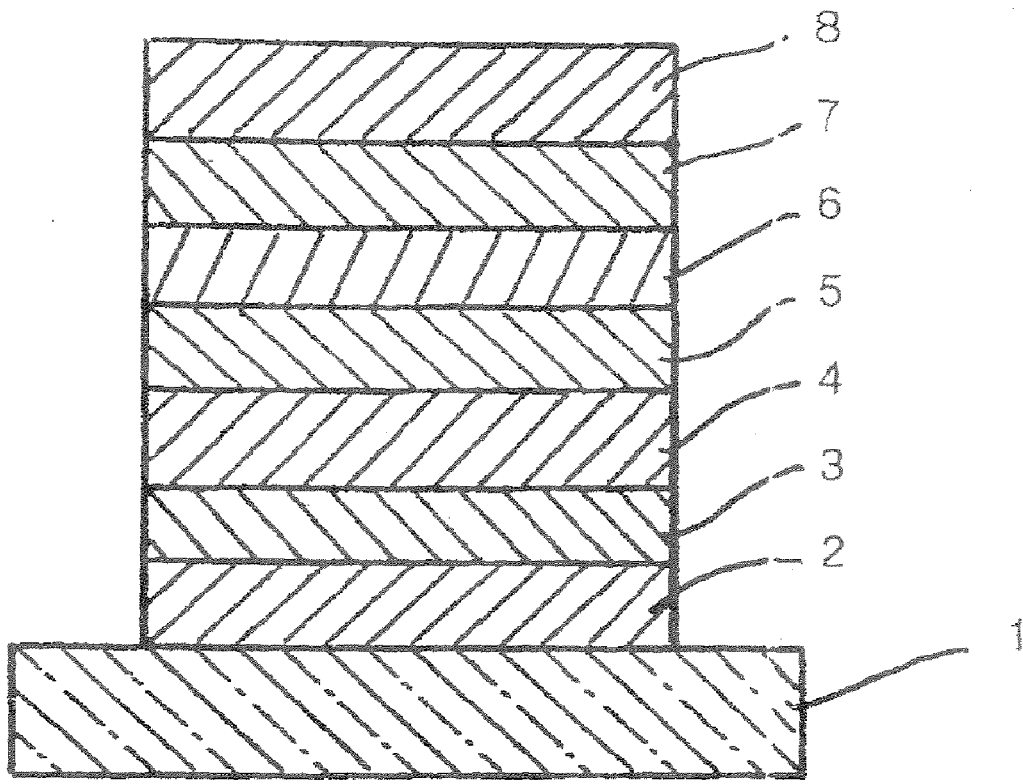
[Fig.4]
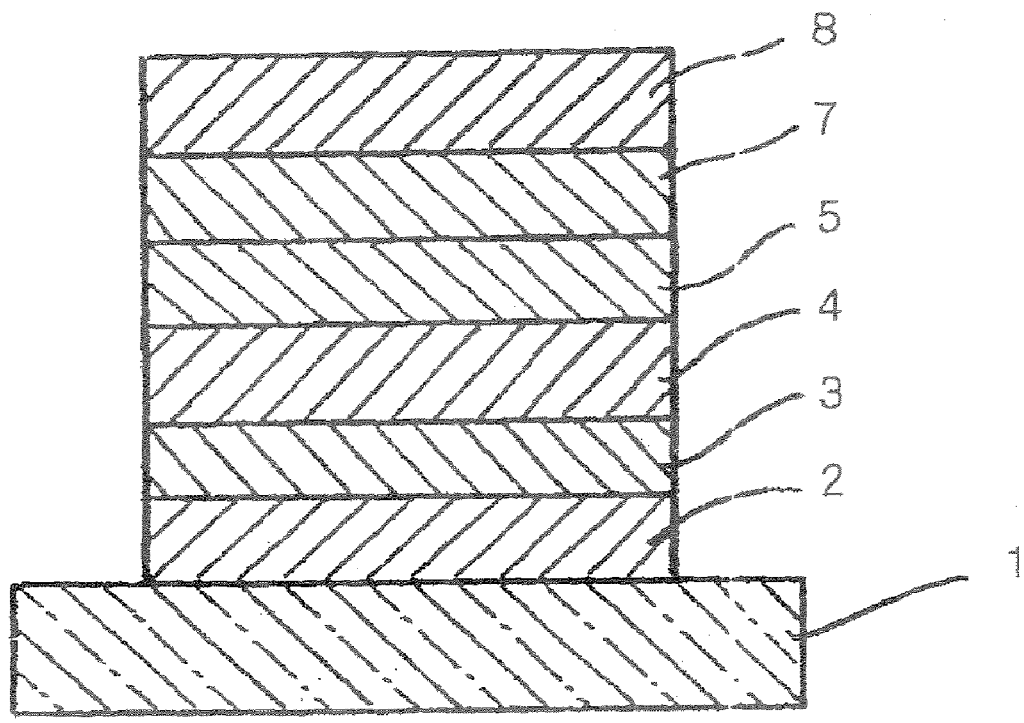

ORGANIC COMPOUND, CHARGE-TRANSPORTING MATERIAL, AND ORGANIC ELECTROLUMINESCENT ELEMENT

FIELD OF THE INVENTION

The present invention relates to novel organic compounds and charge transporting materials, and organic electroluminescent devices using the organic compounds. More specifically, it relates to organic compounds and charge transporting materials which are stable even when repeatedly subjected to electric oxidation and/or reduction, and organic electroluminescent devices using the organic compounds and having a high luminous efficiency and a long lifetime.

BACKGROUND OF THE INVENTION

There have been developed electroluminescent devices using organic thin films. Such electroluminescent devices using organic thin films, namely, organic electroluminescent devices each generally include a substrate bearing an anode, a cathode, and one or more organic layers. The one or more organic layers are arranged between the two electrodes and include at least a light-emitting layer. Such organic layers may include a hole injection layer (anode buffer layer), a hole transport layer, a hole blocking layer, an electron transport layer, and an electron injection layer, in addition to a light-emitting layer. These layers are generally arranged or laminated between the anode and the cathode to constitute an organic electroluminescent device.

Organic electroluminescent devices have used fluorescence emission. As an attempt to raise luminous efficiency of the devices, it has also been examined to use phosphorescence instead of fluorescence. Sufficient luminous efficiency, however, has not yet been obtained even when phosphorescent emission is used.

For example, Appl. Phys. Lett., 75, 4 (1999) discloses the following biphenyl derivative as a host material.

[Chemical Formula 1]

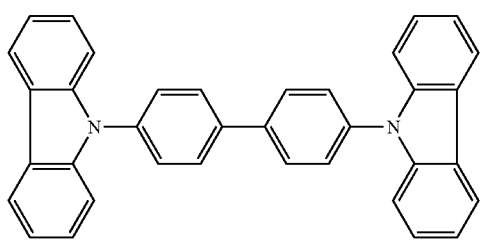

However, an organic electroluminescent device using the biphenyl derivative does not yield a satisfactorily high luminous efficiency, because the recombination of charge tends to occur unevenly in the vicinity of the cathode, and the device has poor balance in charge recombination.

Japanese Unexamined Patent Application Publication No. 6-1972 discloses an organic electroluminescent device using the following compound:

[Chemical Formula 2]

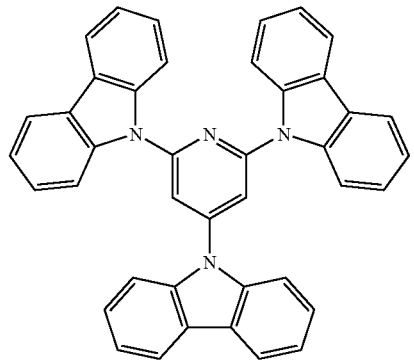

The compound, however, shows light emission only under a high voltage and is supposed to be insufficient in luminance and luminous efficiency.

Japanese Unexamined Patent Application Publications No. 2000-186066 and No. 2000-169448 propose, as hole transporting materials and light-emitting layer materials for fluorescent emitting devices or for electrophotographic photoreceptors, pyridine compounds typified by the following compounds:

[Chemical Formula 3]

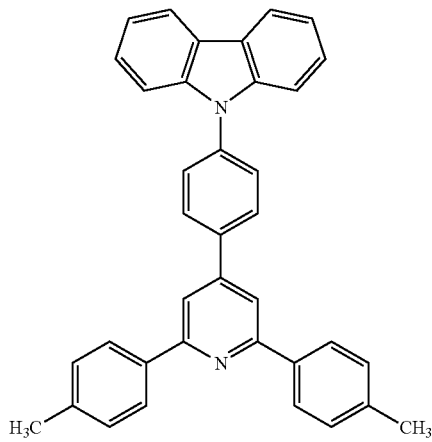

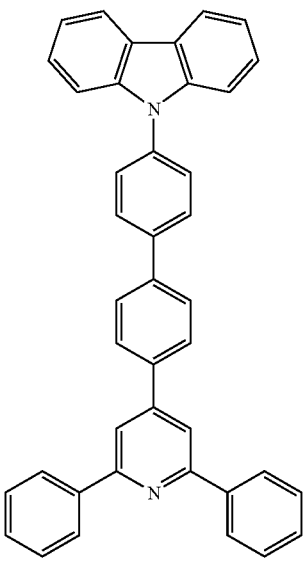
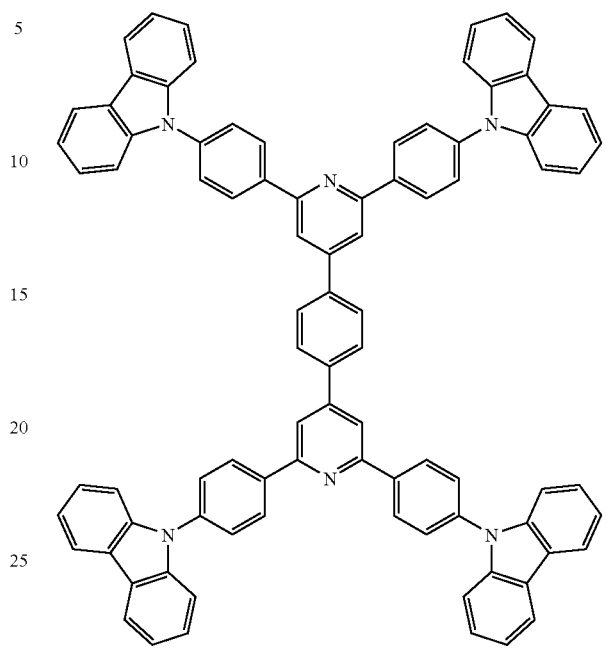
Japanese Unexamined Patent Application Publication No. 2003-22893 discloses, as a material for organic electroluminescent devices, the following compound:
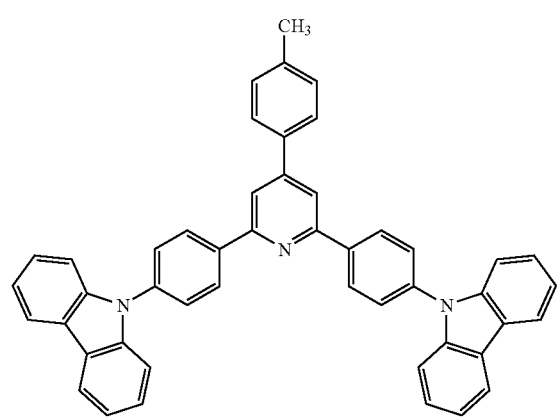
[Chemical Formula 4]
PCT International Publication Number WO 03/078541 discloses, as materials for organic electroluminescent devices, the following compounds:

[Chemical Formula 5]

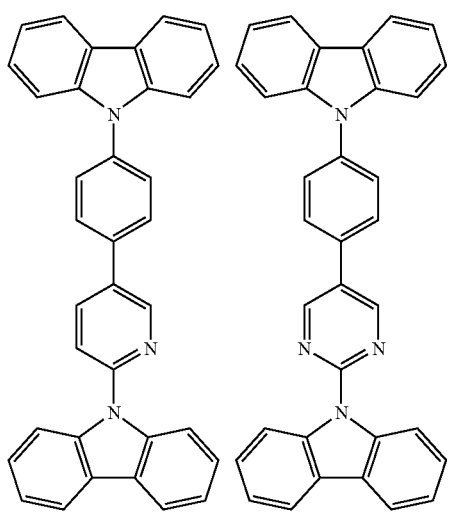

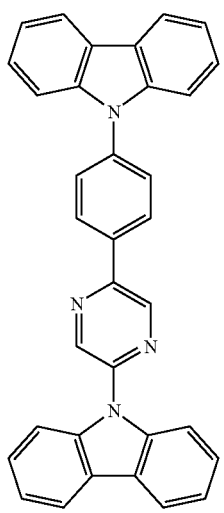

The compounds described in these patent documents, however, show a significant polarization of charge in the molecule and have a relatively low triplet excitation level, because they have such a structure as to enable the conjugation of a nitrogen atom on the pyridine ring, triazine ring, pyrimidine ring, or pyrazine ring with a nitrogen atom on the carbazole ring. In addition, they have a poor durability as materials for organic electroluminescent devices. Accordingly, they are insufficient in performance for use in blue-light emitting devices and phosphorescent emitting devices. In addition, the compounds show a poor electrochemical durability when they are not fully substituted at the 2-, 4-, and 6-positions of the pyridine ring, at the 2-, 4-, and 6-positions of the pyrimidine ring, or at the 2-, 3-, 5-, and 6-positions of the pyrazine ring.

PCT International Publication Number WO 03/080760 discloses the following compounds as materials for organic electroluminescent devices.

[Chemical Formula 6]

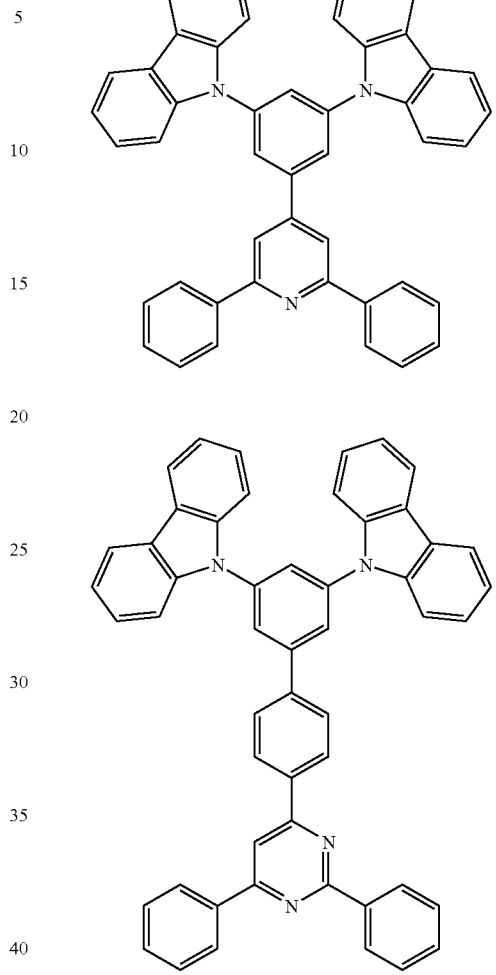

These compounds, however, are susceptible to localization of positive or negative charges when the molecules are subjected to electric oxidation or reduction. This is because, in these compounds, two carbazolyl groups serving as electron-donating groups are substituted on one aromatic ring (a benzene ring herein) at such positions (the meta-position) as to prohibit the conjugation with each other through the aromatic ring. The compounds having such a partial structure have a poor durability against electric oxidation and reduction. Even though the compounds further include a pyridine ring or a pyrimidine ring in order to improve the durability against electric reduction, the pyridine ring and the pyrimidine ring still have a decreased durability against electric reduction. This is because the aromatic ring (benzene ring herein) substituted with two carbazolyl groups is located at the para-position with respect to the nitrogen atom of the pyridine ring and the pyrimidine ring, the aromatic ring is so located as to enable the conjugation with the pyridine ring and the pyrimidine ring, and the aromatic ring acts to give electrons to the pyridine ring and the pyrimidine ring.

PCT International Publication Number WO 03/080760 also discloses the following compound:

[Chemical Formula 7]

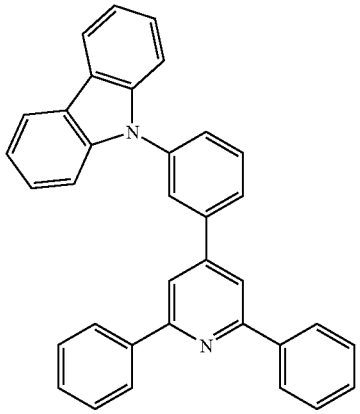

This compound is expected to have an improved durability against electric oxidation, but has a poor hole transporting ability, because it has only one carbazolyl group. Accordingly, the compound is not in good balance between the hole transporting ability and the electron transporting ability and is not suitable as a host material for a light-emitting layer of an organic electroluminescent device. In addition, it has a poor thermal stability.

SUMMARY OF THE INVENTION

Accordingly, an object of the present invention is to provide an organic compound and a charge transporting material exhibiting both excellent hole transporting ability and excellent electron transporting ability, showing satisfactory durability against electric oxidation/reduction, and having a high triplet excitation level. Another object of the present invention is to provide an organic electroluminescent device which uses the organic compound, emits light with a high efficiency, is highly stably driven, and has a long lifetime.

Specifically, according to a first aspect of the present invention, there is provided an organic compound represented by following Formula (I).

According to a second aspect of the present invention, there is provided a charge transporting material including the organic compound according to the first aspect.

According to a third aspect of the present invention, there is provided an organic electroluminescent device including a substrate bearing an anode, a cathode, and an organic light-emitting layer arranged between the two electrodes, in which the organic electroluminescent device includes the organic compound according to the first aspect.

[Chemical Formula 8]

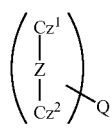

(I)

In Formula (I), $Cz^1$ and $Cz^2$ each represent a carbazolyl group;

Z represents a direct bond or an arbitrary linkage group enabling the conjugation of nitrogen atoms in the carbazole rings of $Cz^1$ and $Cz^2$ with each other;

each of $Cz^1$, $Cz^2$, and Z may be substituted;

Q represents a direct bond connecting to "G" in following Formula (II):

[Chemical Formula 9]

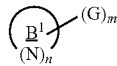

(II)

wherein Ring $B^1$ represents a six-membered aromatic heterocyclic ring having "n" nitrogen atom(s) as hetero atom(s);

"n" represents an integer of from 1 to 3;

Gs connect to carbon atoms at the ortho position and the para position with respect to the nitrogen atom(s) in Ring $B^1$;

G represents a direct bond or an arbitrary linkage group connecting to Q when G connects to Q;

G represents an aromatic hydrocarbon group when G does not connect to Q;

"m" represents an integer of from 3 to 5;

plural Gs in one molecule may be the same as or different from one another; and

Ring $B^1$ may have one or more substituents in addition to Gs.

An organic compound according to the first aspect exhibits both excellent hole transporting ability and excellent electron transporting ability, shows excellent durability against electric oxidation/reduction, and has a high triplet excitation level. Accordingly, an organic electroluminescent device according to the third aspect using this organic compound can emit light with a high luminance and a high efficiency, has increased stability, can be driven highly stably, and can have a longer lifetime.

The organic electroluminescent device according to the third aspect can supposedly be applied to a flat panel display (e.g., for office automation (OA) computers or as a wall-hanging television), an onboard display device, display for a cellular phone, a light source utilizing the characteristics as a flat light-emitting device (e.g., a light source for a copying machine or a backlight source for a liquid crystal display or a meter), an indication panel, or a beacon light.

The organic compound according to the first aspect inherently shows excellent oxidation/reduction stability and can thereby be advantageously applied to an electrophotographic photoreceptor, in addition to an organic electroluminescent device.

The organic compound according to the first aspect is useful for a light-emitting material; a material for solar cell; a material for a battery, such as an electrolytic solution, an electrode, a separation membrane or a stabilizer; a material for medical use; a material for paint; a material for coating; a material for organic semi-conductor; a material for toiletries; a material for antistatic material; and a material for thermoelectric device; as well as for a charge transporting material.

The charge transporting material according to the second aspect can be used as a hole injecting material, a hole transport material, a light-emitting material, a host material, an electron injecting material, or an electron transport material.

BRIEF DESCRIPTION OF THE DRAWINGS

FIG. 1 is a schematic cross-sectional view showing an organic electroluminescent device according to an embodiment of the present invention.

FIG. 2 is a schematic cross-sectional view showing an organic electroluminescent device according to another embodiment of the present invention.

FIG. 3 is a schematic cross-sectional view showing an organic electroluminescent device according to yet another embodiment of the present invention.

FIG. 4 is a schematic cross-sectional view showing an organic electroluminescent device according to still another embodiment of the present invention.

DETAILED DESCRIPTION OF THE PREFERRED EMBODIMENTS

Some embodiments of organic compounds, charge transporting materials, and organic electroluminescent devices according to the present invention will be illustrated in detail below. It should be noted, however, that following description on components is illustrated only by way of example (representative examples), and the present invention is not limited thereto unless departing from she scope and spirit of the present invention.

[Organic Compounds]

An organic compound according to the present invention is represented by Formula (I).

[1] Structural Characteristics

An organic compound according to the present invention includes a moiety mainly bearing a hole transporting property and a moiety mainly bearing an electron transporting property in such a manner that the two moieties do not significantly interfere with each other.

The moiety mainly bearing a hole transporting property is the moiety of $Cz^1$-Z-$Cz^2$, and the moiety mainly bearing an electron transporting property is the moiety of -Q-G-Ring $B^1$ in Formula (I). The moiety mainly bearing a hole transporting property shows excellent durability against electric oxidation. The moiety mainly bearing an electron transporting property shows excellent durability against electric reduction.

In the moiety of $Cz^1$-Z-$Cz^2$ acting as a moiety mainly bearing a hole transporting property, a nitrogen atom of $Cz^1$ conjugates with a nitrogen atom of $Cz^2$ through Z. The conjugation between the nitrogen atom of $Cz^1$ and the nitrogen atom of $Cz^2$ allows the molecule to have an increased dielectric constant. In addition, charges become uniformly distributed, and this allows the molecule to have a decreased ionization potential and an enlarged intramolecularly and intramolecularly overlapping of orbital. Thus, the compound can have an increased hole transporting property.

If a nitrogen atom of $Cz^1$ and a nitrogen atom of $Cz^2$ do not conjugate with each other, an excessive positive electric charge concentrates on Z (for example, on an aromatic hydrocarbon group) or a positive electric charge is unevenly distributed in at least one of the N-, 1-, 3-, 6-, and 8-positions of a carbazole ring when the compound undergoes electric oxidation. The organic compound therefore has a significantly undesirably decreased durability against electric oxidation.

In contrast, when a nitrogen atom of $Cz^1$ and a nitrogen atom of $Cz^2$ conjugate with each other, a positive electric charge can be relatively homogenously distributed in both the moieties of $Cz^1$ and $Cz^2$, and the resulting organic compound shows excellent durability against electric oxidation.

The phrase "nitrogen atoms conjugate with each other" as used in an organic compound according to the present invention has the same meaning as that the nitrogen atoms are connected to each other through a partial structure represented by:

[Chemical Formula 10]

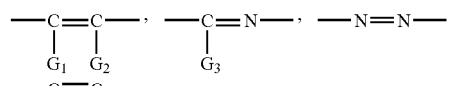

wherein either of cis- and trans-form will do, and wherein $G_1$, $G_2$ and $G_3$ each independently represent a hydrogen atom or an arbitrary substituent, or constitutes a part of an aromatic hydrocarbon ring or an aromatic heterocyclic ring, or any combination of these partial structures.

In addition to $Cz^1$ and $Cz^2$, one or more carbazolyl groups can be connected to Z. The number of carbazolyl groups to be connected to Z is preferably 2 or more and 4 or less, more preferably 2 or 4, and most preferably 2. In other words, it is most preferred that only $Cz^1$ and $Cz^2$ are connected to Z.

In an organic compound according to the present invention, nitrogen atoms of $Cz^1$ and $Cz^2$ preferably do not conjugate with a nitrogen atom of Ring $B^1$. Specifically, $Cz^1$ and $Cz^2$ are preferably connected to Ring $B^1$ through such a linkage group as to prohibit the conjugation between nitrogen atoms of $Cz^1$ and $Cz^2$ and a nitrogen atom of Ring $B^1$. This is because, if nitrogen atoms of $Cz^1$ and $Cz^2$ serving as electron-rich moieties are structurally capable of conjugating with a nitrogen atom of Ring $B^1$ serving as an electron-deficient moiety, the interaction between the electron-rich moieties and the electron-deficient moiety may become significantly great and may thereby adversely affect the durability against oxidation the durability against reduction of the moieties, respectively. In addition, intramolecular polarization of charge occurs, and the resulting compound may have a significantly decreased triplet excitation level.

The phrase "nitrogen atoms of $Cz^1$ and $Cz^2$ do not conjugate with a nitrogen atom of Ring $B^1$" is an antonym to the phrase that "nitrogen atoms conjugate with each other" and has the same meaning as that these moieties are not connected to each other through the above-mentioned partial structure.

[2] Components In Formula (I)

<$Cz^1$ and $Cz^2$>

$Cz^1$ and $Cz^2$ in Formula (I) each independently represent a carbazolyl group. $Cz^1$ and $Cz^2$ can each independently be, for example, N-carbazolyl group, 1-carbazolyl group, 2-carbazolyl group, 3-carbazolyl group, or 4-carbazolyl group. $Cz^1$ and $Cz^2$ may be the same as or different from each other.

For yielding a high triplet excitation level and excellent electrochemical stability, $Cz^1$ and $Cz^2$ are each independently preferably N-carbazolyl group or 2-carbazolyl group, of which N-carbazolyl group is most preferred.

Specifically, $Cz^1$ and $Cz^2$ are particularly preferably both N-carbazolyl groups.

When $Cz^1$ and $Cz^2$ are N-carbazolyl groups, Formula (I) is represented by following Formula (I-1):

[Chemical Formula 11]

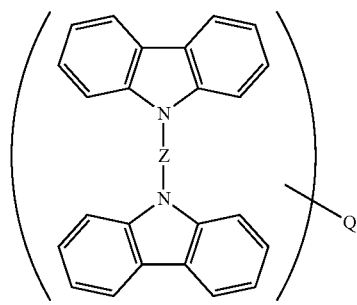

(I-1)

wherein $Cz^1$ and $Cz^2$ may each independently have an arbitrary substituent.

The phrase "may be substituted (or may have a substituent)" herein means "may have one or more substituents".

Preferred examples as the substituents include alkyl groups, aromatic hydrocarbon groups, acyl groups, alkoxy groups, aryloxy groups, alkylthio groups, arylthio groups, alkoxycarbonyl groups, aryloxycarbonyl groups, halogen atoms, arylamino groups, alkylamino groups, and aromatic heterocyclic groups, of which alkyl groups, aromatic hydrocarbon groups, and aromatic heterocyclic groups are more preferred. The substituents herein are especially preferably aromatic hydrocarbon groups for yielding a high triplet excitation level and for avoiding decrease in electric durability due to uneven distribution of charge. Specific examples thereof include monovalent groups derived from monocyclic six-membered rings or from condensed rings having condensed two to five six-membered rings, such as benzene ring, naphthalene ring, anthracene ring, phenanthrene ring, perylene ring, tetracene ring, pyrene ring, benzopyrene ring, chrysene ring, triphenylene ring, and fluoranthene ring; and monovalent groups each including two or more of these groups combined with each other, such as biphenyl group and terphenyl group.

The total molecular weight of substituents on each of $Cz^1$ and $Cz^2$ is preferably 500 or less and more preferably 250 or less. Most preferably, $Cz^1$ and $Cz^2$ are unsubstituted.

<Z>

In Formula (I), Z represents a direct bond or an arbitrary linkage group enabling the conjugation of nitrogen atoms in the carbazole rings of $Cz^1$ and $Cz^2$ with each other.

The arbitrary linkage group is preferably an aromatic hydrocarbon group. Specific examples thereof include bivalent linkage groups derived from monocyclic six-membered rings or from condensed rings having condensed two to five six-membered rings, such as benzene ring, naphthalene ring, anthracene ring, phenanthrene ring, perylene ring, tetracene ring, pyrene ring, benzopyrene ring, chrysene ring, triphenylene ring, and fluoranthene ring; and bivalent linkage groups each including two or more of these groups, such as biphenylene group and terphenylene group. Z is preferably a direct bond or a bivalent linkage group including one to eight benzene rings bound to each other, such as phenylene group, biphenylene group, or terphenylene group.

When Z is an arbitrary linkage group, Z may have an arbitrary substituent. Preferred examples of the substituents include alkyl groups, aromatic hydrocarbon groups, acyl groups, alkoxy groups, aryloxy groups, alkylthio groups, arylthio groups, alkoxycarbonyl groups, aryloxycarbonyl groups, halogen atoms, arylamino groups, alkylamino groups, and aromatic heterocyclic groups. Among them, alkyl groups, aromatic hydrocarbon groups, and aromatic heterocyclic groups are more preferred, of which aromatic hydrocarbon groups are particularly preferred. Specific examples of such preferred substituents include monovalent groups derived from monocyclic six-membered rings or from condensed rings having condensed two to five six-membered rings, such as benzene ring, naphthalene ring, anthracene ring, phenanthrene ring, perylene ring, tetracene ring, pyrene ring, benzopyrene ring, chrysene ring, triphenylene ring, and fluoranthene ring; and monovalent groups each including two or more of these groups combined with each other, such as biphenyl group and terphenyl group.

The molecular weight of Z is preferably 1000 or less and more preferably 500 or less.

Z is typically preferably a direct bond or $-(Ph)_p-$, wherein Ph represents a phenylene group which may be substituted; and "p" represents an integer of from 1 to 8 and is preferably an integer of 1 or 2.

<Examples of Formula (I)>

Examples of the moiety of the partial structure represented by Formula (I), except for the moiety represented by Formula (II), will be illustrated below, which, however, by no means limit the scope of the present invention.

[Chemical Formula 12]

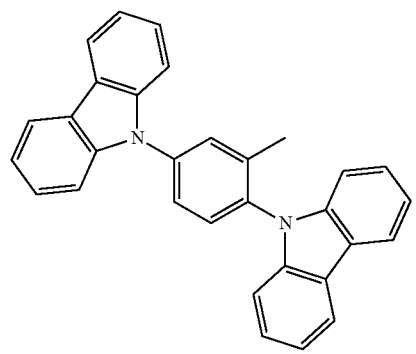

V-1

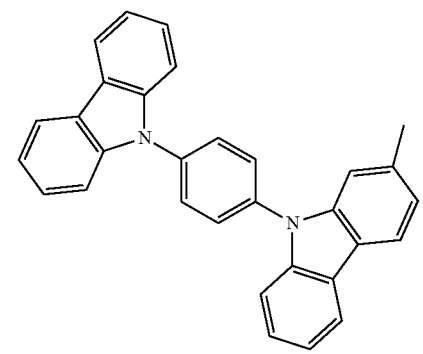

V-2

-continued
V-3
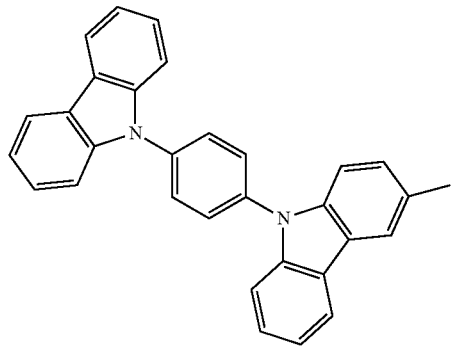
V-4
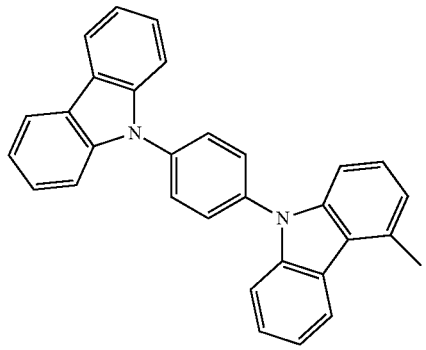
V-5
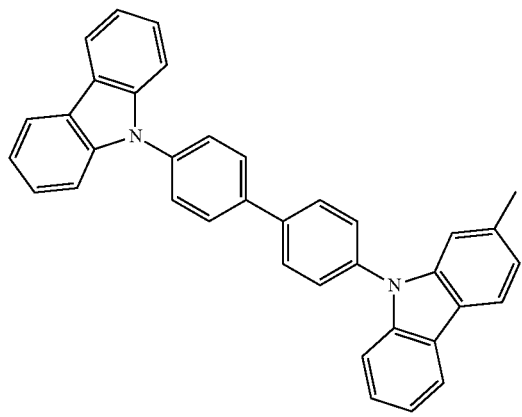
V-6
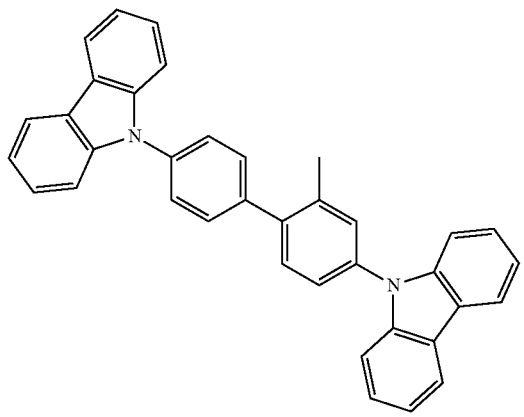
V-7
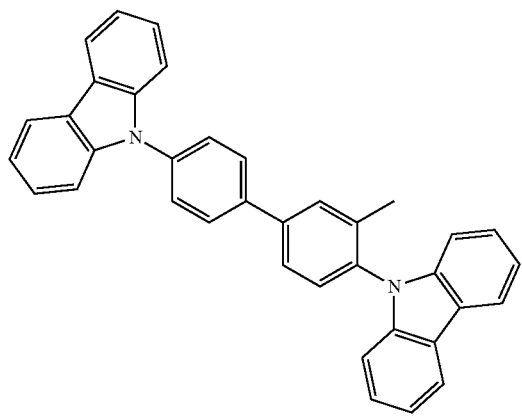
V-8
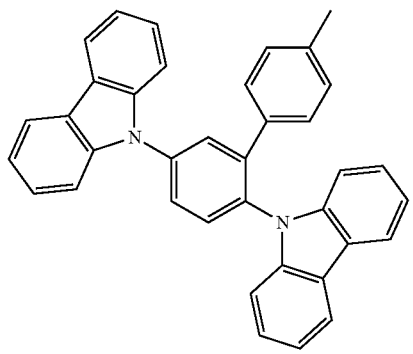
V-9
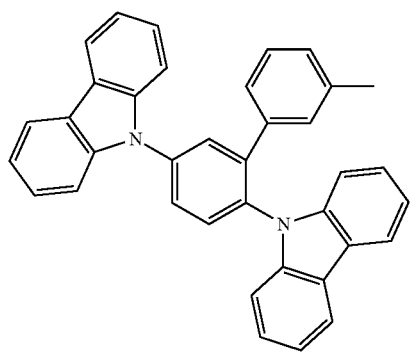

[Chemical Formula 13]
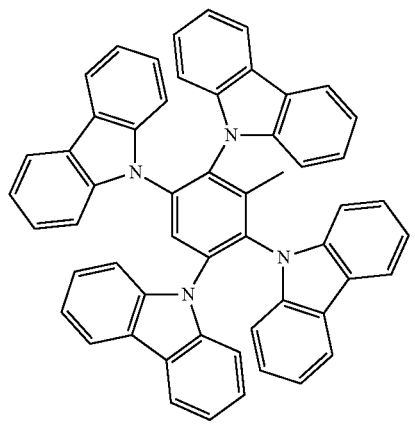
V-10
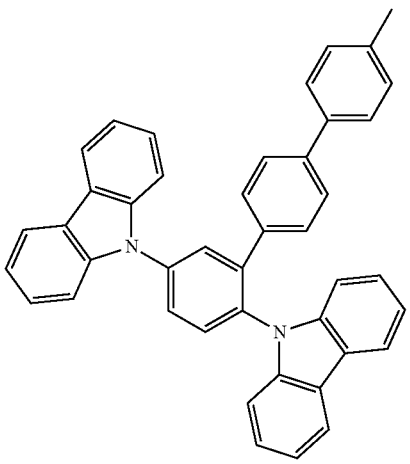
V-11
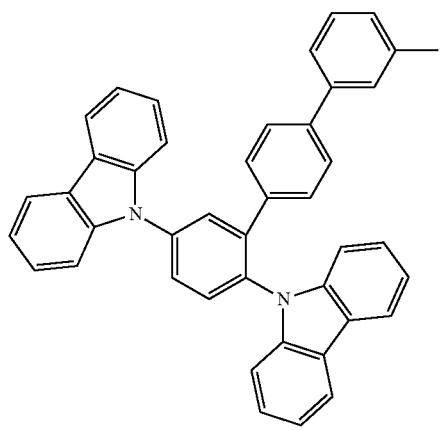
V-12
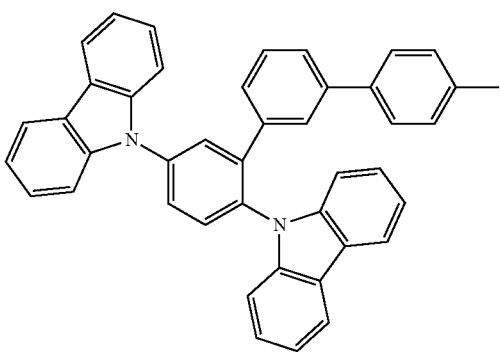
V-13
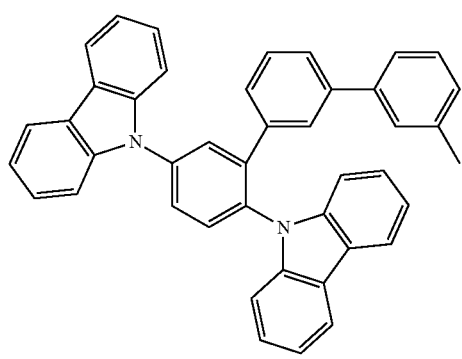
V-14
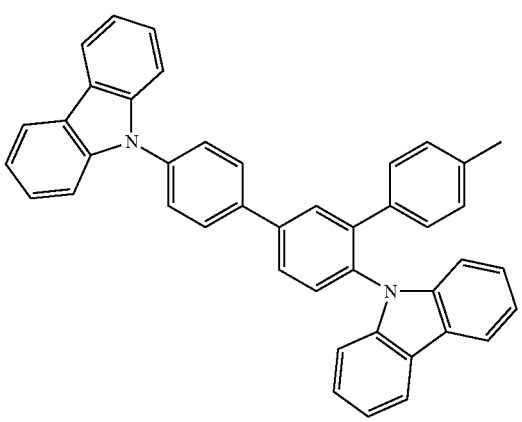
V-15

V-16
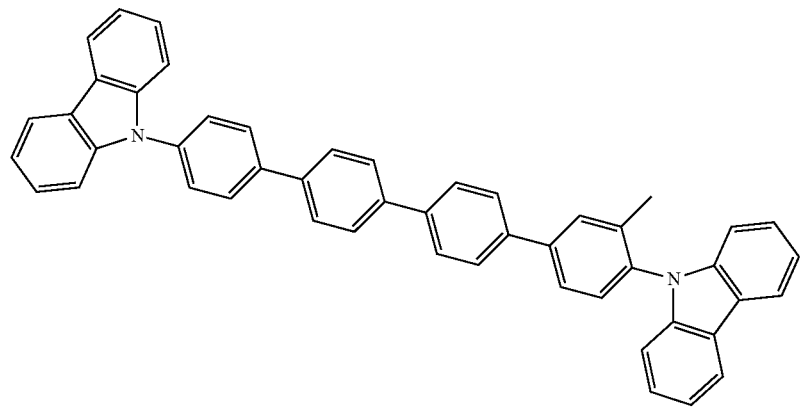
[Chemical Formula 14]
V-17
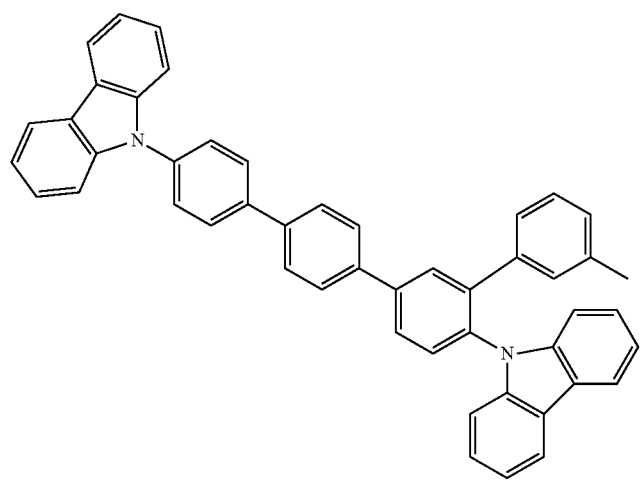
V-18
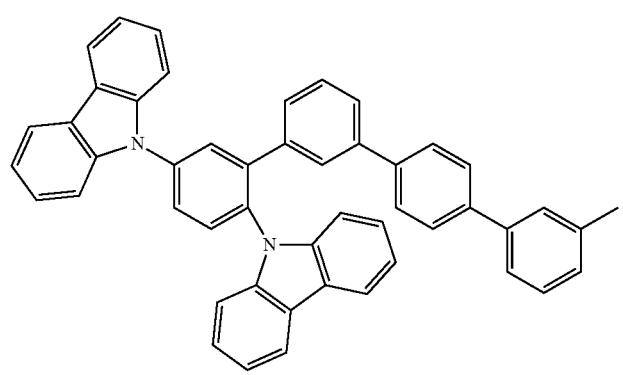
V-19
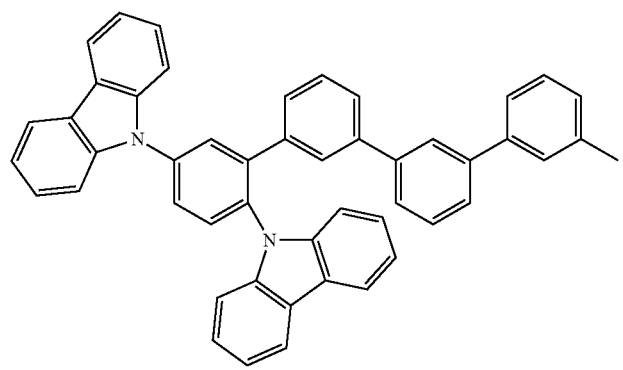

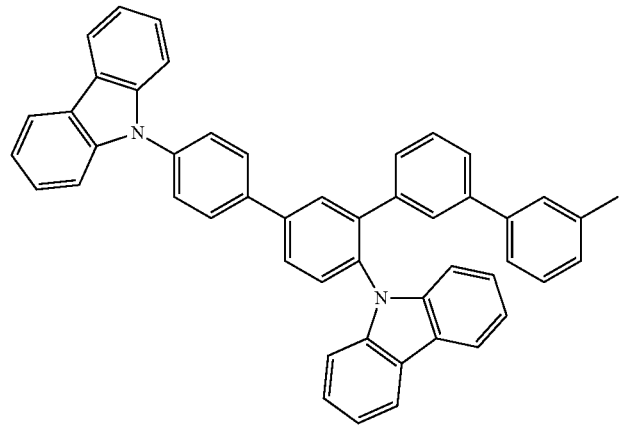
V-20
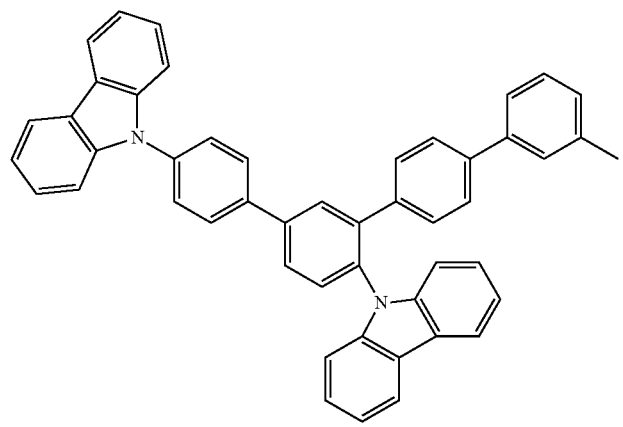
V-21
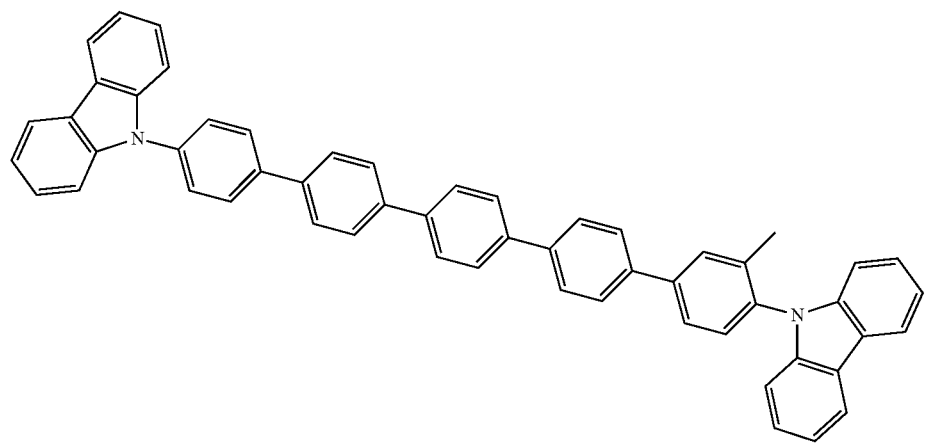
V-22

[Chemical Formula 15]
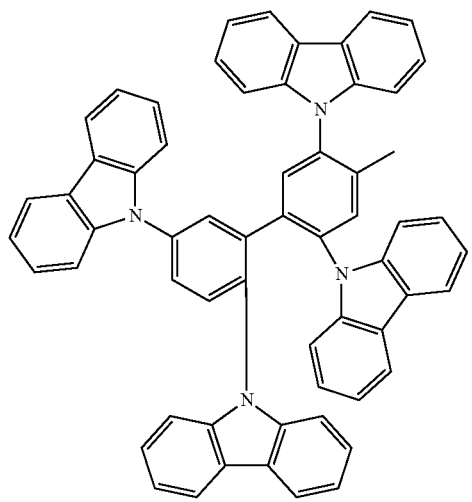
V-23
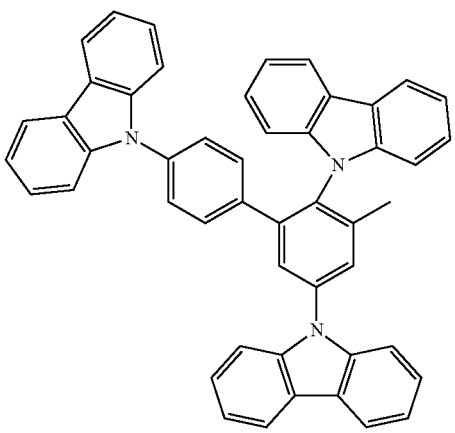
V-24
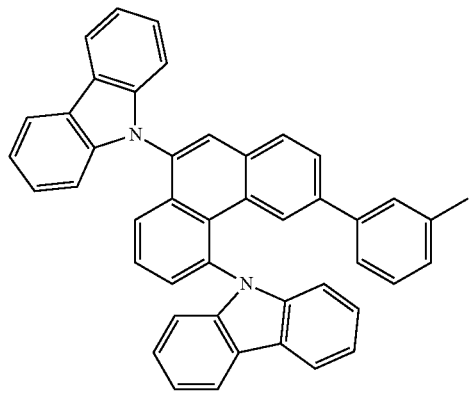
V-25
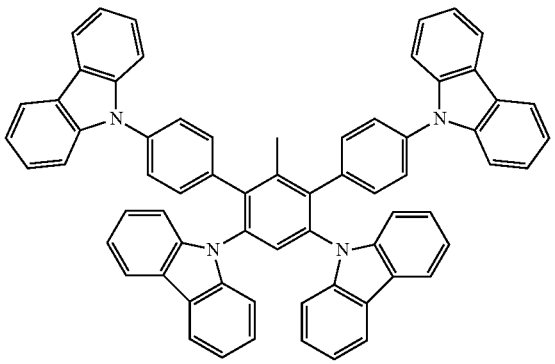
V-26
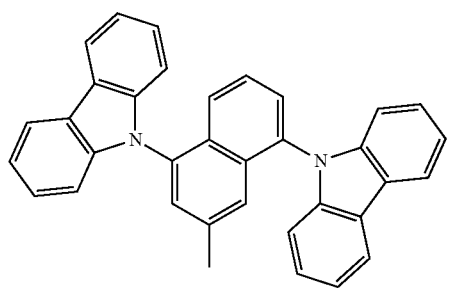
V-27
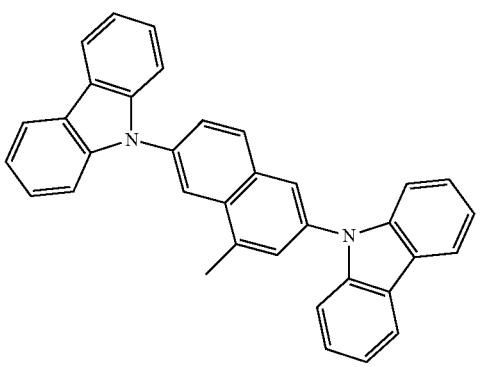
V-28

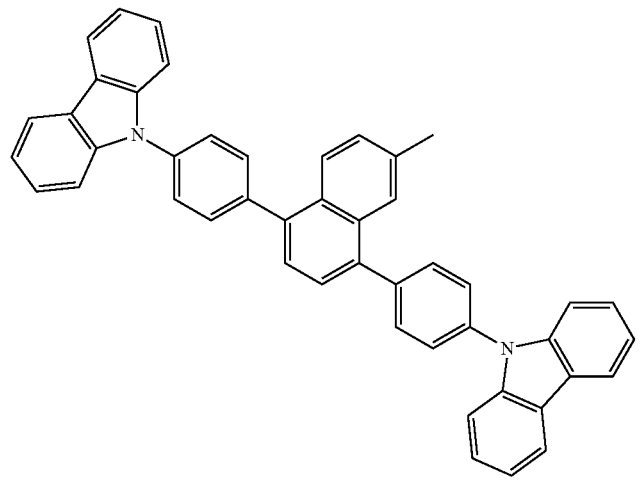
V-29
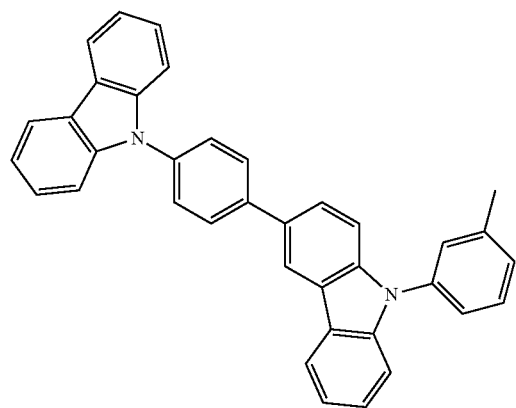
V-30
[Chemical Formula 16]
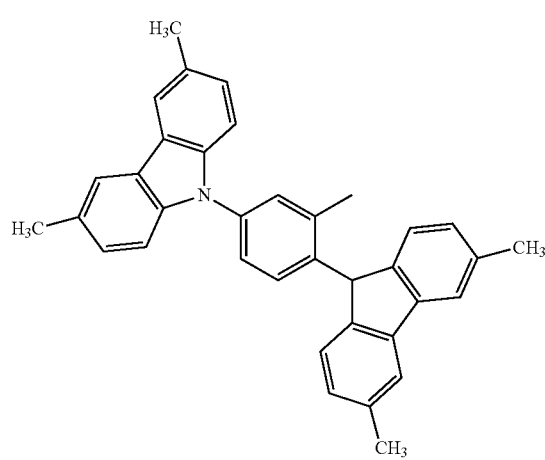
V-31

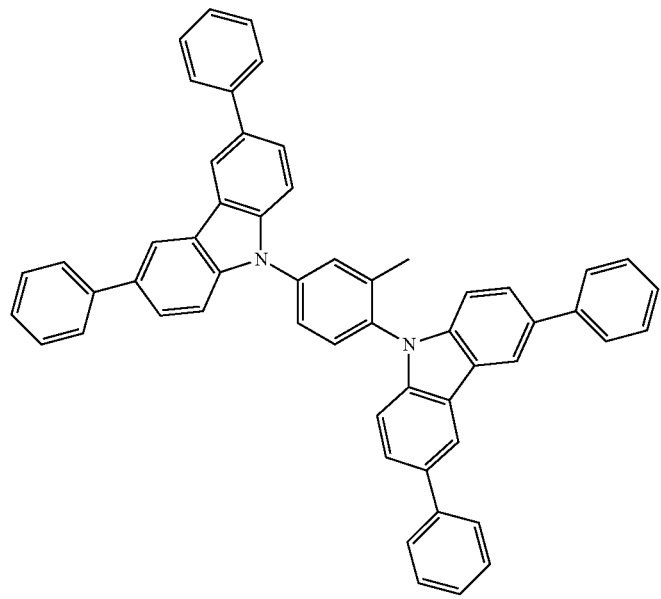
V-32
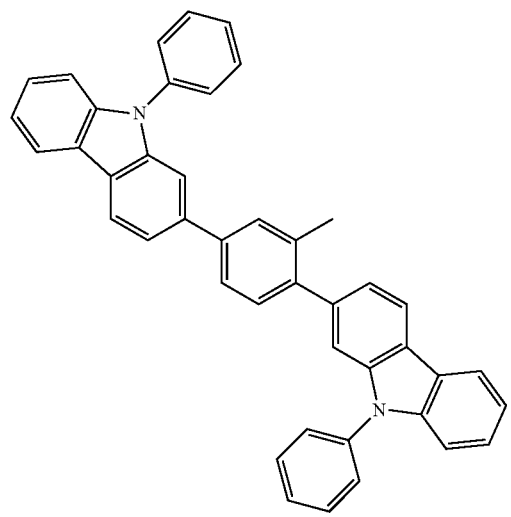
V-33
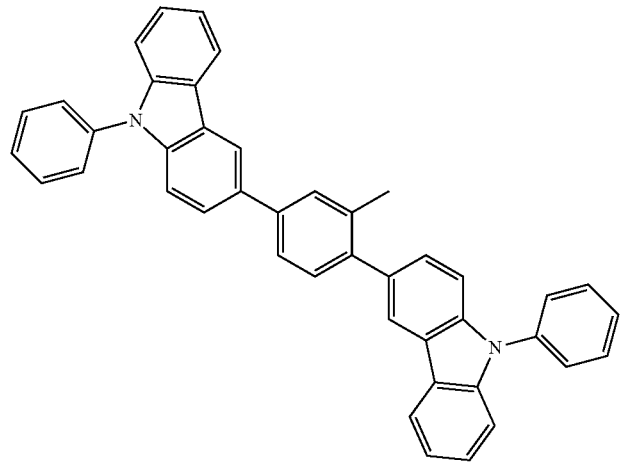
V-34

Of the examples of the partial structure, the moieties V-1, V-2, V-4 to V-15, V-17 to V-21, V-27, V-28, and V-31 to V-33 are preferred, and the moieties V-1, V-6 to V-9, V-11 to V-15, V-31, and V-32 are more preferred, of which the moieties V-1, V-7, V-9, V-13 to V-15 are most preferred.

<Q>

Q represents a direct bond connecting to at least one of Gs in following Formula (II):

[Chemical Formula 17]

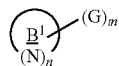

(II)

The molecular weight of the moiety represented by Formula (II) is preferably 70 or more, and more preferably 75 or more and is preferably 1000 or less, and more preferably 500 or less. If the moiety has a molecular weight lower than the above-specified lower limit, the resulting compound may have deteriorated aromaticity. If the moiety has a molecular weight exceeding the upper limit, the resulting compound may have an elevated vaporization temperature and become difficult to form a film by vapor deposition, or may have a poor solubility and become difficult to form a film by a wet process.

In Formula (ii), Ring $B^1$ may be a six-membered aromatic heterocyclic ring having "n" nitrogen atom(s) as hetero atom(s); and "n" represents an integer of from 1 to 3. When an organic compound according to the present invention has two or more Rings $B^1$ per one molecule, these rings may be the same as or different from each other.

The moiety represented by Formula (II) is preferably a moiety represented by one of following Formulae (II-1) to (II-4):

[Chemical Formula 18]

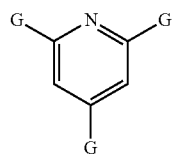

(II-1)

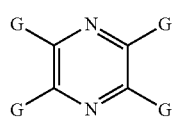

(II-2)

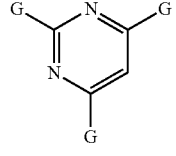

(II-3)

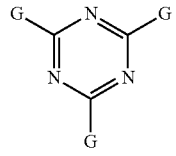

(II-4)

Groups represented by Formula (II), typified by groups represented by Formulae (II-1) to (II-4), act as a moiety mainly bearing an electron transporting property and exhibit excellent durability against electric reduction in an organic compound according to the present invention.

An organic compound may include one to eight groups represented by any of Formulae (II-1) to (II-4) per one molecule. If the organic compound includes two or more of these groups, they are preferably non-conjugate with each other in the molecule. The target electron transporting property can be sufficiently exhibited even when the organic compound includes only one of these groups. The organic compound preferably includes one group represented by any of Formulae (II-1) to (II-4). This is also preferred for the good balance between the hole transporting ability and the electron transporting ability, for satisfactory thermal stability and evaporation property required upon film formation by vapor deposition, for good solubility required upon film formation by a wet process, for good stability in the air (resistance to oxidation), or for easily yielding a high-purity compound.

Groups represented by the formulae will be separately illustrated.

Group Represented by Formula (II-1)

A pyridine ring represented by Formula (II-1) can have durability by being substituted at the 2-, 4-, and 6-positions.

The pyridine ring may be substituted at the 3- and 5-positions. Preferred examples of the substituents herein are aryl groups such as phenyl group; heteroaryl groups such as pyridyl group; and alkyl groups such as methyl group. However, the pyridine ring is most preferably unsubstituted at the 3- and 5-positions, from the viewpoint of yielding excellent electrochemical stability.

Group Represented by (II-2)

A pyrazine ring represented by Formula (II-2) can have durability against electric reduction by being substituted at the 2-, 3-, 5-, and 6-positions.

Group Represented by (II-3)

A pyrimidine ring represented by Formula (II-3) can have durability against electric reduction by being substituted at the 2-, 4-, and 6-positions.

The pyrimidine ring may be substituted at the 5-position. Preferred examples of the substituent herein are aromatic hydrocarbon groups such as phenyl group; aromatic heterocyclic groups such as pyridyl group; and alkyl groups such as methyl group. However, the pyrimidine ring is most preferably unsubstituted at the 5-position from the viewpoint of yielding excellent electrochemical stability.

Group Represented by (II-4)

A triazine ring represented by Formula (II-4) can have durability against electric reduction by being substituted at the 2-, 4-, and 6-positions.

Ring $B^1$ is especially preferably a pyridine ring represented by Formula (II-1), namely, a group represented by Formula (II) wherein "n" is 1, from the viewpoints of yielding a high triplet excitation level and excellent electrochemical stability.

In Formula (II), Gs each represent a direct bond or an arbitrary linkage group connecting to Q, or represents an aromatic hydrocarbon group. Gs each connect to carbon atoms at the ortho position and the para position with respect to the nitrogen atom(s) in Ring $B^1$. The number "m" represents an integer of from 3 to 5. Plural Gs in one molecule may be the same as or different from one another.

When G is a direct bond or an arbitrary linkage group connecting to Q, G is preferably a direct bond; a bivalent linkage group derived from a monocyclic six-membered ring or from a condensed rings having condensed two to five six-membered rings, such as benzene ring, naphthalene ring, anthracene ring, phenanthrene ring, perylene ring, tetracene ring, pyrene ring, benzopyrene ring, chrysene ring, triphenylene ring, or fluoranthene ring; or a bivalent linkage group including two or more of these groups combined with each other, such as biphenylene group or terphenylene group. G is more preferably a direct bond or -(Ph)$_p$-, wherein Ph represents a phenylene group which may be substituted; and "p" represents an integer of from 1 to 8 and is preferably an integer of 1 or 2.

The molecular weight of G, if connecting to Q, is preferably 1000 or less and more preferably 500 or less. If the moiety G has a molecular weight exceeding the above-specified upper limit, the resulting compound may have deteriorated aromaticity. If the moiety has a molecular weight exceeding the upper limit, the resulting compound may have an elevated vaporization temperature and become difficult to form a film by vapor deposition, or may have a poor solubility and become difficult to form a film by a wet process.

G represents, if not connecting to Q, an aromatic hydrocarbon group. Any aromatic hydrocarbon group will do as G, if not connecting to Q. Preferred examples of G in this case include monovalent groups derived from monocyclic six-membered rings or from condensed rings having condensed two to five six-membered rings, such as benzene ring, naphthalene ring, anthracene ring, phenanthrene ring, perylene ring, tetracene ring, pyrene ring, benzopyrene ring, chrysene ring, triphenylene ring, and fluoranthene ring; and monovalent groups each containing two or more of these groups combined with each other, such as biphenyl group and terphenyl group. G is more preferably a monovalent group including one to eight benzene rings combined with each other, such as phenyl group, biphenyl group, or terphenyl group.

The molecular weight of G, if not connecting to Q, is preferably 2000 or less, and more preferably 1000 or less. If the moiety G has a molecular weight exceeding the above-specified upper limit, the resulting compound may have deteriorated aromaticity. If the moiety has a molecular weight exceeding the upper limit, the resulting compound may have an elevated vaporization temperature and become difficult to form a film by vapor deposition, or may have a poor solubility and become difficult to form a film by a wet process.

Gs may each have an arbitrary substituent. Preferred as the substituents are alkyl groups, aromatic hydrocarbon groups, acyl groups, alkoxy groups, aryloxy groups, alkylthio groups, arylthio groups, alkoxycarbonyl groups, aryloxycarbonyl groups, halogen atoms, arylamino groups, alkylamino groups, and aromatic heterocyclic groups, of which alkyl groups, aromatic hydrocarbon groups, and aromatic heterocyclic groups are more preferred. Gs are particularly preferably unsubstituted, or substituted with an aromatic hydrocarbon group. Specific examples of such aromatic hydrocarbon groups include monovalent groups derived from monocyclic six-membered rings or from condensed rings having condensed two to five six-membered rings such as benzene ring, naphthalene ring, anthracene ring, phenanthrene ring, perylene ring, tetracene ring, pyrene ring, benzopyrene ring, chrysene ring, triphenylene ring, and fluoranthene ring; and monovalent groups each containing two or more of these groups combined with each other, such as biphenyl group and terphenyl group.

[3] Molecular Weight

The molecular weight of an organic compound according to the present invention is generally 4000 or less, preferably 3000 or less, and more preferably 2000 or less and is generally 200 or more, preferably 300 or more, and more preferably 400 or more.

If an organic compound according to the present invention has a molecular weight exceeding the upper limit, the compound may have significantly decreased sublimability and may become difficult to form a satisfactory film by vapor deposition in the production of an electroluminescent device. Alternatively or in addition, impurities may have higher molecular weights, and the compound may not be sufficiently purified. If an organic compound has a molecular weight lower than the lower limit, the compound may be decreased typically in glass transition temperature, melting point, and vaporization temperature and may have significantly poor thermal stability.

[4] Physical Properties

An organic compound according no the present, invention generally has a glass transition temperature of 50° C. or higher. When the organic compound is used in an organic electroluminescent device, the glass transition temperature is preferably 90° C. or higher and more preferably 110° C. or higher, from the viewpoint of yielding satisfactory thermal stability of the device. The upper limit of the glass transition temperature is generally about 400° C.

An organic compound according to the present invention generally has a vaporization temperature of 800° C. or lower under normal pressure. When the organic compound is used in an organic electroluminescent device, the vaporization temperature is preferably 700° C. or lower, and more preferably 600° C. or lower, for stably carrying our a film forming process by vapor deposition. The lower limit of the vaporization temperature is generally about 300° C.

An organic compound according to the present invention generally has a melting point of 100° C. or higher. When the organic compound is used in an organic electroluminescent device, the melting point is preferably 150° C. or higher, and more preferably 200° C. or higher, for yielding satisfactory thermal stability of the device. The upper limit of the melting point is generally about 500° C.

[5] Preferred Structure

From the viewpoint of yielding a high triplet excitation level and excellent electrochemical stability, an organic compound according to the present invention represented by Formula (I) preferably has a structure represented by following Formula (III):

[Chemical Formula 19]

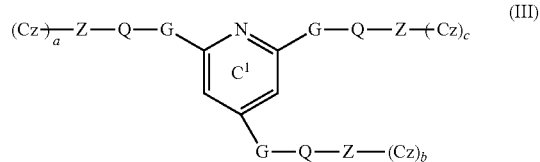

wherein G, Q and Z are each as defined in Formula (I);

Ring $C^1$ represents a pyridine ring and may be substituted at the 3-position and/or the 5-position;

Cz represents a carbazolyl group which may be substituted; and each of "a", "b", and "c" independently represents the number of "Cz"s and independently represents 0 or an integer of from 2 to 5; when at least one of "a", "b", and "c" is 0, there is neither Q nor Z connecting to "Cz" where the at least one of "a", "b", and "c" is 0; plural "Cz"s, when present in one molecule, may be the same as or different from each other.

In Formula (III), G, Q and Z each preferably represents -(Ph)$_p$-, wherein -(Ph)$_p$- is as defined above. This is because, a significant electron donation from a carbazole ring to a pyridine ring may reduce the durability against electric reduction of an organic compound according to the present invention. The total of "p"s in G, Q and Z is preferably 2 or more, and more preferably 4 or less.

Specific examples of Cz are as with those mentioned in $Cz^1$ and $Cz^1$.

Each of "a", "b", and "c" is independently preferably 0, 2, or 4, more preferably 0 or 2, and further preferably 2. This means that the structure of Formula (III) further preferably includes $Cz^1$ and $Cz^2$ alone as Cz.

The smaller the number "b", the better. This is because the introduction of an electron donating group, such as a carbazolyl group, into the 4-position of pyridine Ring $C^1$ may possibly reduce the durability against electric reduction of pyridine Ring $C^1$. The numbers "a" and "c" are preferably small, because the introduction of an electron donating group, such as a carbazolyl group, into the 2- and/or 6-position of pyridine Ring $C^1$ may probably reduce the durability against electric reduction of pyridine Ring $C^1$, although this adverse effect is not so significant as the introduction of an electron donating group, such as a carbazolyl group, into the 4-position of pyridine Ring $C^1$. Accordingly, (a, b, c) are typically preferably (2, 0, 0) or (0, 2, 0).

In addition, the number "a" is preferably equal to the number "c", because, when charged positively or negatively, the molecule preferably has a high symmetry so as to suppress deterioration due to localization of charge. Accordingly, (a, b, c) are especially preferably (2, 0, 2) or (2, 2, 2).

Specific examples of organic compounds having preferred structures are organic compounds represented by following Formulae (IV-1), (IV-2), and (IV-3):

[Chemical formula 20]

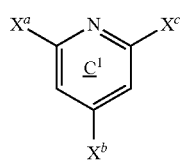

(IV-1)

wherein each of $X^a$ and $X^c$ is independently a monovalent group selected from above-mentioned V-1 to V-34; $X^b$ is a monovalent group selected from following groups W-1 to W-37; and Ring $C^1$ is as defined in Formula (III). In following groups W-27 and W-28, Ph represents a phenyl group.

[Chemical Formula 21]

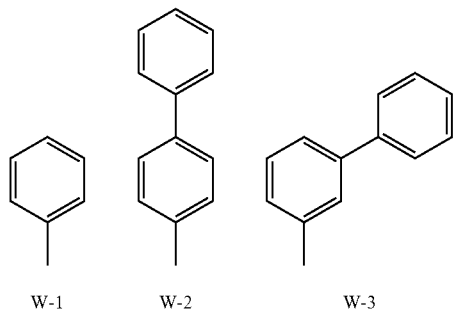

W-1  W-2  W-3

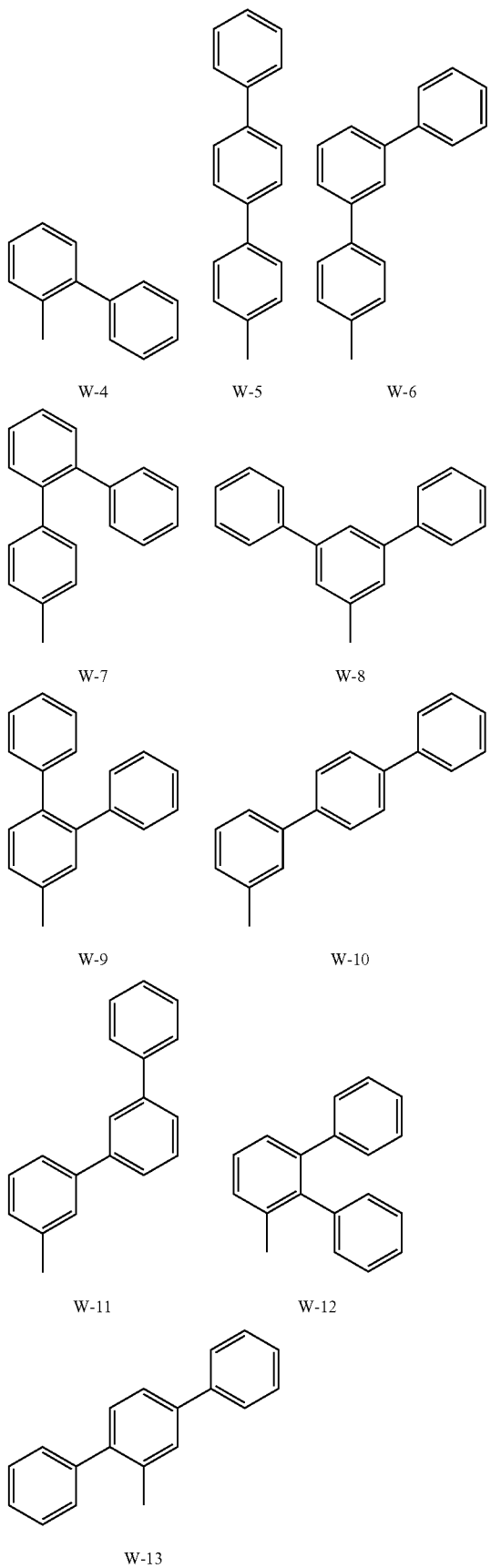

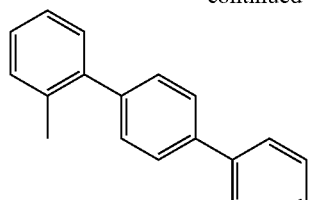
W-14
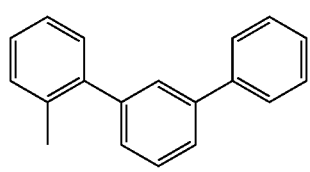
W-15  W-16
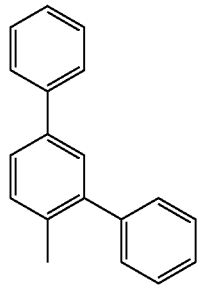
W-17
[Chemical Formula 22]
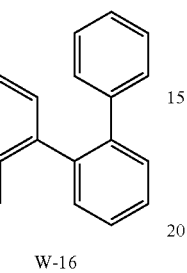
W-18
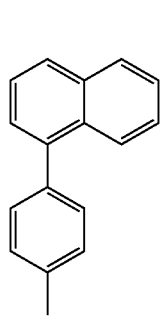 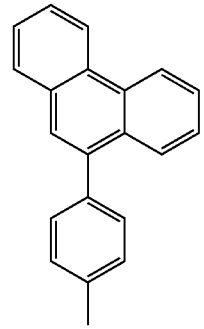
W-19  W-20
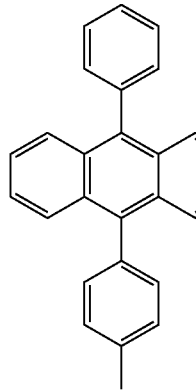 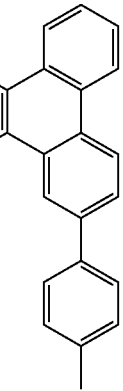
W-21  W-22
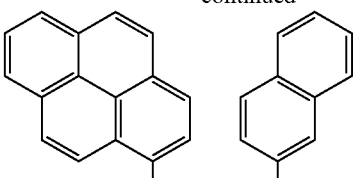
W-23  W-24  W-25
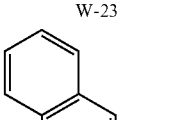 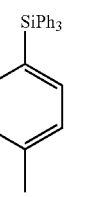 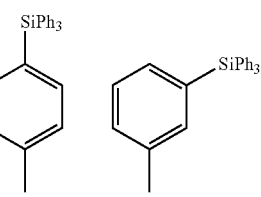
W-26  W-27  W-28
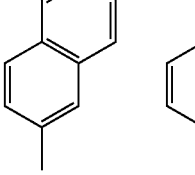
W-29
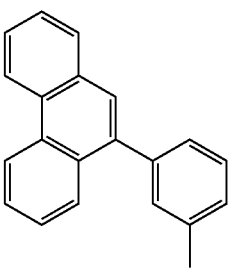
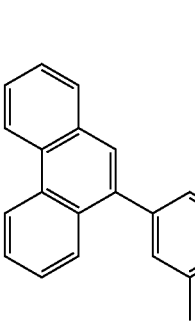 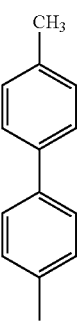
W-30  W-31
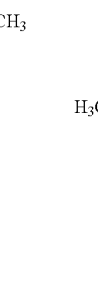 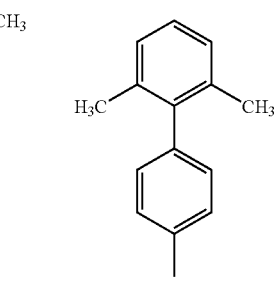
W-32  W-33

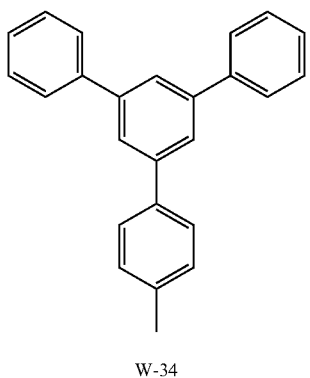

W-34

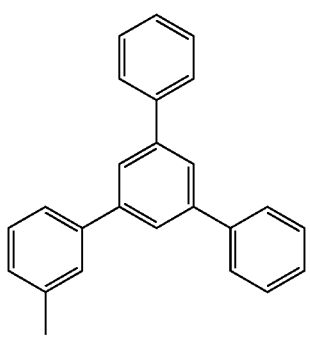

W-35

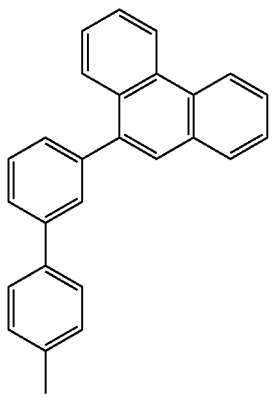

W-36

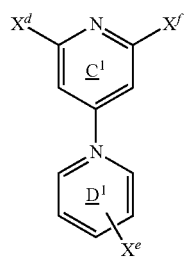

W-37 and W-34 to W-36, and most preferably one of W-2, W-6, W-34, and W-36, from the viewpoint of durability against electric oxidation/reduction.

[Chemical Formula 23]

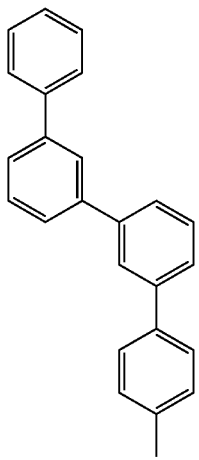

(IV-2)

Wherein each of $X^d$, $X^e$, and $X^f$ is independently a monovalent group selected from above-mentioned V-1 to V-34; Ring $C^1$ is as defined in Formula (III); and Ring $D^1$ is a phenylene linkage group connecting between Ring $C^1$ and $X^e$.

In Formula (IV-2), each of $X^d$, $X^e$, and $X^f$ is independently preferably one of V-1 to V-6, V-8, V-9, V-12, V-13, V-16 to V-22, V-24, V-27, and V-28, more preferably one of V-1, V-2, V-3, V-5, V-6, and V-12, and most preferably one of V-1, V-2, and V-5, from the viewpoint of durability against electric oxidation/reduction. Provided that the bonding position with Ring $C^1$ is defined as the 1-position of Ring $D^1$, $X^e$ can be bound with Ring $D^1$ at any one of the 2-, 3-, 4-, 5-, and 6-positions. From the viewpoint of durability against electric oxidation/reduction, $X^e$ is preferably bound at the 3-, 4-, or 5-position and more preferably bound at the 4-position of Ring $D^1$.

[Chemical formula 24]

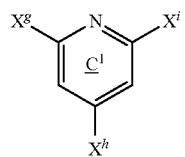

(IV-3)

Wherein each of $X^g$, $X^h$, and $X^i$ is independently a monovalent group selected from above-mentioned V-1 to V-34; and Ring $C^1$ is as defined in Formula (III).

In Formula (IV-3), each of $X^g$, $X^h$, and $X^i$ is independently preferably one of V-1, V-2, V-4 to V-15, V-17 to V-21, V-27, V-28, and V-31 to V-33, more preferably one of V-1, V-6 to V-9, V-11 to V-15, 31, and V-32, and most preferably one of V-1, V-7 to V-9, and V-13 to V-15, from the viewpoint of durability against electric oxidation/reduction.

[6] Specific Examples

Specific examples of preferred compounds as organic compounds according to the present invention will be illustrated below, which, however, by no means limit the scope of she present invention. In the following structural formulae as examples, —N-Cz represents a N-carbazolyl group:

In Formula (IV-1), each of $X^a$ and $X^c$ is independently more preferably one of V-1, V-2, V-4 to V-15, V-17 to V-21, V-27, V-28, and V-31 to V-33, further preferably one of V-1, V-6 to V-9, V-11 to V-15, V-31, and V-32, and most preferably one of V-1, V-7 to V-9, V-13 to V-15, for yielding durability against electric oxidation/reduction and a high triplet excitation energy. $X^b$ is preferably one of W-1 to W-3, W-6, W-8, W-10, W-11, W-20, W-29, W-31, W-32, W-34 to W-37, more preferably one of W-1 to W-3, W-6, W-8, W-11, W-31, W-32,

[Chemical Formula 25]
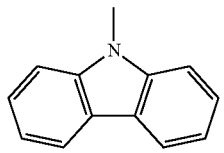
[Chemical Formula 26]
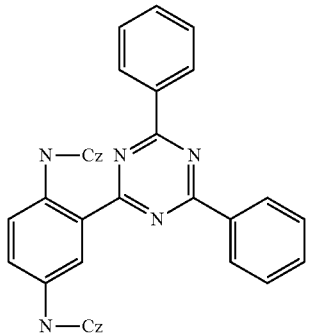 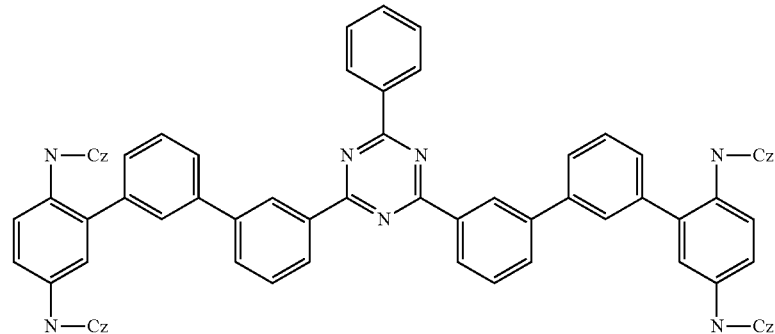
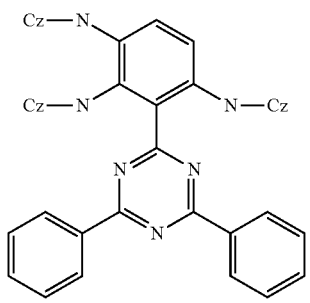 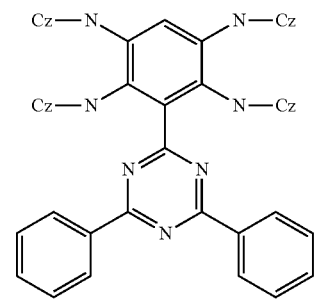 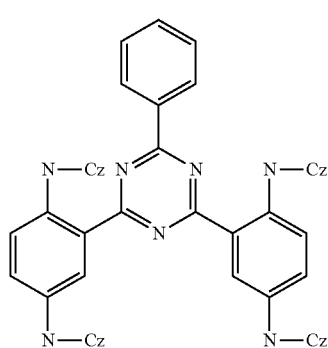
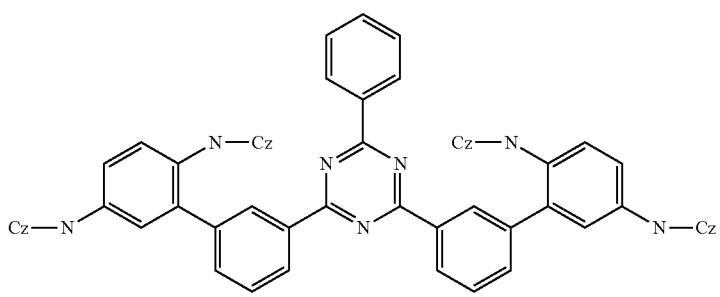
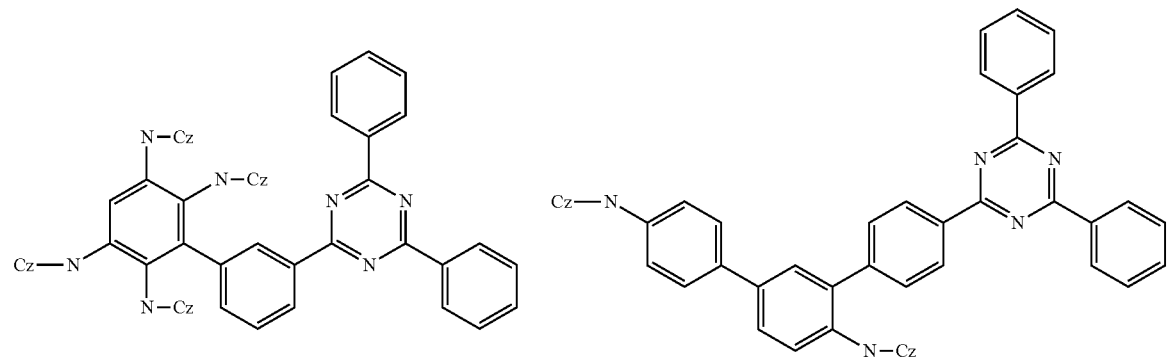

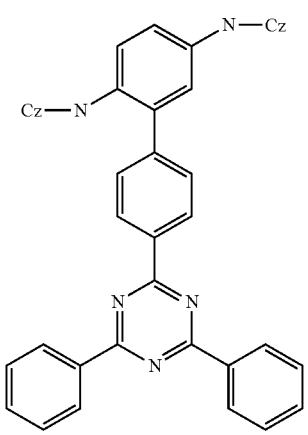
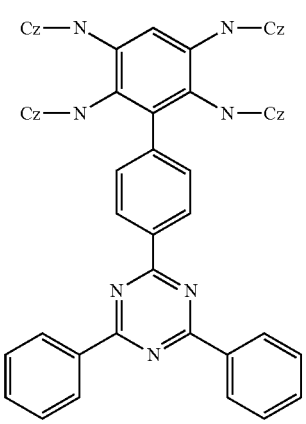
[Chemical Formula 27]
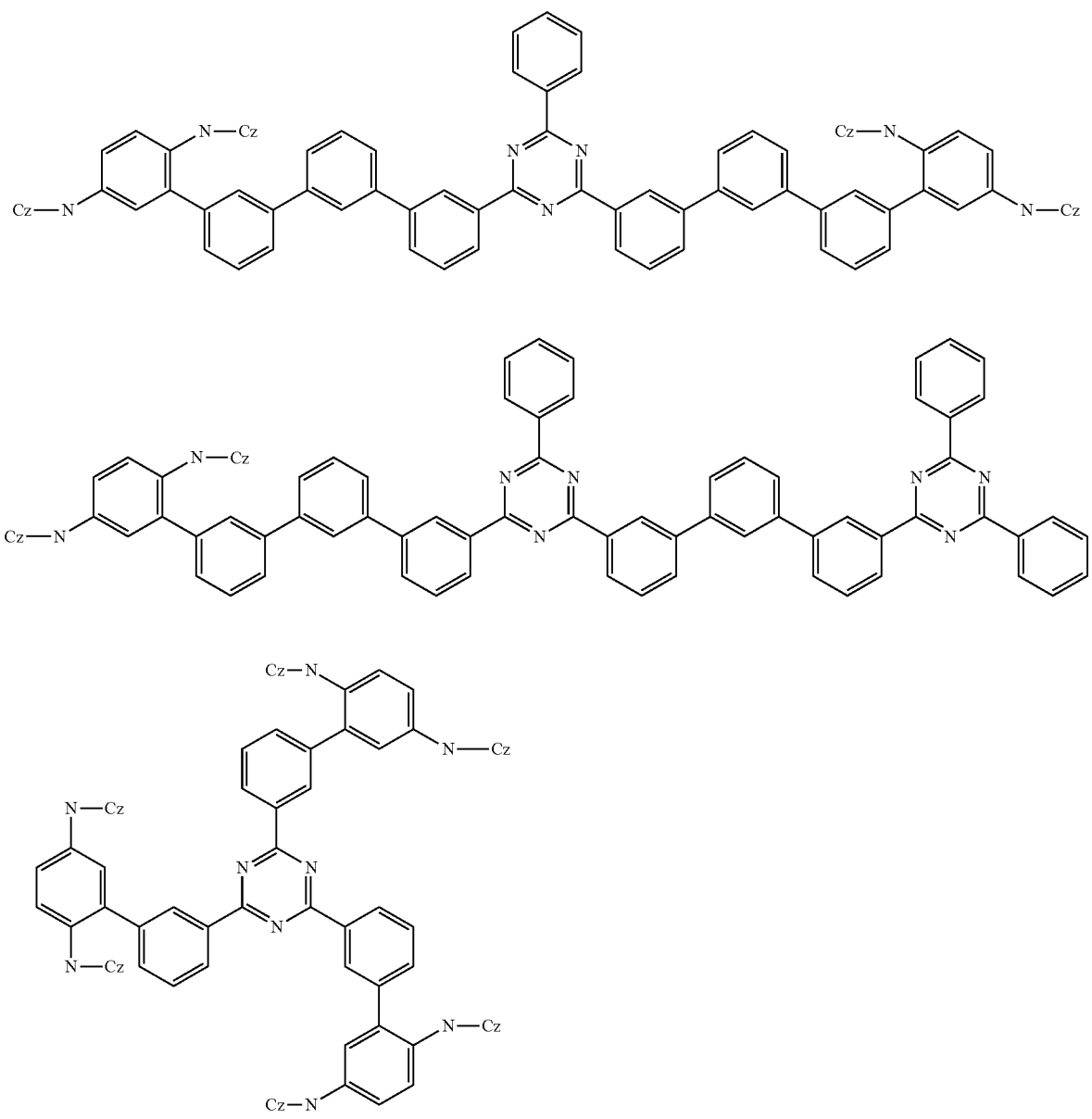

-continued
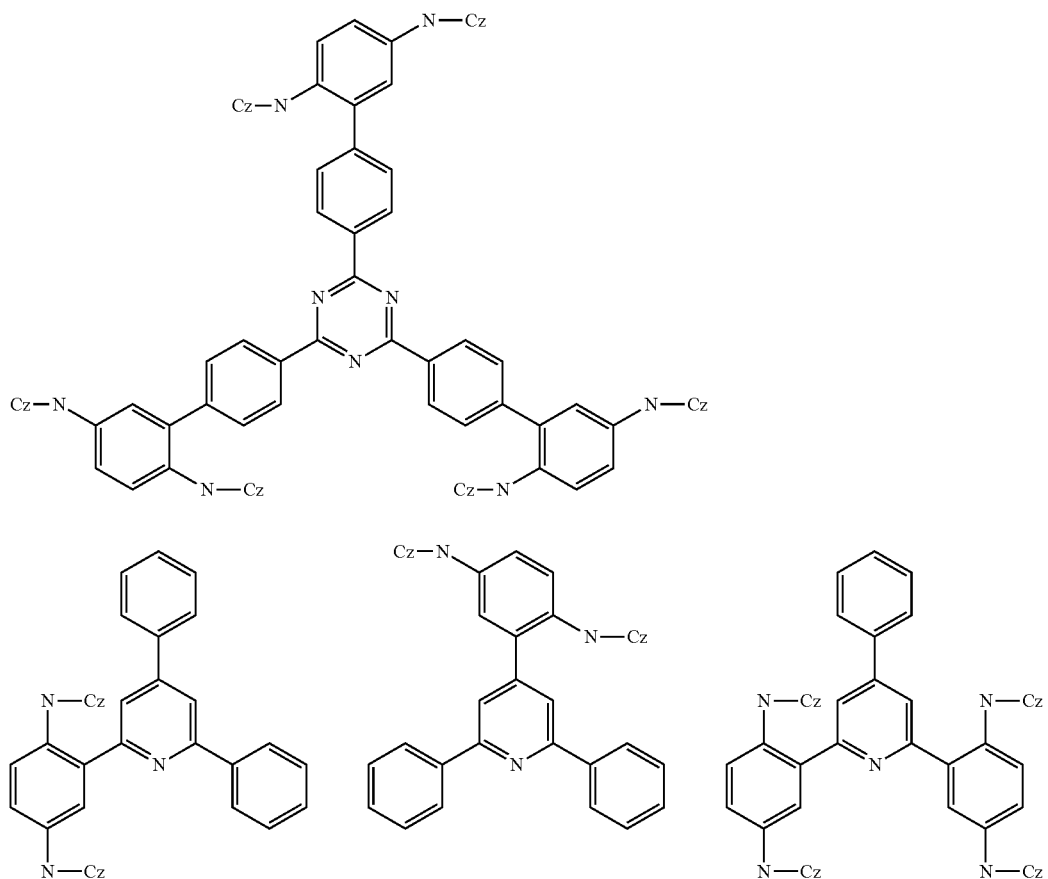
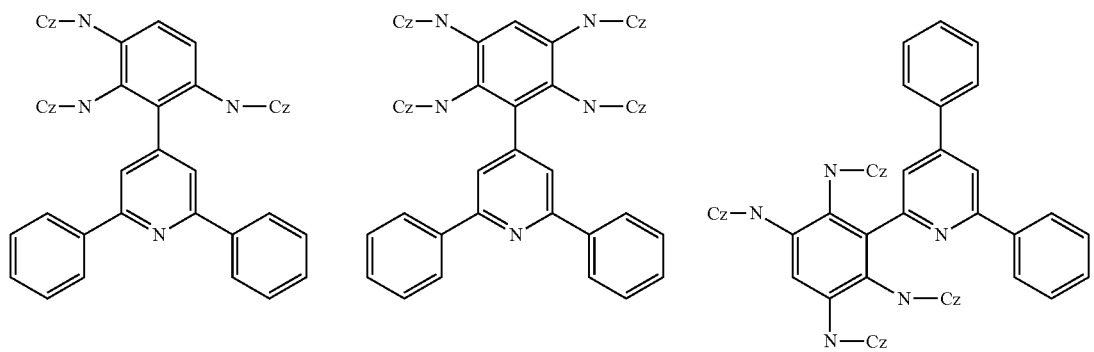
[Chemical Formula 28]
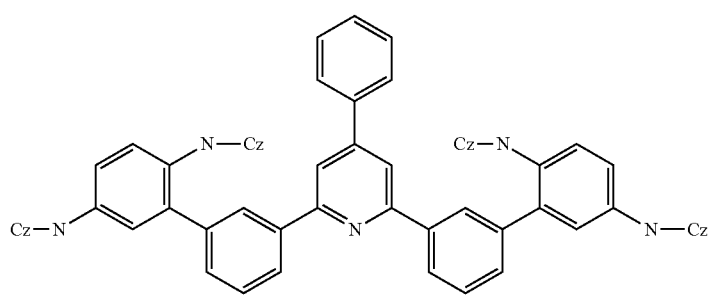

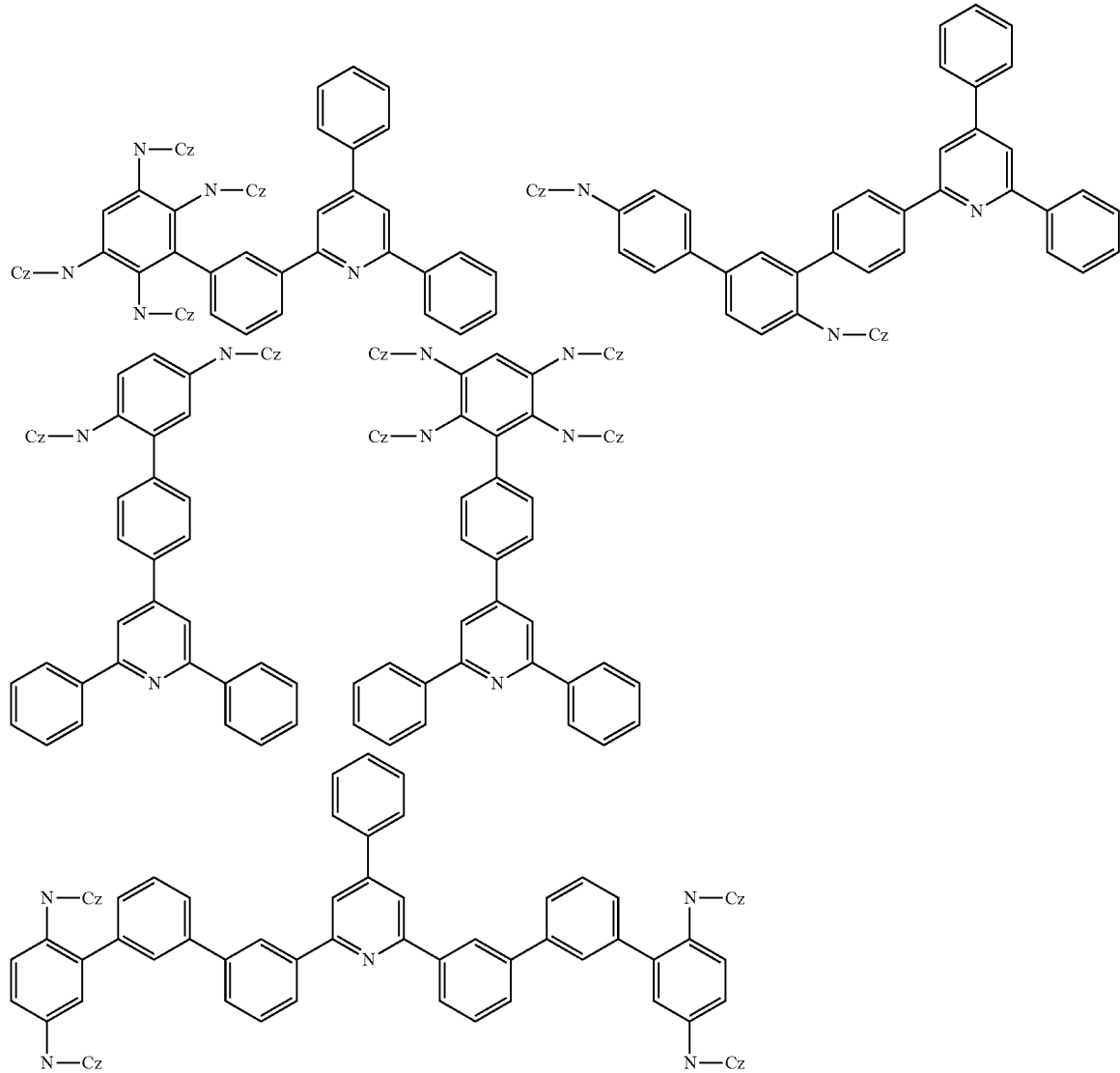
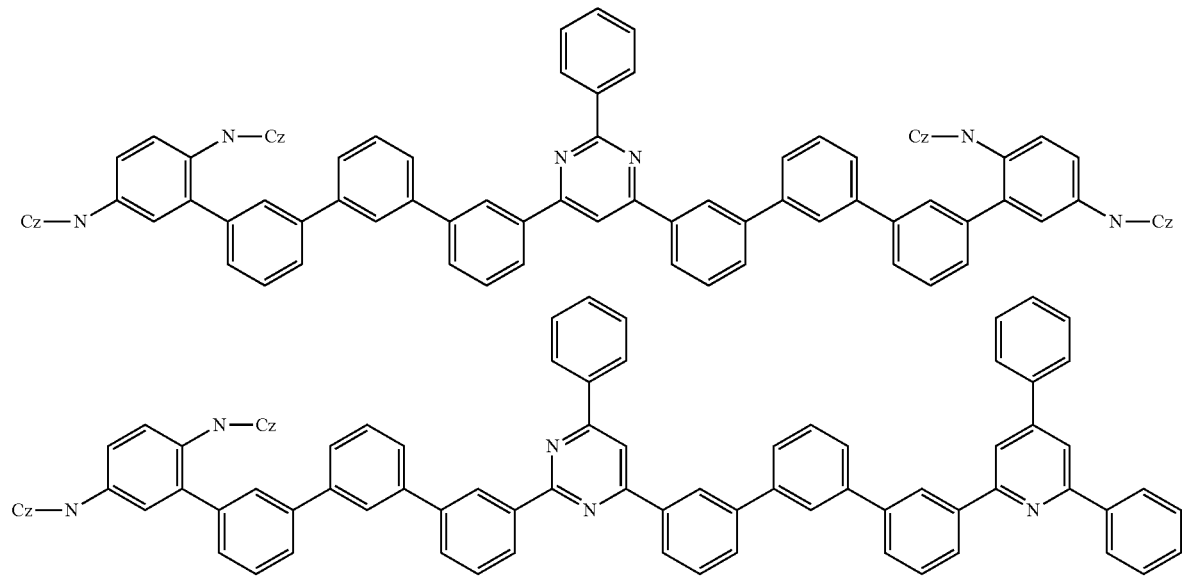

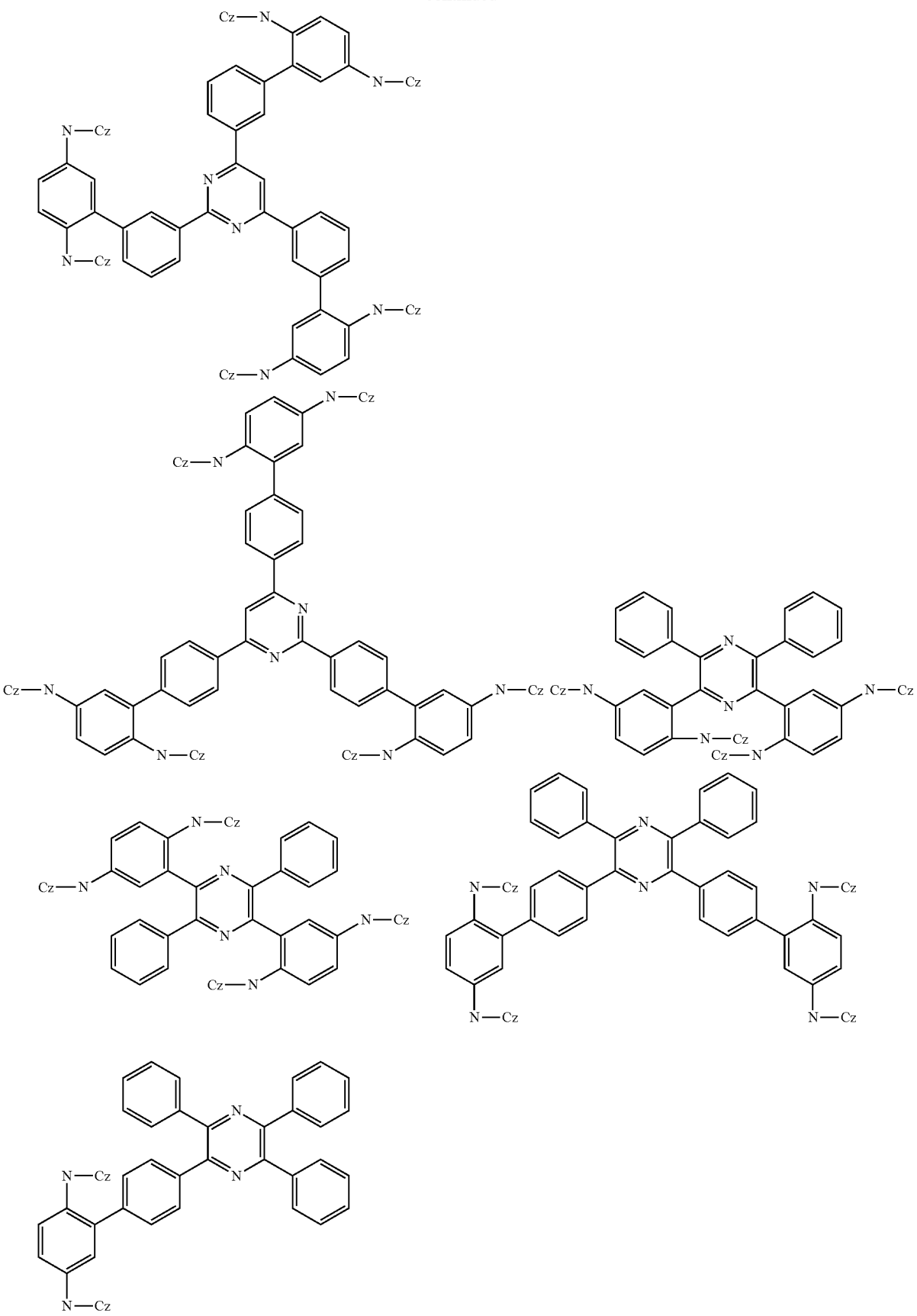

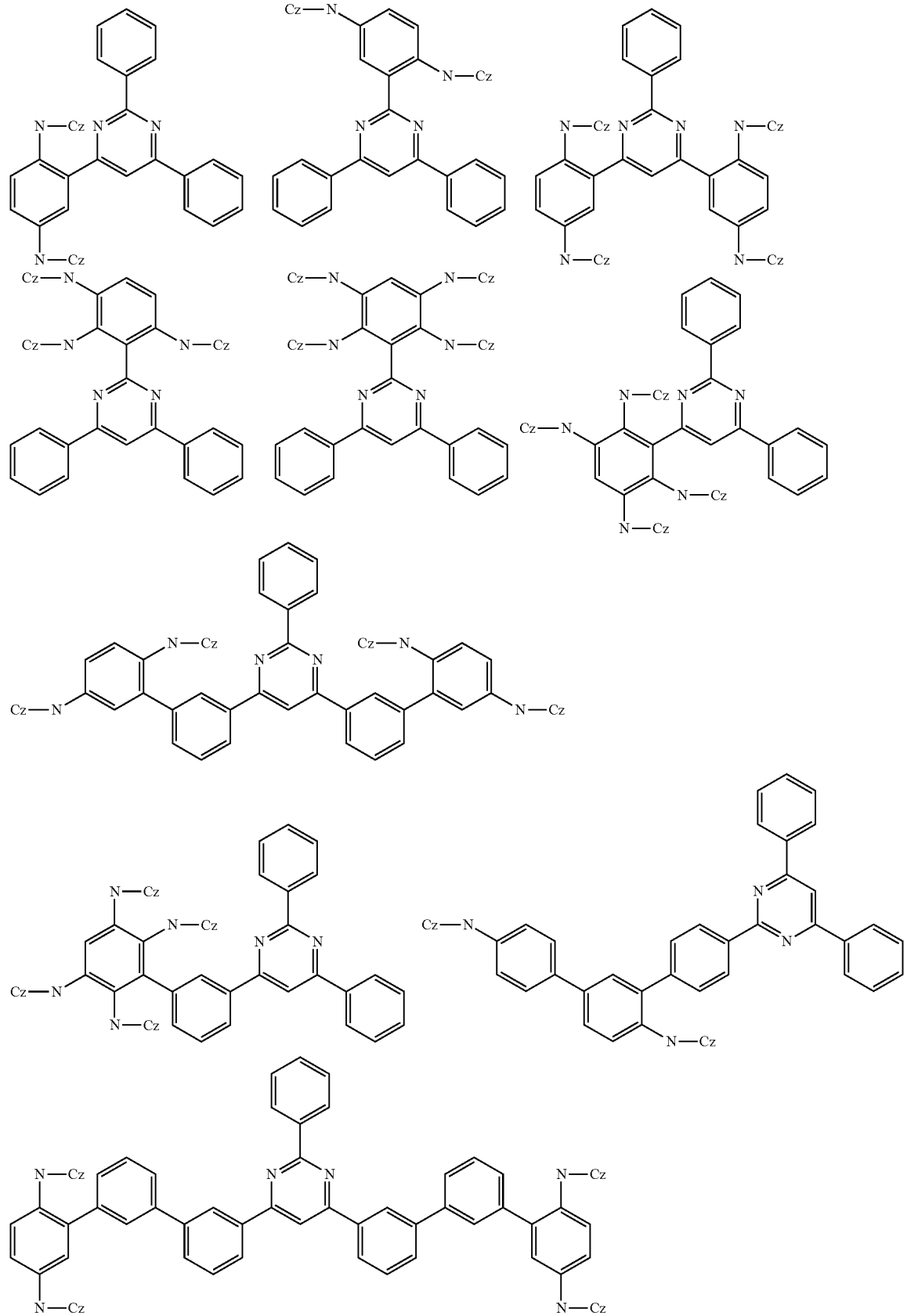
[Chemical Formula 30]

-continued
[Chemical Formula 31]
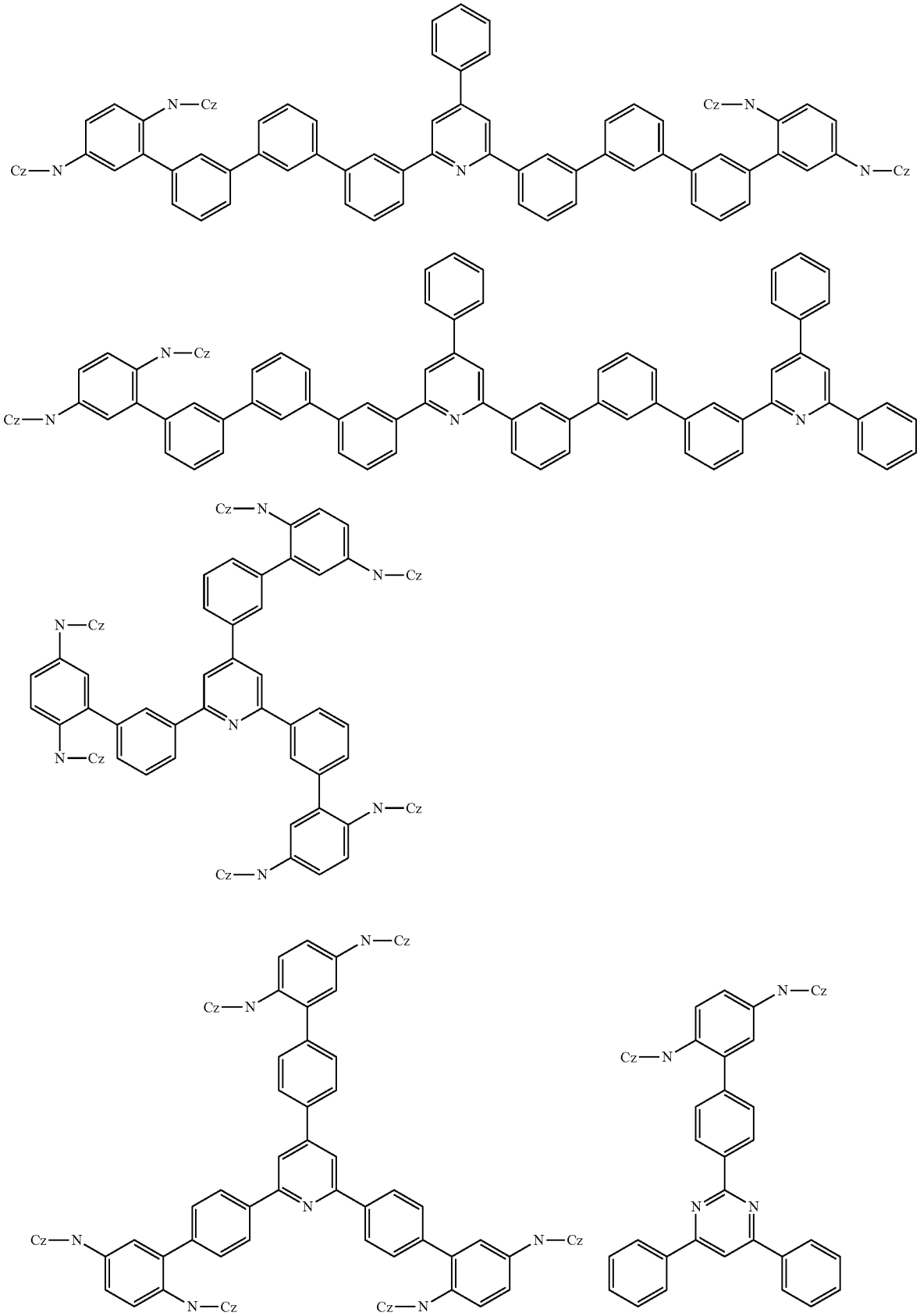

-continued
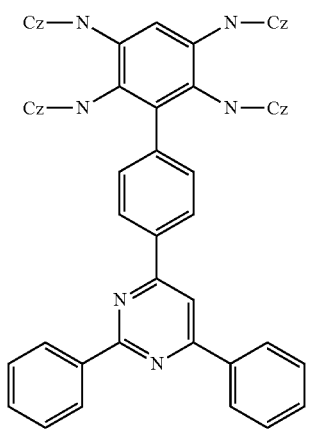
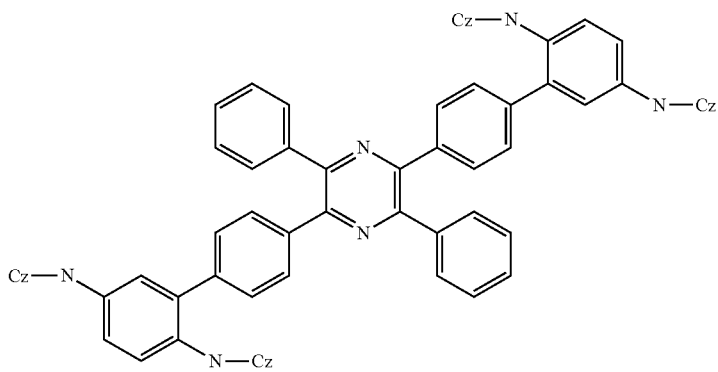
[Chemical Formula 32]
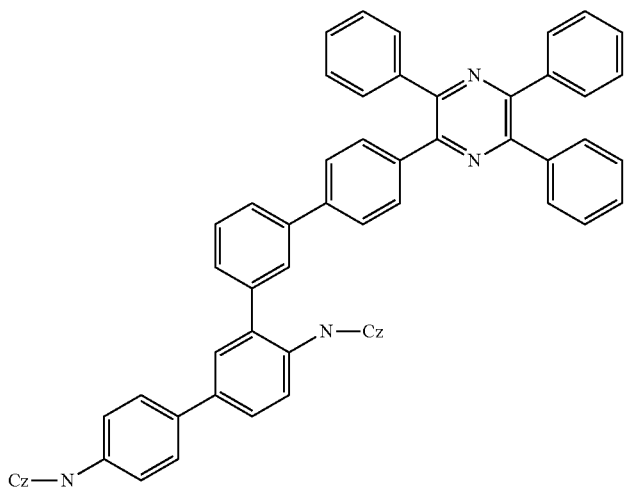
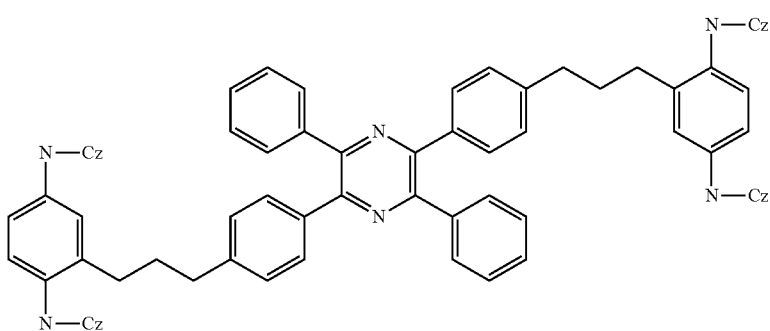

[Chemical Formula 33]
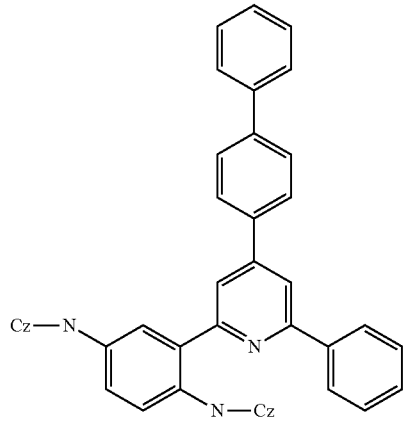
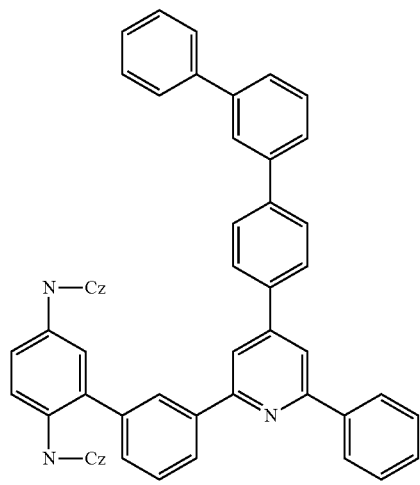
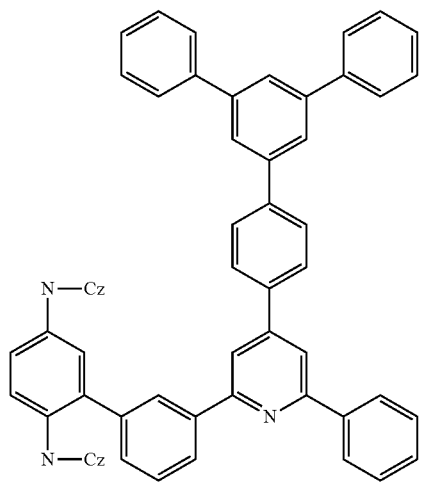
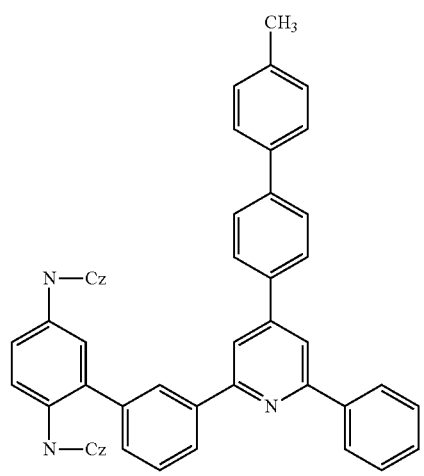
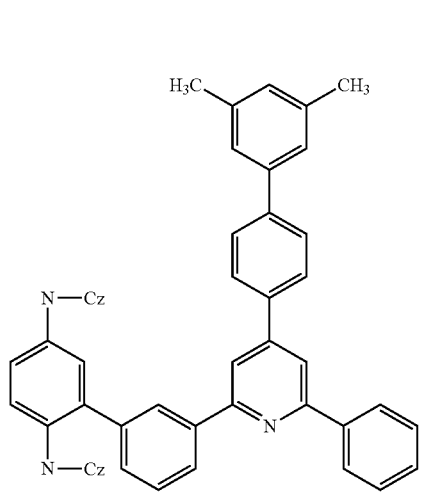
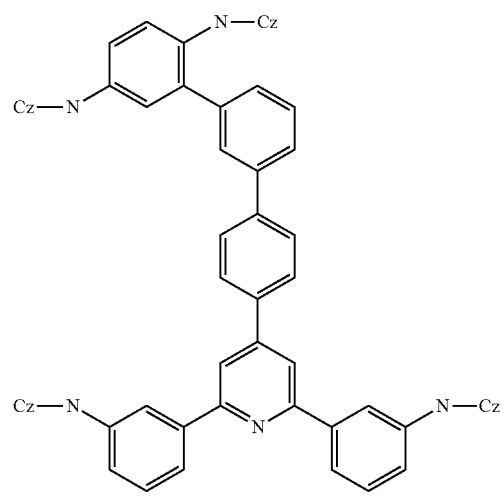

-continued
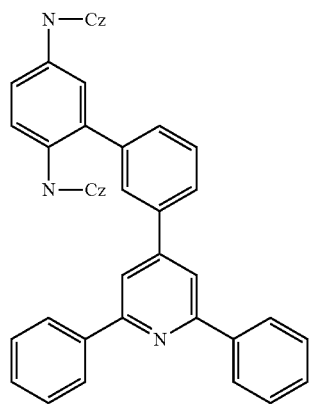
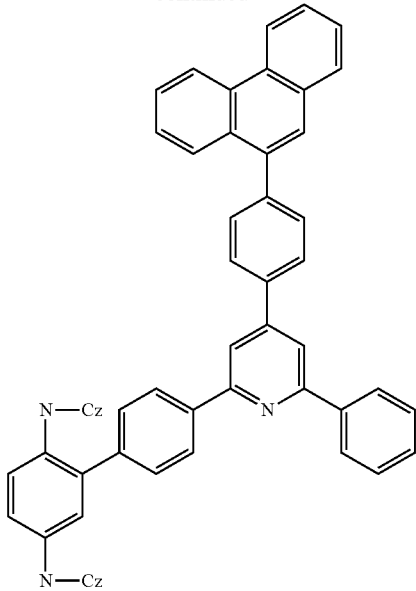
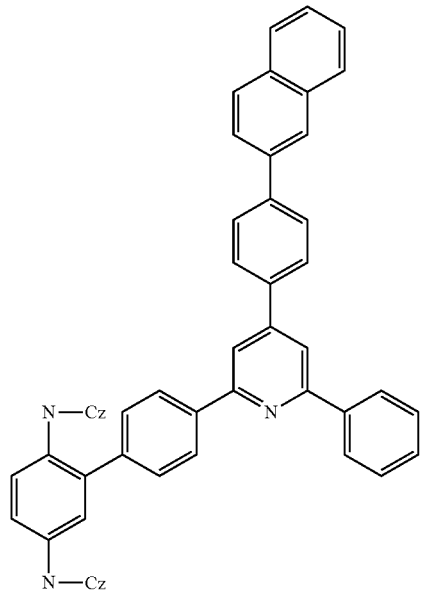
[Chemical Formula 34]
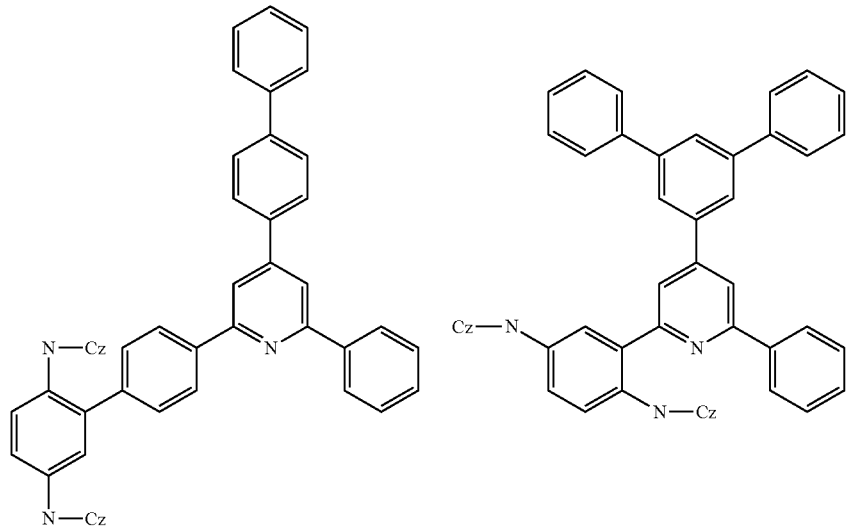

-continued
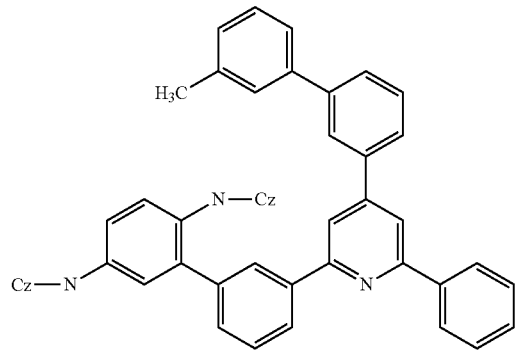
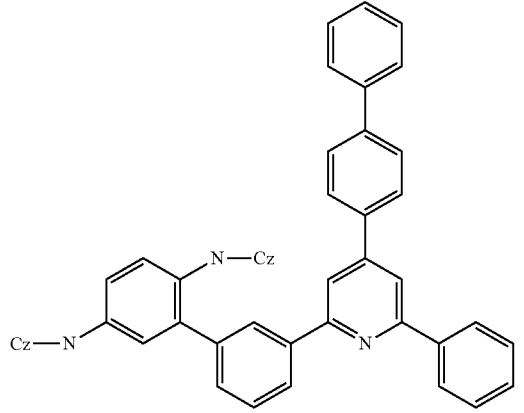
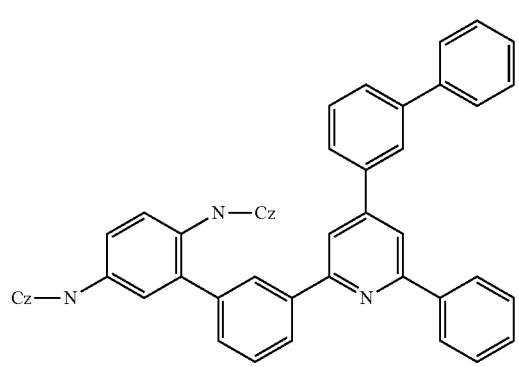
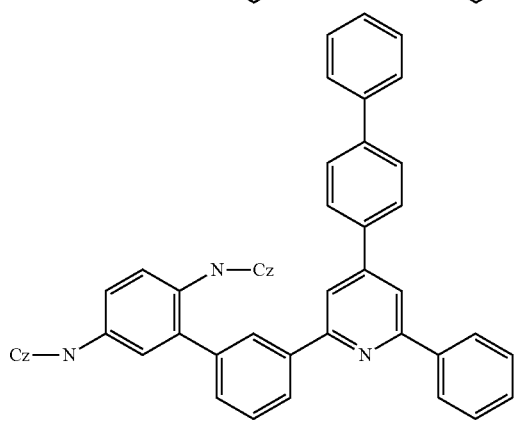
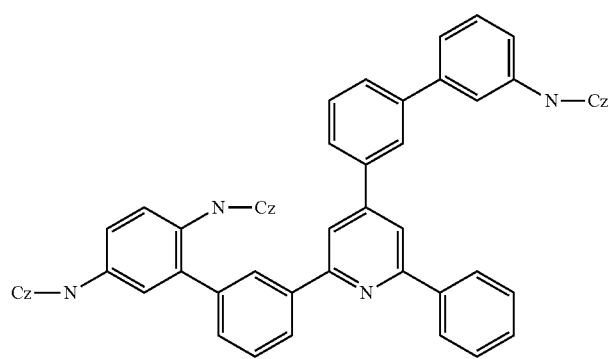
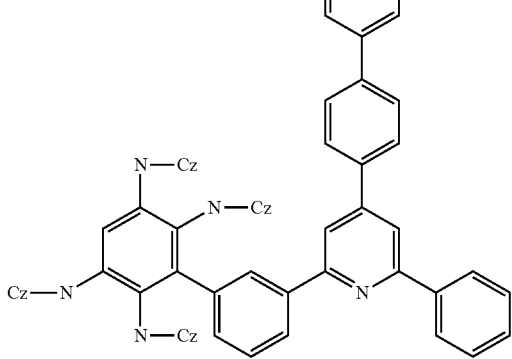
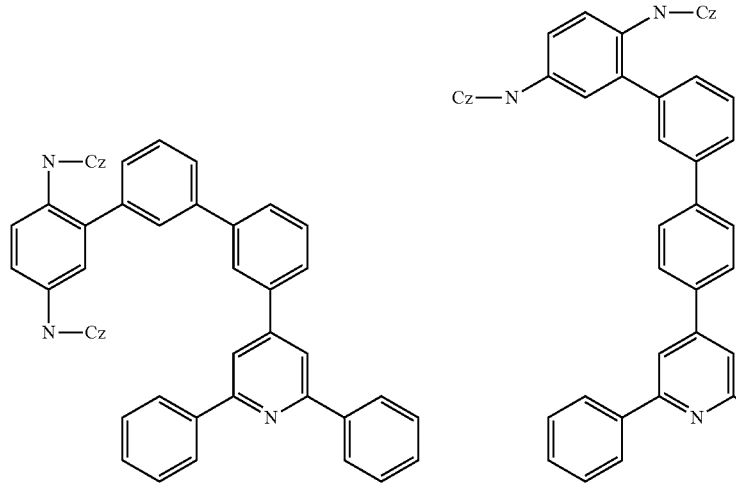

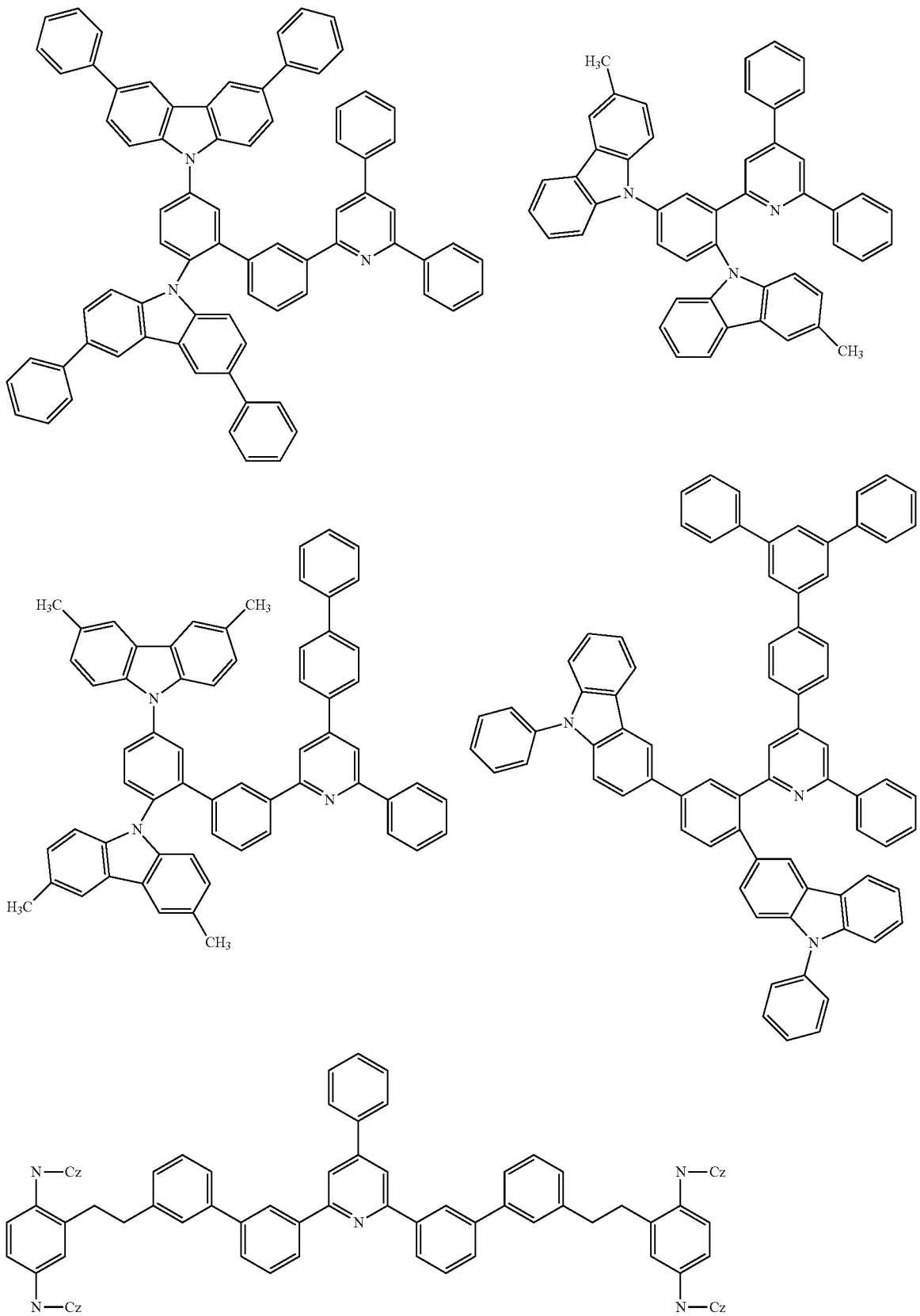

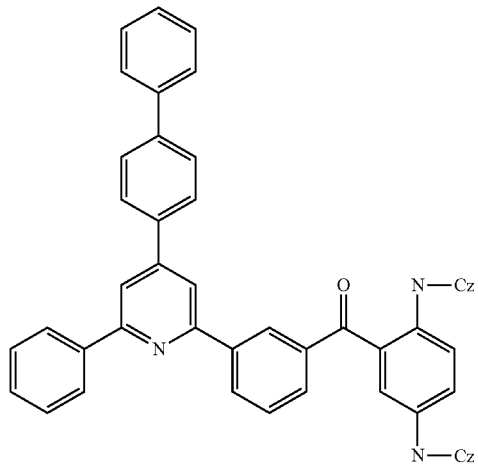

[7] Preparation Method

Each of organic compounds according to the present invention can be synthetically prepared according to a known procedure while selecting starting materials according to the structure of a target compound.

(1) A pyridine ring can be introduced according to the following process (1-A), (1-B), or (1-C):

(1-A) When $R^0$—(CHO), wherein $R^0$ represents an arbitrary substituent or a linkage group, is used as a starting material, the following process (A1), (A2), (A3), (A4), or (A5), for example, can be employed.

(A1): A process as disclosed typically in Angew. Chem. Int. Ed. Engl. (1962) 1, 626; Synthesis (1976), 1-24; J. Heterocyclic Chem. (1977) 14, 147; Collect. Czech. Chem. Commun. 57 (1992) 2, 385-392; and CS-262585. According to this process, an intermediate (—CH═CR—CO—) is prepared by stirring 1 equivalent of an aldehyde and 0.5 to 2 equivalents of an acetylide in the presence of a strong acid such as sulfuric acid in a solvent at room temperature for one to ten hours, or by stirring the starting materials in the presence of a strong base such as sodium hydroxide in an alcohol and/or aqueous solvent with heating for one to ten hours. The former solvent can be, for example, acetic acid, an alcohol, nitrobenzene, toluene, chlorobenzene, dichlorobenzene, or cyclohexane, or a mixture of these solvents. The intermediate is reacted with heating with an acylpyridinium salt and ammonium acetate in acetic acid as a solvent in the presence of oxygen to yield a target compound. In the following formula, X represents a halogen atom such as Br or I.

[Chemical Formula 36]

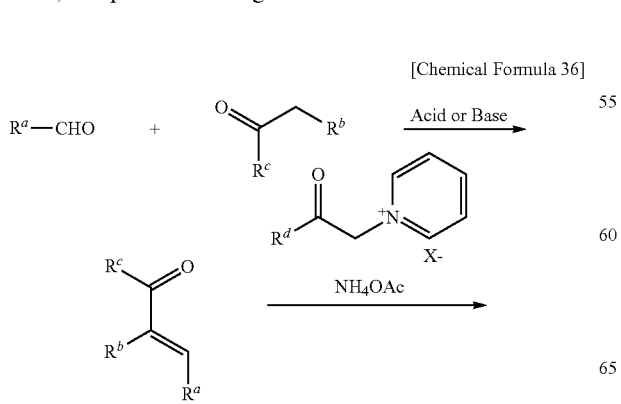

(A2): A process as disclosed In Liebigs Ann. Chem. (1974), 1415-1422; J. Org. Chem. 38, (2002) 6, 830-832; and Japanese Unexamined Patent Application Publication No. 2000-186066. According to this process, an aldehyde is reacted with an acetylide with heating in the presence of an oxidizing agent, such as boron trifluoride or perchloric acid, in toluene as a solvent to yield a pyrylium salt, and the pyrylium salt is reacted with ammonia in water or an alcohol as a solvent.

[Chemical Formula 37]

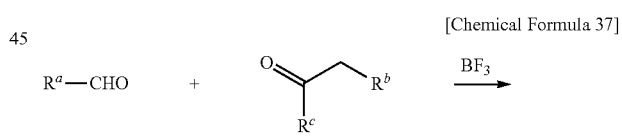

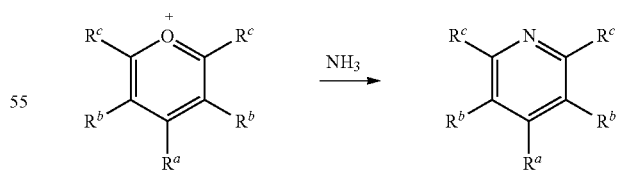

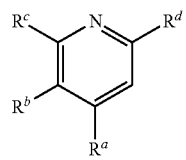

(A3): A process as disclosed typically in J. Am. Chem. Soc. (1952) 74, 200. According to this process, a target compound is synthetically prepared in one step from ammonium acetate, an aldehyde, and an acetylide with heating in a solvent. The solvent herein includes, for example, acetic acid, an alcohol, nitrobenzene, toluene, chlorobenzene, dichlorobenzene, cyclohexane, and mixture of these solvents.

[Chemical Formula 38]

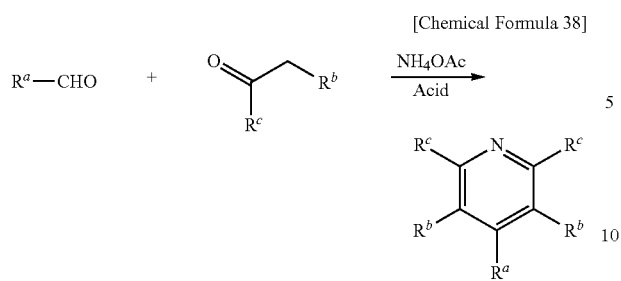

(A4): A process as disclosed typically in Chem. Commun. (Cambridge) (2000) 22, 2199-2200. According to this process, a target compound is synthetically prepared by grinding an aldehyde with 2 equivalents of an acetylide in a mortar at room temperature in the presence of a strong base such as sodium hydroxide in the absence of a solvent to yield an intermediate (diketone), and the intermediate is reacted with ammonium acetate with heating in a solvent. The solvent herein includes, for example, acetic acid, an alcohol, nitrobenzene, toluene, chlorobenzene, dichlorobenzene, cyclohexane, and mixtures of these solvents.

[Chemical Formula 39]

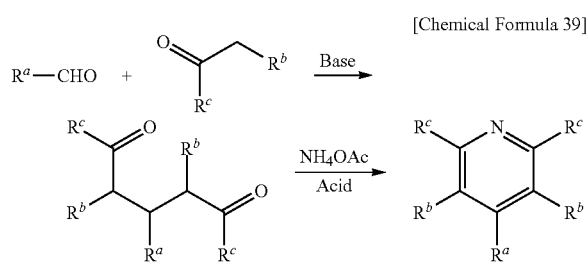

(A5): A process as disclosed typically in J. Org. Chem. (1988), 53, 5960. According to this process, a target compound is synthetically prepared in one step from an aldehyde and ethylidenevinylamine.

[Chemical Formula 40]

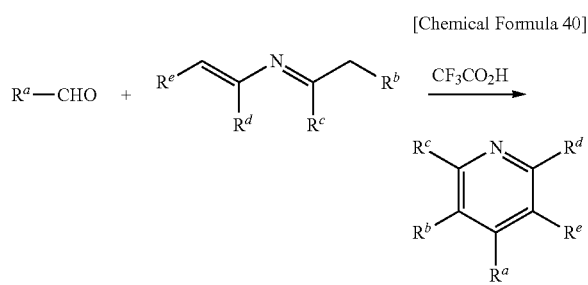

(1-B) When a pyridine ring substituted with a halogen atom, such as chlorine, bromine, or iodine, on at least one of the 2-, 4-, and 6-positions is used as a starting material, the halogen element can be converted into an arbitrary substituent.

The conversion can be carried out, for example, by a process as disclosed typically in Org. Lett. 3 (2001) 26, 4263-4265. According to this process, a target compound is synthetically prepared by reacting the pyridine ring with zinc bromide and a boronic acid with heating in the presence of a palladium catalyst. In the following formula, "dba" represents dibenzylideneacetone.

[Chemical Formula 41]

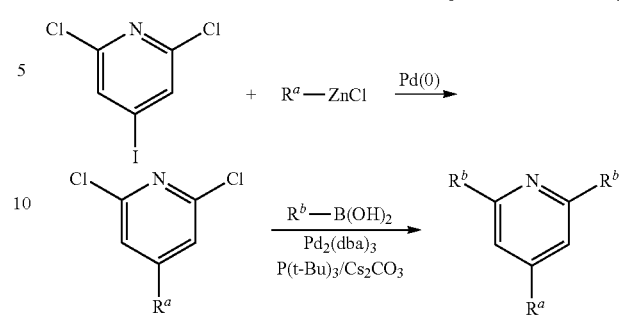

(1-C) In addition, any procedures can be arbitrarily applied to the Introduction of substituents and the formation of linkage group G or Z, according to necessity. For example, following processes (C1), (C2), and (C3) can be employed.

(C1): A process of carrying out synthesis by preparing a pyridine derivative having aromatic cyclic groups at the 2- and 6-positions using paraformaldehyde and an aromatic acyl compound as an aldehyde and an acetylide, respectively; halogenating the 4-position of the pyridine ring of this derivative using a halogenating agent such as N-bromosuccinimide to yield a halogenated derivative; separately converting the halogen atom of the halogen derivative into —B(OH)$_2$ group, —ZnCl group, or —MgBr group; and carrying out a coupling reaction between the converted derivative with the halogenated derivative;

(C2): a process of lithiating the halogenated derivative typically with n-butyllithium; treating the lithiated derivative with N,N-dimethylformamide to yield a pyridine derivative having aromatic cyclic groups at the 2- and 6-positions and —CHO group at the 4-position; and reacting the pyridine derivative with an acetylide to form a second pyridine ring;

(C3): a process of carrying out synthesis by stirring 2,6-dichloro-4-iodopyridine, listed as a starring material in Process (1-B), in the presence of a base by she catalysis of a copper catalyst such as copper powder with heating at 150° C. to 250° C. to yield 2,6,2',6'-tetrachloro-[4,4']bipyridyl, and treating this compound by the procedure of Process (B).

The aldehyde (R$^a$—CHO) for use in the above preparation processes can be obtained as a generally available reagent, but where necessary, the aldehyde can be easily obtained by synthetic preparation according typically to one of following Processes (i) to (xiii):

(i) a process of reacting a halide (R$^a$—X) or a hydrocarbon compound having an active hydrogen atom (R$^a$—H) with an alkyllithium or a strong base, and treating this with N,N-dimethylformamide. The alkyllithium includes, for example, butyllithium, and the strong base includes, for example, sodium hydride, triethylamine, tert-butoxypotassium, and sodium hydroxide, of which alkyllithiums such as butyllithium are preferred (Organic & Biomolecular Chemistry (2003) 1, 7, 1157-1170; Tetrahedron Lett, 42(2001) 37, 6589-6592);

(ii) a process in which —CO$_2$R group, wherein R is a hydrogen atom, a chlorine atom, an alkyl group, an aromatic cyclic group, or an amino group, is reduced typically with lithium aluminum hydride or sodium borohydride no yield an alcohol, and the alcohol is oxidized typically with pyridinium chlorochromate, manganese dioxide, iodoxybenzoic acid, peroxydisulfate, or 2,3-dichloro-5,6-dicyano-1,4-benzoquinone to convert into —CHO (J. Med. Chem. (1990) 33, 2408-2412; Angew. Chem., Int. Ed. 40 (2001) 23, 4395-4397;

J. Am. Chem. Soc. (2002) 124, 10, 2245-58; J. Am. Chem. Soc. (1993) 115, 9, 3752-3759; J. Chem. Res., Synop. (2001) 7, 274-276; Synthesis (2001) 15, 2273-2276; Bull. Korean Chem. Soc. 20 (1999) 11, 1373-1374; Arzneim. Forsch. 47 (1997) 1, 13-18; J. Org. Chem. 63 (1998) 16, 5658-5661; J. Chem. Soc. Sec. C; Organic (1968) 6, 630-632);

(iii) a process of reducing a —$CO_2R$ group, wherein R is a hydrogen atom, a chlorine atom, an alkyl group, an aromatic cyclic group, or an amino group, typically with a lithium tris(dialkylamino)aluminum hydride or a sodium tris(dialkylamino)aluminum hydride to convert into —CHO in one step (Bull. Korean Chem. Soc., 13 (1992) 6, 670-676; Bull. Korean Chem. Soc., 12 (1991) 1, 7-8; and Org. Prep. Proced. Int. 24 (1992) 3, 335-337);

(iv) a process of converting a —$CO_2R$ group, wherein R is a hydrogen atom, a chlorine atom, an alkyl group, an aromatic cyclic group, or an amino group, in the presence of hydrogen and a palladium catalyst to convert into —CHO in one step (Chem. Ber. (1959) 92, 2532-2542; PCT International Publication Number WO 00/12457; and Bull. Chem. Soc. Jpn. (2001) 74, 1803-1815);

(v) a process of reducing a —CN group typically with a lithium tris(dialkylamino)aluminum hydride to convert into —CHO in one step (Bull. Korean Chem. Soc., 13 (1992) 6, 670-676);

(vi) a process of allowing, for example, o-iodylbenzoic acid, Dess-Martin periodinane, or acetoxyiodosylbenzoic acid to act on an Ar—$CH_3$ group, wherein Ar is an aromatic cyclic group, to directly convert into Ar—CHO (J. Am. Chem. Soc. (2002) 124, 10, 2245-58);

(vii) a process of converting an Ar—$CH_3$ group, wherein Ar is an aromatic cyclic group, via Ar—$CH_2Br$ and Ar—$CH_2OCH_3COO$ into Ar—$CH_2OH$, and oxidizing Ar—$CH_2OH$ typically with pyridinium chlorochromate, manganese dioxide, or iodoxybenzoic acid to convert into —CHO (J. Org. Chem. (1993) 58, 3582-3585);

(viii) a process of allowing a Vilsmeier reagent to act on an 1-ethyl-1-arylallyl alcohol to yield an arylcarboxyaldehyde (Indian Journal of Chemistry (1988) 27B, 213-216);

(ix) a process of allowing a Vilsmeier reagent to act on a 1,4-cyclohexadiene to yield an arylcarboxyaldehyde (Synthesis (1987), 197-199; and Synthesis (1985), 779-781);

(x) a process of brominating an Ar—$CH_3$ group, wherein Ar is an aromatic cyclic group, typically with bromine or N-bromosuccinimide to convert into Ar—$CH_2Br$, and treating this with a 2-nitropropane carbanion reagent or hexamethylenetetramine to convert into Ar—CHO (Collect. Czech. Chem. Commun. (1996) 61, 1464-1472; Chem. Eur. J. (1996) 2, 12, 1585-1595; and J. Chem. Research (S), (1999) 210-211);

(xi) a process of yielding an arylaldehyde, such as 1,3,5-triformylbenzene, from a polymethinium salt such as a heptamethinium salt (Collect. Czech. Chem. Commun. (1965) 30, 53-60);

(xii) a process of yielding 1,3,5-triformylbenzene by self-condensation of triformylmethane (Collect. Czech. Chem. Commun. (1962) 27, 2464-2467); and (xiii) a process of converting an Ar—$CHBr_2$ group, wherein Ar is an aromatic cyclic group, into Ar—CHO using a dialkylamine (Bulletin die La Societe Chmique De France (1966) 9, 2966-2971).

The ketone ($R^c$—CO—$CH_2$—$R^b$) for use in the preparation processes can be obtained as a generally available reagent, but can also be easily synthetically prepared, for example, according to one of the following processes:

a process of treating a $R^c$—$CO_2R$ group, wherein R is a hydrogen atom, a chlorine atom, an alkyl group, an aromatic cyclic group, or an amino group, with an alkylating agent, such as an alkyllithium, dimethylsulfuric acid, or dimethyl sulfoxide, to convert into $R^c$—CO—$CH_2R^b$ (J. Am. Chem. Soc. (1959), 81, 935-939; J. Am. Chem. Soc. (1961) 83, 4668-; Tetrahedron Lett. (1967) 1073-; J. Chem. Soc. (1960) 360-; J. Chem. Soc., Perkin Trans. 1 (1977) 680; and JP 5-5062039); and a process of carrying out synthesis by acting an acylating agent, such as an acid chloride, in the presence of a Lewis acid catalyst such as aluminum chloride (very popular Friedel-Crafts reaction).

Other preparation processes usable herein are preparation processes described or cited in "Heterokan No Kagaku-Iyakuhin No Kiso (in Japanese; Heterocyclic Chemistry-Foundation of Pharmaceutical Drugs" (2002, Kunieda, et al., Kagaku-Dojin Publishing Company, Inc.); "Heterocyclic Chemistry" (4th ed., 2000, J. A. Joule and K. Mills, Blackwell Science Co.); "Heterocyclic Compounds, New Edition, Foundation and Application" (2004, Hiroshi Yamanaka et al., Kodansha Ltd.); and "Vollhardt & Schore, Organic Chemistry, Last Volume" (2004, K. P. C. Vollhardt, Kagaku-Dojin Publishing Company, Inc.).

(2) A pyrazine ring can be introduced, for example, according to one of following processes (2-a), (2-b), (2-c), (2-d), (2-e), (2-f), and (2-g):

(2-a) a process of synthetically preparing a benzoin intermediate from one aromatic aldehyde or two or more different aromatic aldehydes (Khim.-Farm. Zh. 25 (1991) 4, 28-31; Helvetica Chimica Acta (1985) 68 (3), 592-599; J. Chem. Res. Synop. (2002) 6, 262-263; Ser C. (1996б) 263, 1156-; J. Am. Chem. Soc. (2002) 124, 12084-12085; Advanced Synthesis & Catalysis (2002) 344, 96-103; PCT Int. Appl., 2002002753, 10 Jan. 2002; J. Org. Chem. (2001) 66, 8010-8014; J. Chem. Soc., Perkin Trans. 1, (2001) 7, 633-635; Tetrahedron Lett. (2000) 41, 10159-10162; J. Org. Chem. (1983) 48, 459-464; and Journal fuer Praklische Chemie (Leipzig) (1962) 16, 1-7), or from α-dihydro derivative (Tetrahedron: Asymmetry (1998) 9, 4117-4122), or from an aryllithium (J. Org. Chem. (1982) 47, 4347-4348; and Tetrahedron Lett. (1989) 30, 989-992), or from α-diketone derivative (Journal fuer Praklische Chemie (Leipzig) (1962) 16, 1-7), or from an aryl ester (Tetrahedron Lett, (1980) 21, 2227-2228); and allowing, for example, ammonia and/or ammonium acetate to act on the benzoin intermediate in the presence of oxygen to yield a target compound (J. Org. Chem. (1937) 2, 328-; Bull. Soc. Chim. Fr. (1968) 4970-; Helvetica Chimica Acta (1985) 68 (3), 592-599; and C. R. Seances Acad. Sci., Ser C. (1966) 263, 1156-);

[Chemical Formula 42]

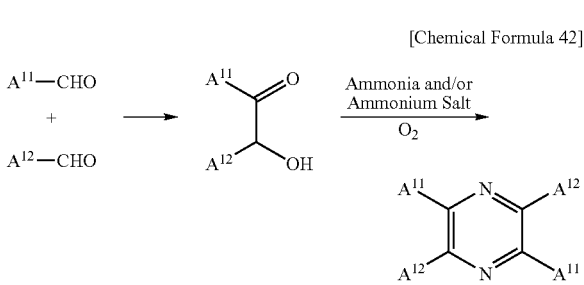

(2-b) a process of cyclizing an α-diketone and an α-diamine (J. Org. Chem. 57 (1992) 24, 6653-6657; Helvetica Chimica Acta (1976) 59, 1169-; and Helvetica Chimica Acta (1973) 56, 610-), and subjecting she cyclized compound to oxidation to yield a target compound (Helvetica Chimica Acta (1976) 59, 1169-);

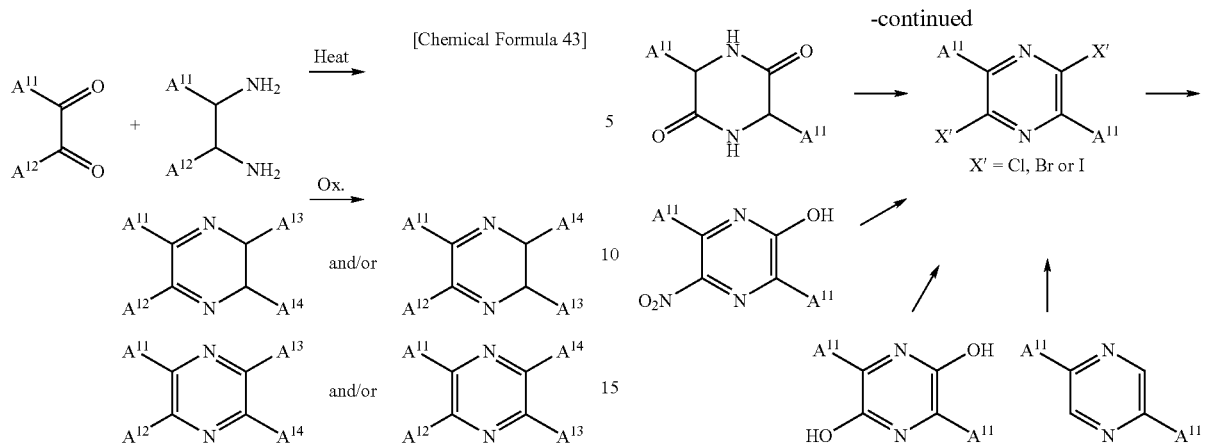

(2-c) a process of allowing, for example, ammonia and/or ammonium acetate to act on an α-haloketone to yield a target compound (Japanese Unexamined Patent Application Publication No. 03-048666);

[Chemical Formula 44]

(2-d) a process of allowing, for example, ammonia and/or ammonium acetate to act on one aromatic amide or two or more different aromatic amides (Helvetica Chimica Acta (1985) 68, 592-599; and Japanese Unexamined Patent Application Publication No. 06-065212);

[Chemical Formula 45]

(2-e) a process of yielding a dihalide of pyrazine from an amino acid via an amino acid anhydride (Bull. Soc. Chem. Fr. (1942) 9, 487-; J. Am. Pharm. Assoc., Sci. Ed. (1957) 46, 391-), or via other paths (J. Heterocyclic Chem. (1986) 23, 871-875; Chemical & Pharmaceutical Bull. (1979) 27, 2980-2987; and J. Am. Chem. Soc. (1956) 78, 4071-4077), and subjecting this to a coupling reaction with an arylboronic acid (Suzuki Coupling process), or with an azole such as carbazole, indole, pyrrole, or pyrazole (Suzuki Coupling process (Tetrahdron 48 (1992) 37, 8117-8126) or Ullman process), or with a tetraaryltin (Heterocycles (1986) 24, 785-792) to yield a target compound;

[Chemical Formula 46]

R' = H, Alkyl or Aryl (2-f) a process of synthetically preparing a target compound from pyrrole (Justus Liebigs Ann. Chem. (1952) 578, 226-); and

[Chemical Formula 47]

(2-g) Other preparation processes:

Other preparation processes usable herein include those described or cited typically in "Heterokan No Kagaku-Iyakuhin No Kiso (in Japanese; Heterocyclic Chemistry-Foundation of Pharmaceutical Drugs)" (2002, Kunieda, et al., Kagaku-Dojin Publishing Company, Inc.); "Heterocyclic Chemistry" (4th ed., 2000, J. A. Joule and K. Mills, Blackwell Science Co.); "Heterocyclic Compounds, New Edition, Foundation and Application" (2004, Hiroshi Yamanaka et al., Kodansha Ltd.); and "Vollhardt & Schore, Organic Chemistry, Last Volume" (2004, K. P. C. Vollhardt, Kagaku-Dojin Publishing Company, Inc.).

(3) A pyrimidine ring can be introduced, for example, according to a process of using a palladium catalyst described in Journal of Organometallic Chemistry, 663 (1-2), 46-57, 2002 or Journal of Organic Chemistry, 66 (21), 7125-7128, 2001, as well as preparation processes described or cited typically in "Heterokan No Kagaku-Iyakuhin No Kiso (in Japanese; Heterocyclic Chemistry-Foundation of Pharmaceutical Drugs)" (2002, Kunieda, et al., Kagaku-Dojin Publishing Company, Inc.); "Heterocyclic Chemistry" (4th ed., 2000, J. A. Joule and K. Mills, Blackwell Science Co.); "Heterocyclic Compounds, New Edition, Foundation and Application" (2004, Hiroshi Yamanaka et al., Kodansha Ltd.); and "Vollhardt & Schore, Organic Chemistry, Last Volume" (2004, K. P. C. Vollhardt, Kagaku-Dojin Publishing Company, Inc.).

(4) A triazine ring can be introduced, for example, according to one of the following processes (4-a), (4-b), and (4-c).

(4-a) A process of synthesizing from an aryl cyanide;

[Chemical Formula 48]

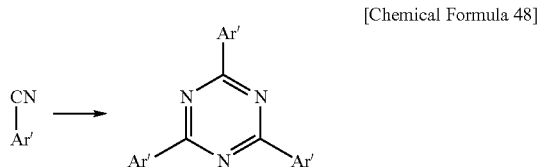

wherein Ar's may be the same as or different from one another and each represent an arylene group, a heteroarylene group, or an unsaturated hydrocarbon group each of which may have an arbitrary substituent such as a halogen atom, an aryl group, or a heteroaryl group.

More specifically, this preparation process can be carried out according to procedures described or cited typically in Faming Zhuanli Shenqing Gongkai Shuomingshu, 1382687, 4 Dec. 2002, Journal of Organic Chemistry, 68 (12), 4855-4861; 2003, Green Chemistry, 4 (4), 339-343; 2002, Chinese Journal of Chemistry, 20 (11), 1334-1339; 2002, Synthetic Communications, 30 (6), 1017-1022; 2000, Chemistry Letters, (7), 545-546; 1999, Mendeleev Communications, (5), 166-167; 1994, Journal of Heterocyclic Chemistry, 25 (3), 767-770; 1988, and Journal of Organic Chemistry, 52 (16), 3674-3680; 1987.

(4-b) A process of synthesizing a target compound from a trihalogenated triazine:

[Chemical Formula 49]

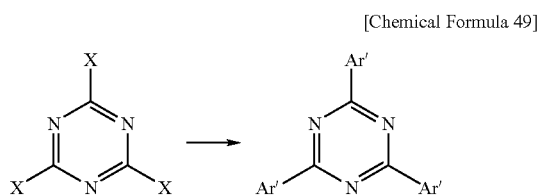

wherein Xs each represent any one of fluorine, chlorine, bromine, and iodine; and Ars may be the same as or different from one another and each represent an arylene group, a heteroarylene group, or an unsaturated hydrocarbon group each of which may have an arbitrary substituent such as a halogen atom, an aryl group, or a heteroaryl group.

More specifically, when Xs are each chlorine, bromine or iodine, this preparation process can be carried out according to procedures described or cited typically in Journal of Organic Chemistry, 68 (9), 3367-3379; 2003, Journal of Organic Chemistry, 67 (24), 8424-8429; 2002, Inorganic Chemistry, 41 (9), 2543-2547; 2002, Synthetic Metals, 122 (3), 485-493; 2001, Organic Letters, 3 (15), 2419-2421; 2001, U.S. Pat. No. 5,726,310, 10 Mar. 1998, Tetrahedron Letters, 38 (46), 8017-8020; 1997, Eur. Pat. Appl., 779280, 18 Jun. 1997, Mendeleev Communications, (5), 166-167; 994, and U.S. Pat. No. 4,826,978, 2 May 1989.

When Xs are fluorines, a preparation process described or cited typically in Chemistry of Materials, 16(1), 185-194; 2004 can be employed.

(4-c) Other preparation processes

There can also be used preparation processes described or cited typically in Journal of Organic Chemistry, 68 (12), 4855-4861; 2003, European Journal of Organic Chemistry, (10), 1948-1953; 2003, Tetrahedron, 56 (37), 7153-7161; 2000, Journal of the Indian Chemical Society, 73(6), 283-284; 1996, Eur. Pat. Appl., 649841, 26 Apr. 1995, Archiv der Pharmazie (Weinheim, Germany), 327 (6), 389-391; 1994, Izvestiya Natsional'noi Akademii Nauk Respubliki Kazakhstan, Seriya Khimicheskaya, (2), 13-20; 1993, Eur. Pat. Appl., 497734, 5 Aug. 1992, Heterocycles, 34 (2), 341-347; 1992, Sibirskii Khimicheskii Zhurnal, (4), 96-98; 1991, Bulletin of the Chemical Society of Japan, 62 (10), 3171-3176; 1989, Journal of the Chemical Society, Perkin Transactions 2: Physical Organic Chemistry (1972-1999), (2), 117-122; 1988, Zeltschrift fuer Chermie, 26 (8), 295-297; 1986, Khimiya Geterotsiklicheskikh Soedinenii, (1), 107-113; 1986, Synthesis, (1), 95-98; 1985, Journal of Heterocyclic Chemistry, 18(6), 1197-1201; 1981, Tetrahedron Letters, (43), 4193-4196; 1979, and Ber., 96, 1213-1217; 1963.

Other preparation processes usable herein include those described or cited typically in "Heterokan No Kagaku-Iyakuhin No Kiso (in Japanese; Heterocyclic Chemistry-Foundation of Pharmaceutical Drugs)" (2002, Kunieda, et al., Kagaku-Dojin Publishing Company, Inc.); "Heterocyclic Chemistry" (4th ed., 2000, J. A. Joule and K. Mills, Blackwell Science Co.); "Heterocyclic Compounds, New Edition, Foundation and Application" (2004, Hiroshi Yamanaka et al., Kodansha Ltd.); and "Vollhardt & Schore, Organic Chemistry, Last Volume" (2004, K. P. C. Vollhardt, Kagaku-Dojin Publishing Company, Inc.).

(5) The introduction of an N-carbazolyl group can be carried out, for example, according to any of the following processes (5-a), (5-b), and (5-c) as a process of introducing a carbazolyl group in the final step of synthesis:

Process (5-a): According to this process, an organic compound according to the present invention can be obtained in the following manner. Initially, a basic skeleton having fluorine atoms as a substituent is prepared by subjecting a small excess of a halogenated aromatic boron compound and an aromatic di- or tri-substituted halide to heating under reflux in the presence of a palladium catalyst and a base in a solvent in an inert gas atmosphere for about five to about twenty-four hours. The halogenated aromatic boron compound includes, for example, fluorophenylboronic acid, difluorophenylboronic acid, fluorobiphenylboronic acid esters, and pentafluorophenylboronic acid. The "small excess" of the halogenated aromatic boron compound is about 0.7 to 1.5 times by equivalent relative to halogen atoms of the halide. The aromatic di- or tri-substituted halide includes, for example, dibromofluorobenzene, diiodobenzene, tribromobenzene, trichlorotriazine, and diiodobiphenyl. The palladium includes, for example, tetrakis(triphenylphosphine)palladium. The amount of the palladium catalyst is about 0.1 to about 10 percent by mole. The base includes, for example, cesium carbonate, potassium phosphate, and sodium carbonate. The amount of the base is about 2 to about 10 times by equivalent to halogen atoms of the halide. The solvent includes, for example, toluene-ethanol, toluene-water, tetrahydrofuran, dioxane, dimethoxyethane, N,N-dimethylformamide, and mixtures of these solvents. The amount of the solvent is such that the concentration of the boronic acid is about 1 to about 1000 percent by millimole.

Next, a substituted or unsubstituted carbazole is stirred and reacted with a strong base at temperatures of −78° C. to +60° C. in a dry gas atmosphere and/or inert gas atmosphere in a solvent for one-tenth to sixty hours to yield a reaction mixture. The amount of the substituted or unsubstituted carbazole is about 1.1 to 10 equivalents relative to fluorine atoms on the basic skeleton having fluorine atoms as a substituent. The solvent includes, for example, tetrahydrofuran, dioxane, ether, and N,N-dimethylformamide. The strong base includes, for example, sodium hydride, tert-butoxypotassium, and n-butyllithium. The amount of the strong base is about 0.3 to about 2 equivalents relative to hydrogen on the nitrogen atom of the after-mentioned azole compound. Next, the reaction mixture is mixed with a solution of the above-prepared basic skeleton having fluorine atoms as a substituent in a solvent and stirred with heating under reflux for one to sixty hours to thereby yield an organic compound according to the present invention. The solvent herein includes, for example, tetrahydrofuran, dioxane, ether, and N,N-dimethylformamide.

Process (5-b): According to this process, an organic compound according to the present invention can be obtained in the following manner. Initially, a basic skeleton having bromine atom and/or chlorine atom as substituent(s) is prepared by subjecting a small excess of a halogenated aromatic boronic acid and a di- or tri-substituted halide to heating under reflux in the presence of a palladium catalyst and a base in a solvent in an inert gas atmosphere for about five to twenty-four hours. The halogenated aromatic boronic acid includes, for example, bromophenylboronic acid, dibromophenylboronic acid, and dichlorophenylboronic acid. The "small excess" of the halogenated aromatic boronic acid is about 1.1 to 1.5 times by equivalent relative to halogen atoms of the halide. The di- or tri-substituted halide includes, for example, diiodobenzene, bromodiiodobenzene, triiodobenzene, trichlorotriazine, and diiodobiphenyl. The palladium catalyst can be, for example, tetrakis(triphenylphosphine)palladium. The amount of the palladium catalyst is about 0.01 to about 1 equivalent to halogen atoms of the halide. The base includes, for example, cesium carbonate, potassium phosphate, and sodium carbonate. The amount of the base is about 2 to about 10 equivalents relative to halogen atoms of the halide. The solvent includes, for example, toluene, ethanol, water, tetrahydrofuran, dioxane, dimethoxyethane, N,N-dimethylformamide, and mixtures of these solvents. The amount of the solvent is such that the concentration of the halide is about 1 to about 1000 percent by millimole.

When the prepared basic skeleton has bromine group, it can be converted into a skeleton having iodine group instead of bromine group according to necessity, by subjecting the basic skeleton to stirring in the presence of potassium iodide and copper iodide in a solvent at 100° C. to 300° C. for a half hour to sixty hours. The amount of potassium iodide is 1.5 to 10 equivalents relative to bromine atoms on the basic skeleton. The amount of copper iodide is 1 to 10 equivalents. The solvent can be, for example, N,N-dimethylformamide. The amount of the solvent is such that the concentration of the halide is about 0.1 to about 10 percent by mole.

Next, the basic skeleton having bromine atom or/and chlorine atom as substituent(s), and a carbazole in an amount of about 1.0 to 100 equivalents to the bromine atom or/and chlorine atom on the basic skeleton are subjected to, for example, following processes (i) or (ii) to thereby yield an organic compound according to the present invention.

(i) A process of mixing with stirring in the presence of a copper catalyst under an inert gas stream in the absence of or in the presence of a solvent at temperatures of from 20° C. to 300° C. for one to sixty hours. The copper catalyst includes, for example, copper powder, copper wire, a halogenated copper ($CuX^r$, wherein $X^r$ is Cl, Br, or I), and copper oxide (CuO). The amount of the copper catalyst is about 1 to 5 equivalents relative to bromine atom or/and chlorine atom on the basic skeleton. The solvent can be, for example, Tetraglyme or polyethylene glycol, and the amount thereof is about 0.1 to 2 liters per 1 mole of the basic skeleton.

(ii) A process of stirring in the presence of a catalyst, and where necessary a strong base, in the coexistence of, where necessary, a copper catalyst in a solvent at 30° C. to 200° C. for one to sixty hours. The catalyst includes, for example, a combination of a bivalent palladium catalyst with a ligand; a zerovalent palladium complex such as $Pd(PPh)_4$, wherein Ph represents phenyl; and a palladium chloride complex such as $PdCl_2 (dppf)_2$. Such bivalent palladium catalysts include $Pd_2(dba)_3$, wherein Pd represents palladium and "dba" represents dibenzylideneacetone, $Pd(dba)_2$, and palladium acetate. Such ligands include BINAP (i.e., 2,2'-bis(diphenylphosphino-1,1'-binaphthyl), tri(tert-butyl)phosphine, triphenylphosphine, 1,2-bis(diphenylphosphino)ethane, 1,3-bis(diphenylphosphino)propane, 1,3-bis(diphenylphosphino)butane, and dppf (i.e., 1,1'-bis(diphenylphosphino)ferrocene). The amount of the catalyst is generally about 0.01 to 1 equivalent relative to 1 equivalent of the bromine atom or/and chlorine atom on the basic skeleton. The strong base includes, for example, tert-butoxypotassium, tert-butoxysodium, potassium carbonate, and triethylamine. The amount of the strong base is generally about 1.1 to 10 equivalents relative to 1 equivalent of a hydrogen halide which may be formed as a result of reaction. The copper catalyst includes, for example, copper iodide. The amount of the copper catalyst is generally 1 to 10 equivalents relative to 1 equivalent of a hydrogen halide which may be formed as a result of reaction. The solvent includes, for example, tetrahydrofuran, dioxane, dimethoxyethane, N,N-dimethylformamide, dimethyl sulfoxide, xylenes, toluene, and triethylamine. The amount of the solvent is generally such that the concentration of the basic skeleton having bromine atom or/and chlorine atom as substituent(s) is about 0.1 to 100 percent by millimole.

(5-c) In addition, any known procedure, such as a Grignard reaction, a process using zinc, or a process using tin, can be applied to the coupling. Such catalysts for use herein include catalytic transition metals such as palladium, nickel, and copper. The amount of the catalyst is generally about 0.1 to about 200 percent by mole relative to an intermediate having a carbazole ring. Basic substances for use herein include potassium carbonate, calcium carbonate, potassium phosphate, cesium carbonate, and tert-butoxysodium. The amount of such basic substances is generally about 50 to about 1000 percent by mole relative to an intermediate having a carbazole ring. The reaction temperature is generally 0° C. or higher, and preferably 50° C. or higher, and is generally 300° C. or lower, and preferably 200° C. or lower. Solvents usable in the reaction include aromatic solvents such as toluene, xylenes, and nitrobenzene; and ether solvents such as tetrahydrofuran, ethlyene glycol dimethyl ether, and Tetraglyme.

(6) The introduction of a 2-, 3-, 4-, 5-, 6-, 7- or 8-carbazolyl group can be carried out, for example, by using a coupling reaction between an aryl borate and a carbazole having a halogen atom, such as chlorine, bromine, or iodine, at the position to which the linkage group Z is bound, or a coupling reaction between a halogenated aryl and a carbazolyl borate. More specifically, any known coupling procedures can be used herein. Such coupling procedures are bonding reactions (coupling reactions) between rings, as described or cited typically in "Palladium in Heterocyclic Chemistry: A guide for the Synthetic Chemist" (Second Ed., 2002, die Jack Li and Gordon W. Gribble, Pergamon Press), Sen-ikinzoku Ga Hiraku Yukigousei-Sono Tasai Na Hannokeishiki To Saishin No Seika (in Japanese; Organic Syntheses Developed by Transition Metals, Their Various Reaction Modes and Latest Products)" (1997, Jiro Tsuji, Kagaku-Dojin Publishing Company, Inc.), and "Vollhardt & Schore, Organic Chemistry, Last Volume" (2004, K. P. C. Vollhardt, Kagaku-Dojin Publishing Company, Inc.).

(7) In addition to the above-exemplified preparation procedures or processes, where necessary, any known coupling procedures can be applied to the formation of a linkage group, namely -G-Q-(Ring $A^1$)-Z—, connecting between Cz group in Formula (I) and any one of the pyridine ring in Formula (II-1), the pyrazine ring in Formula (II-2), the pyrimidine ring in Formula (II-3), and the triazine ring in Formula (II-4). Such coupling procedures are bonding reactions (coupling reactions) between rings, as described or cited typically in "Palladium in Heterocyclic Chemistry: A guide for the Synthetic Chemist" (Second Ed., 2002, Jie Jack Li and Gordon W. Gribble, Pergamon Press), Sen-ikinzoku Ga Hiraku Yukigousei-Sono Tasai Na Hannokeishiki To Saishin No Seika (in Japanese, Organic Syntheses Developed by Transition Metals, Their Various Reaction Modes and Latest Products)" (1997, Jiro Tsuji, Kagaku-Dojin Publishing Company, Inc.), and "Vollhardt & Schore, Organic Chemistry, Last Volume" (2004, K. P. C. Vollhardt, Kagaku-Dojin Publishing Company, Inc.).

(8) The purification of a compound can be carried out, for example, by using known techniques such as techniques described in "Handbook of Separation/Purification Technology" (1993, edited by the Chemical Society of Japan), "High-purity Separation of Trace Components and Difficult-to-Separate Substances by Chemical Conversion" (1988, published by IPC Co., Ltd.), and "Experimental Chemistry (Fourth Ed.) Vol. 1; Section: Separation and Purification" (1990, edited by the Chemical Society of Japan). Specific examples of purification procedures include extraction (including washing in a suspended state, boiling washing, ultrasonic washing, and washing with an acid and/or a base), adsorption, occlusion, melting or fusion, crystallization (including recrystallization from a solvent, and reprecipitation), distillation (distillation under normal pressure, and distillation under reduced pressure), evaporation, sublimation (sublimation under normal pressure and sublimation under reduced pressure), ion exchange, dialysis, filtration, ultrafiltration, reverse osmosis, pressurized osmosis, zone melting, electrophoresis, centrifugation, floatation separation, sedimentation, magnetic separation, and various chromatography techniques. Such chromatography techniques are classified by the shape into column, paper, thin-layer, and capillary chromatography; by the mobile phase into gas, liquid, micelle, and supercritical fluid chromatography; and by the separation mechanism into adsorption, partition, ion-exchange, molecular sieve, chelate, gel filtration, exclusion, and affinity chromatography.

(9) The identification of a product and the analysis of a purity thereof can be carried out by applying a procedure or an apparatus according to necessity. Such procedures and apparatuses for use herein include a gas chromatograph (GC), a high-performance liquid chromatograph (HPLC), a high-performance amino acid analyzer (AAA), capillary electrophoresis measurement (CE), a size exclusion chromatograph (SEC), a gel permeation chromatograph (GPC), a cross fractionation chromatograph (CFC), mass spectrometry (MS, LC/MS, GC/MS, and MS/MS), a nuclear magnetic resonance apparatus (NMR ($^1$H-NMR and $^{13}$C-NMR)), a Fourier transform infrared spectrophotometer (FT-IR), an ultraviolet-visible ray-near infrared spectrophotometer (DV.VIS, NIR), an electron spin resonance spectrometer (ESR), a transmission electron microscope (TEM-EDX), an electron probe microanalyzer (EPMA), metal element analysis (an ion chromatograph, inductively-coupled plasma atomic emission spectrometry (ICP-AES), atomic absorption spectrophotometry (AAS), and an X-ray fluorescence spectrometer (XRF)), nonmetal element analysis, and trace analysis (inductively coupled plasma mass spectrometry (ICP-MS), graphite furnace atomic absorption spectrometry (GF-AAS), and glow discharge mass spectrometry (GD-MS)).

[Charge Transporting Material]

An organic compound according to the present invention can be used as a charge transporting material. A charge transporting material according to the present invention can be any one, as long as it contains an organic compound according to the present invention, but is generally preferably a charge transporting material made of an organic compound according to the present invention.

[Organic Electroluminescent Device]

Next, an organic electroluminescent device according to the present invention using an organic compound according to the present invention will be illustrated.

An organic electroluminescent device according to the present invention is an organic electroluminescent device including a substrate bearing an anode, a cathode, and an organic light-emitting layer arranged between the two electrodes, in which the organic electroluminescent device include a layer containing an organic compound according to the present invention. The device preferably includes the organic compound according to the present invention in the organic light-emitting layer. The device particularly preferably contains the organic compound according to the present invention as a host material in the organic light-emitting layer, which host material is doped with an organometallic complex.

When used as a host material of an organic light-emitting layer of an organic electroluminescent device as above, each of organic compounds according to the present invention can be used alone or in combination.

Hereinafter, structures of organic electroluminescent devices according to the present invention will be illustrated by way of example, with reference to the attached drawings. It should be noted, however, the exemplified structures of organic electroluminescent devices according to the present invention are not limitative.

FIGS. 1 to 4 are cross-sectional views schematically illustrating structures of organic electroluminescent devices according to the present invention by way of example. FIGS. 1 to 4 illustrate a substrate 1, an anode 2, a hole injection layer (anode buffer layer) 3, a hole transport layer 4, an organic light-emitting layer (hereinafter also referred to as "light-emitting layer") 5, a hole blocking layer 6, an electron transport layer 7, and a cathode 8.

Substrate

The substrate 1 functions as a support in the organic electroluminescent device, and a plate of quartz or glass, a metal plate or metal foil, or a plastic film or sheet is used. In particular, a glass plate and a plate or film of transparent synthetic resin such as a polyester, a polymethacrylate, a polycarbonate or a polysulfone are preferred. When a synthetic resin substrate is used, its gas barrier properties are important. If the gas barrier properties are too poor, the organic electroluminescent device might deteriorate due to the air outside having passed through the substrate, thus poor gas barrier properties not being preferred. To avoid this, for example, a dense silicon oxide film may be preferably arranged on at least one side of the synthetic resin substrate to thereby ensure sufficient gas barrier properties.

Anode

An anode 2 is arranged on the substrate 1. The anode 2 serves to inject holes into a hole transport layer 4. The anode 2 generally includes a metal such as aluminum, gold, silver, nickel, palladium or platinum, a metal oxide such as indium oxide and/or tin oxide, a metal halide such as copper iodide, carbon black, or a conductive polymer such as poly(3-methylthiophene), polypyrrole or polyaniline. The anode 2 is generally formed by sputtering or vacuum deposition. When the anode 2 is formed from fine particles of a metal such as silver, fine particles of copper iodide, carbon black, fine particles of a conductive metal oxide or fine particles of a conductive polymer, it can also be formed by dispersing such particles in a suitable binder resin solution and coating the dispersion on the substrate 1. Further, when the anode 2 is formed from an electroconductive polymer, the anode 2 can also be directly formed as a polymerized thin film on the substrate 1 through electrolytic polymerization or formed by applying an electroconductive polymer to the substrate 1 (App. Phys. Lett., vol. 60, p. 2711, 1992).

The anode 2 is usually of a single-layer structure but, as needed, it may be of a multilayer structure made from two or more different materials.

The thickness of the anode 2 varies depending upon required transparency. When some transparency is required, the transmittance for visible light is adjusted to be usually 60% or more, and preferably 80% or more. In this case, the thickness of the anode is usually 5 nm or more, and preferably 10 nm or more, and is usually 1,000 nm or less, and preferably 500 nm or less. When the anode may be opaque, the thickness of the anode 2 is arbitrary, and may be formed by a metal according to necessity, so as to also function as the substrate 1.

Hole Transport Layer

The device of the structure shown in FIG. 1 includes a hole transport layer 4 arranged on the anode 2. A material for the hole transport layer is required to show a high hole injecting efficiency from the anode and transport the injected holes with high efficiency. For satisfying the requirements, the material is required to have a small ionization potential, show a high transparency for a visible light, show a high hole mobility, have an excellent stability and resistance to the formation of impurities, which function as a trap, upon production or upon use. Since the hole transport layer is in contact with the light-emitting layer 5, the material is required not to reduce the luminous efficiency by quenching the light emitted from the light-emitting layer 5 or by forming an exciplex with the light-emitting layer 5. In addition to the above-described general requirements, the device is required to have some heat resistance in consideration of application to an onboard display. Therefore, a material having a glass transition temperature of 85° C. or higher is desirable.

Examples of such hole transporting materials include, as with hole transporting materials for use as a host material of the light-emitting layer 5, aromatic diamines containing two or more tertiary amines wherein the nitrogen atoms are substituted by two or more condensed aromatic rings, typified by 4,4'-bis[N-(1-naphthyl)-N-phenylamino]biphenyl (Japanese Unexamined Patent Application Publication No. 5-234681); aromatic amine compounds having a star-burst structure such as 4,4',4''-tris(1-naphthylphenylamino)triphenylamine (J. Lumin., vol. 72-74, p. 985, 1997); aromatic amine compounds Including a tetramer of triphenylamine (Chem. Commun., p. 2175, 1996); spiro compounds such as 2,2',7,7'-tetrakis-(diphenylamino)-9,9'-spirobifluorene (Synth. Metals, vol. 91, p. 209, 1997); and carbazole derivatives such as 4,4'-N,N'-dicarbazolebiphenyl. Each of these compounds can be used alone or in combination according to necessity.

In addition to the above-mentioned compounds, materials for the hole transport layer 4 further include polymer materials such as polyvinylcarbazoles, polyvinyltriphenylamines (Japanese Unexamined Patent Application Publication No. 7-53953), and poly(arylene ether sulfone)s containing tetraphenylbenzidine (Polym. Adv. Tech., vol. 7, p. 33, 1996).

The hole transport layer 4 can be formed by a wet filming process or a dry filming process. Such wet filming processes include common coating processes such as spraying, printing, spin coating, dip coating, and die coating; and printing processes such as an ink jet process and screen printing. Such dry filming processes include a vacuum deposition process.

When the hole transport layer 4 is formed by a coating process, one or more different hole transporting materials and, as needed, a binder resin and/or an additive such as a coating property-improving agent which does not function as a trap of holes are dissolved in a proper solvent to prepare a coating solution, and the solution is applied to the anode 2 according typically to spin coating, followed by drying to form the hole transport layer 4. Examples of the binder resin include polycarbonates, polyarylates, and polyesters. When added in a large amount, the binder resin would reduce the hole mobility, and hence the amount is preferably small. Accordingly, the content in the hole transport layer is generally preferably 50 percent by weight or less.

When the hole transport layer is formed by vacuum deposition, a hole transporting material is placed in a crucible installed within a vacuum chamber and, after evacuating the vacuum chamber using a suitable vacuum pump to a degree of vacuum of about $10^{-4}$ Pa, the crucible is heated to evaporate the hole transporting material and form the hole transport layer 4 on the substrate 1 bearing the anode 2 which is placed facing the crucible.

The thickness of the hole transport layer 4 is usually 5 nm or more, and preferably 10 nm or more, and is usually 300 nm or less, and preferably 100 nm or less. In order to uniformly form such a thin film, vacuum deposition is generally often employed.

Organic Light-Emitting Layer

In the device shown in FIG. 1, a light-emitting layer 5 is arranged on the hole transport layer 4. The light-emitting layer 5 is formed by a light-emitting compound which can emit a strong light when strongly excited in a space between energized electrodes. The excitation is caused by recombination of holes injected from the anode and having migrated through the hole transport layer with electrons injected from the cathode and having migrated through the hole blocking layer 6. The light-emitting layer 5 generally contains a dopant material acting as a light-emitting substance, and a host material. Materials contained in a light-emitting layer, such as a dopant material and a host material, are herein referred to as light-emitting layer materials.

Such a light-emitting layer material to be used in the light-emitting layer 5 is required to be a compound which shows a stable thin film form, shows a high quantum yield in emission of light (fluorescence or phosphorescence) in a solid state and can transport holes and/or electrons with a high efficiency. Further, the compound is required to be electrochemically and chemically stable and resistant to the formation of impurities, functioning as a trap, upon production or use thereof.

Light-emitting materials for use in the present invention are preferably light-emitting materials having a first oxidation potential smaller than the first oxidation potential of a hole blocking material, in which the first oxidation potentials are determined in cyclic voltammetry, as described in the after-mentioned hole blocking layer. Of such light-emitting materials, more preferred as light-emitting layer materials are light-emitting materials satisfying the following conditions:

(Oxidation potential of the hole blocking material)−(Oxidation potential of the light-emitting layer material)≧0.1 V (Reduction potential of the hole blocking material)≧(Reduction potential of the light-emitting material)

When the light-emitting layer 5 contains a host material and a dopant material, the oxidation or reduction potential of the light-emitting layer material in the above formulae refers to the oxidation or reduction potential of the host material.

Such materials which satisfy the requirements and can form organic light-emitting layers capable of emitting fluorescence include metal complexes such as 8-hydroxyquinoline aluminum complex (Japanese Unexamined Patent Application Publication No. 59-194393), metal complexes of 10-hydroxybenzo[h]quinoline (Japanese Unexamined Patent Application Publication No. 6-322362), bisstyrylbenzene derivatives (Japanese Unexamined Patent Application Publications No. 1-245087 and No. 2-222484), bisstyrylarylene derivatives (Japanese Unexamined Patent Application Publication No. 2-247278), metal complexes of (2-hydroxyphenyl)benzothiazole (Japanese Unexamined Patent Application Publication No. 8-315983), and silole derivatives. These materials for the light-emitting layer are deposited on the hole transport layer usually by vacuum deposition. Of the above-mentioned hole transport materials, aromatic amine compounds capable of emitting a light can also be used as the light-emitting layer materials.

For the purpose of improving luminous efficiency of the device and changing the color of emitted light, it has been conducted, for example, to dope a host material of 8-hydroxyquinoline aluminum complex with a fluorescent dye for laser such as coumarin (J. Appl. Phys., vol. 65, p. 3610, 1989). This doping technique can also be applied to the light-emitting layer 5 and, as the material for doping, various fluorescent dyes in addition to coumarin may be used as well. Examples of fluorescent dyes giving a blue light emission include perylene, pyrene, anthracene, coumarin, and derivatives of these. Examples of fluorescent dyes giving a green light emission include quinacridone derivatives and coumarin derivatives. Examples of fluorescent dyes giving a yellow light emission include rubrene and perimidone derivatives. Examples of fluorescent dyes giving a red light emission include DCM (4-dicyanomethylene-2-methyl-6-p-dimethylaminostyryl-4H-pyran)-based compounds, benzopyran derivatives, rhodamine derivatives, benzothioxanthene derivatives, and azabenzothioxanthene.

In addition to the above-described fluorescent dyes for doping, fluorescent dyes illustrated in Laser Kenkyu (in Japanese; Laser Research), vol. 8, p. 694, p. 803, p. 958 (1980) and ibid., vol. 9, p. 85 (1981) may be selected according to the kind of the host material and used as a doping material for the light-emitting layer.

The doping amount of the fluorescent dye relative to the host material is preferably $10^{-3}$ percent by weight or more, and more preferably 0.1 percent by weight or more, and is preferably 10 percent by weight or less, and more preferably 3 percent by weight or less. If the amount is less than the lower limit, the dopant might fall to contribute to improvement of luminous efficiency of the device whereas, if the amount exceeds the upper limit, there might result quenching of light, possibly leading to reduction in the luminous efficiency.

In this connection, an organic compound according to the present invention is suitable as a host material for an organic light-emitting layer of an organic electroluminescent device. This is because the organic compound has both a moiety mainly bearing a hole transporting property and another moiety mainly bearing an electron transporting property, thereby shows both excellent hole transporting ability and excellent electron transporting ability, and has excellent durability against electric oxidation/reduction and a high triplet excitation level, as described above. Thus, the organic light-emitting layer of an organic electroluminescent device according to the present invention preferably includes the organic compound according to the present invention as a host material, which host material is doped with an organometallic complex suitable as a light-emitting substance for the after-mentioned reasons.

Preferred dopant materials for use in a light-emitting layer in the present invention include organic metal complexes containing metals selected from metals belonging to Group 7 to Group 11 of the periodic table. These metal complexes preferably have a TI (excited triplet level) higher than T1 of the organic compound according to the present invention used as a host material, from the viewpoint of luminous efficiency. In addition, such a dopant material is required to have chemical stability typically against oxidation and reduction, because the dopant material serves to emit a light.

Preferred examples of the metal in the phosphorescent organometallic complex containing a metal selected from among metals belonging to Group 7 to Group 11 of the periodic table include ruthenium, rhodium, palladium, silver, rhenium, osmium, iridium, platinum, and gold. Preferred examples as these organometallic complexes include compounds represented by following Formula (V) or (VI):

$$MLk-jL'j \quad (V)$$

wherein M represents a metal; "k" represents the valency of the metal; L and L' each represent a bidentate ligand; and "j" represents 0 or 1 or 2:

[Chemical formula 50]

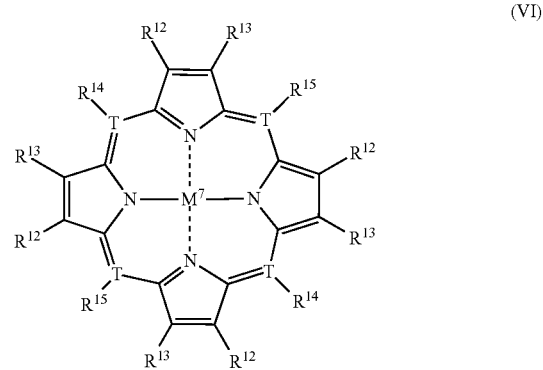

(VI)

wherein $M^7$ represents a metal; T represents carbon or nitrogen; and, when T represents nitrogen, $R^{14}$ and $R^{15}$ are absent and, when T represents carbon, $R^{14}$ and $R^{15}$ each represent a hydrogen atom, a halogen atom, an alkyl group, an aralkyl group, an alkenyl group, a cyano group, an amino group, an acyl group, an alkoxycarbonyl group, a carboxyl group, an alkoxy group, an alkylamino group, an aralkylamino group, a haloalkyl group, a hydroxyl group, an aryloxy group, an aromatic hydrocarbon group which may be substituted, or an aromatic heterocyclic group which may be substituted;

$R^{12}$ and $R^{13}$ each represent a hydrogen atom, a halogen atom, an alkyl group, an aralkyl group, an alkenyl group, a cyano group, an amino group, an acyl group, an alkoxycarbonyl group, a carboxyl group, an alkoxy group, an alkylamino group, an aralkylamino group, a haloalkyl group, a hydroxyl group, an aryloxy group, an aromatic hydrocarbon group which may be substituted, or an aromatic heterocyclic group which may be substituted, and $R^{12}$ and $R^{13}$ may be combined with each other to form a ring.

The bidentate ligands L and L' in Formula (V) each represent a ligand having the following partial structure:

[Chemical Formula 51]

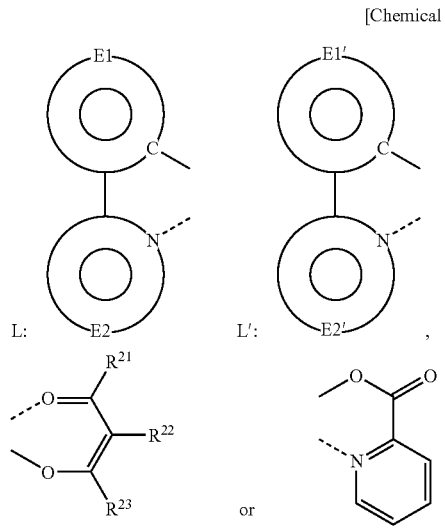

wherein Ring E1 and Ring E1' each independently represent an aromatic hydrocarbon group which may be substituted or an aromatic heterocyclic group which may be substituted; Ring E2 and Ring E2' each represent a nitrogen-containing aromatic heterocyclic group which may be substituted; and $R^{21}$, $R^{22}$ and $R^{23}$ each represent a halogen atom, an alkyl group, an alkenyl group, an alkoxycarbonyl group, a methoxy group, an alkoxy group, an aryloxy group, a dialkylamino group, a diarylamino group, a carbazolyl group, an acyl group, a haloalkyl group, or a cyano group.

More preferred examples of compounds represented by Formula (V) include compounds represented by following Formulae (Va), (Vb), and (Vc):

[Chemical Formula 52]

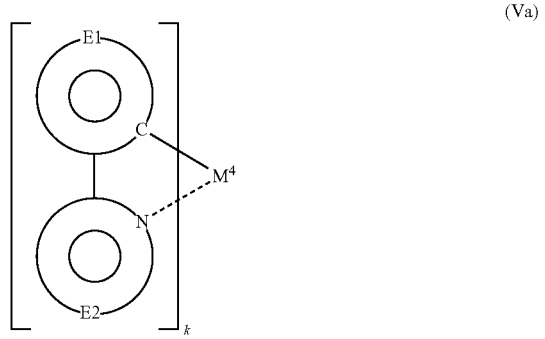

(Va)

wherein $M^4$ represents a metal; "k" represents the valency of the metal; Ring E1 represents an aromatic hydrocarbon group which may be substituted; and Ring E2 represents a nitrogen-containing aromatic heterocyclic group which may be substituted:

[Chemical Formula 53]

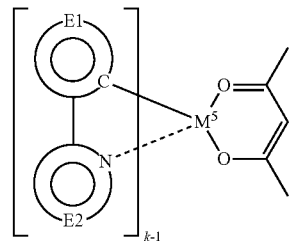

(Vb)

wherein $M^5$ represents a metal; "k" represents the valency of the metal; Ring E1 represents an aromatic hydrocarbon group which may be substituted or an aromatic heterocyclic group which may be substituted; and Ring E2 represents a nitrogen-containing aromatic heterocyclic group which may be substituted:

[Chemical Formula 54]

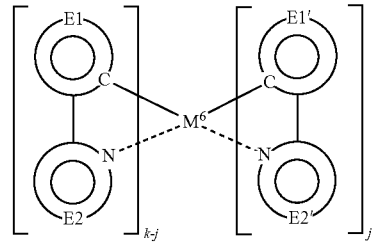

(Vc)

wherein $M^6$ represents a metal; "k" represents the valency of the metal; "j" represents 0 or 1 or 2; each of Ring E1 and Ring E1' independently represents an aromatic hydrocarbon group which may be substituted or an aromatic heterocyclic group which may be substituted; and each of Ring E2 and Ring E2' independently represents a nitrogen-containing aromatic heterocyclic group which may be substituted.

Preferred as Ring E1 and Ring E1' of the compounds represented by Formulae (Va), (Vb), and (Vc) are phenyl group, biphenyl group, naphthyl group, anthryl group, thienyl group, furyl group, benzothienyl group, benzofuryl group, pyridyl group, quinolyl group, isoquinolyl group, and carbazolyl group.

Preferred as Ring E2 and Ring E2' are pyridyl group, pyrimidyl group, pyrazyl group, triazyl group, benzothiazole group, benzoxazole group, benzimidazole group, quinolyl group, isoquinolyl group, quinoxalyl group, and phenanthrydyl group.

Examples of substituents which the compounds represented by Formulae (Va), (Vb) and (Vc) may have include halogen atoms such as fluorine atom; alkyl groups having one to six carbon atoms, such as methyl group and ethyl group; alkenyl groups having two to six carbon atoms, such as vinyl group; alkoxycarbonyl groups having two to six carbon atoms, such as methoxycarbonyl group and ethoxycarbonyl group; alkoxy groups having one to six carbon atoms, such as methoxy group and ethoxy group; aryloxy groups such as phenoxy group and benzyloxy group; dialkylamino groups such as dimethylamino group and diethylamino group; diarylamino groups such as diphenylamino group; carbazolyl groups; acyl groups such as acetyl group; haloalkyl groups such as trifluoromethyl group; and cyano group. These substituents may be combined with each other to form a ring.

Additionally, a substituent of Ring E1 and a substituent of Ring E2 may be combined with each other to form one condensed ring, or a substituent of Ring E1' and a substituent of Ring E2' may be combined with each other to form one condensed ring. An example of such a condensed ring is 7,8-benzoquinoline group.

More preferred examples of substituents in Ring E1, Ring E1', Ring E2 and Ring E2' include alkyl groups, alkoxy groups, aromatic hydrocarbon groups, cyano groups, halogen atoms, haloalkyl groups, diarylamino groups, and carbazolyl groups.

Preferred Examples of $M^4$ and $M^5$ in Formulae (Va) and (Vb) include ruthenium, rhodium, palladium, silver, rhenium, osmium, iridium, platinum, and gold. Preferred examples of $M^7$ in Formula (VI) include ruthenium, rhodium, palladium, silver, rhenium, osmium, iridium, platinum, and gold, of which bivalent metals such as platinum and palladium are more preferred.

Specific examples of the organometallic complexes represented by Formulae (V), (Va), (Vb), and (Vc) are illustrated below, which, however, not limitative at all.

[Chemical Formula 55]

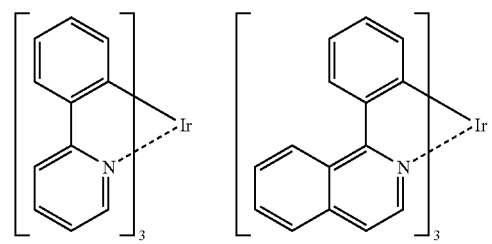

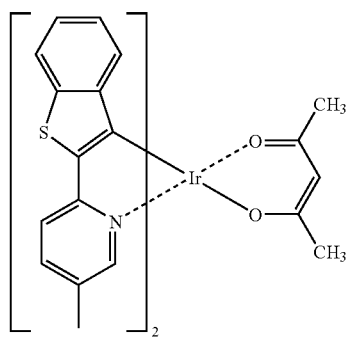

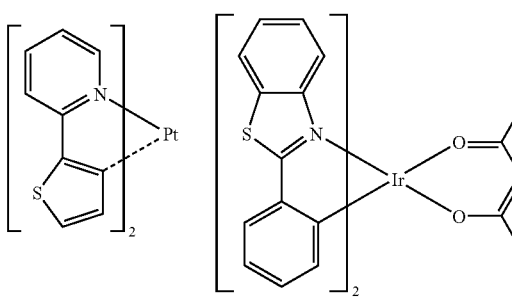

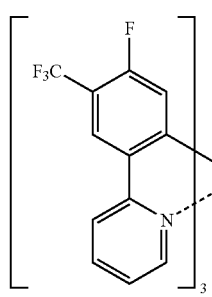

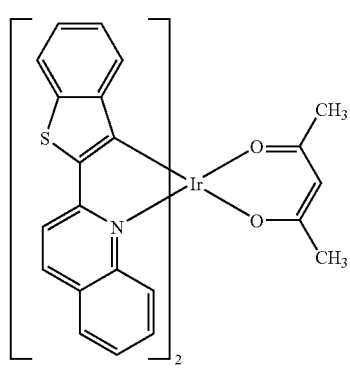

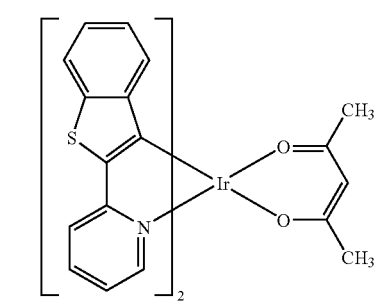

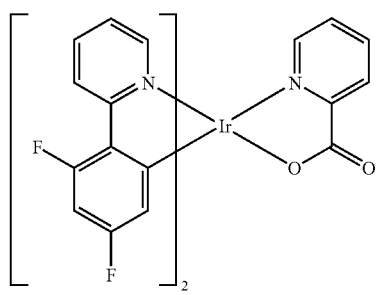

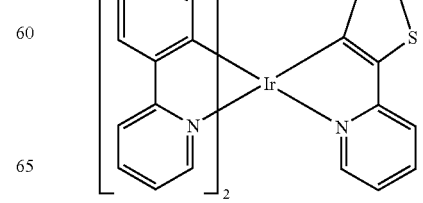

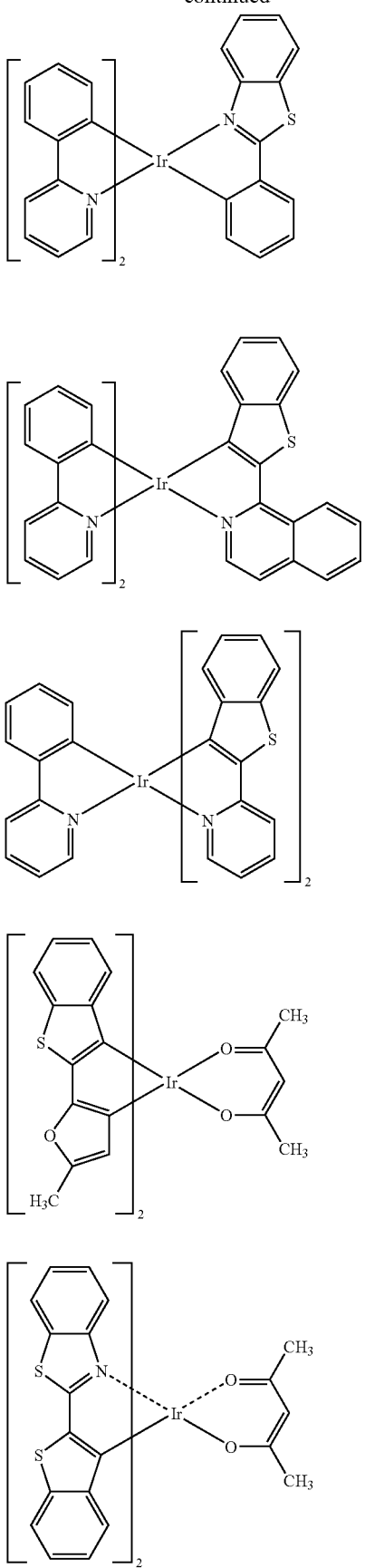
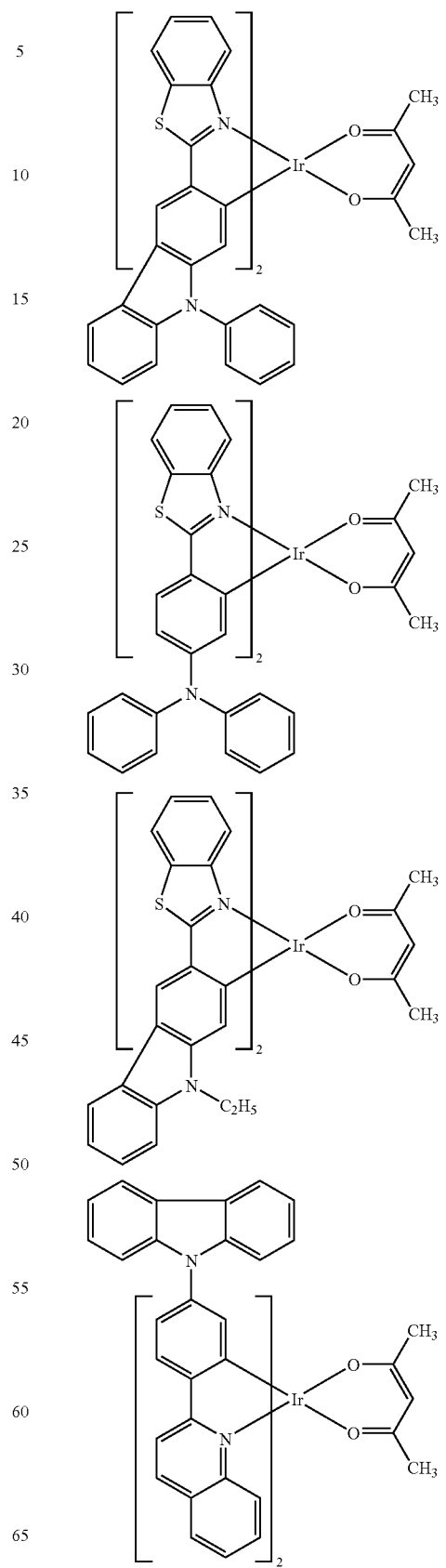

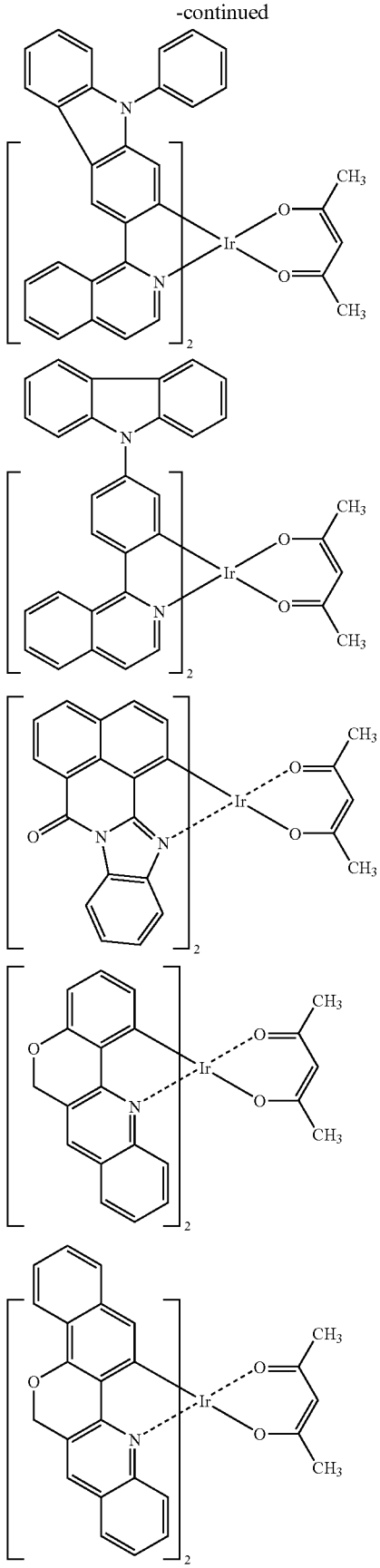

Of the organometallic complexes represented by Formulae (V), (Va), (Vb), and (Vc), typically preferred are compounds having, as ligand L and/or L', a 2-arylpyridine ligand such as an 2-arylpyridine, an 2-arylpyridine derivative having an arbitrary substituent, or an 2-arylpyridine derivative condensed with an arbitrary group.

Specific examples of the organometallic complexes represented by Formula (VI) are illustrated below, which, however, are not limitative at all. In the following formulae, Me represents a methyl group; and Et represents an ethyl group.

[Chemical Formula 57]

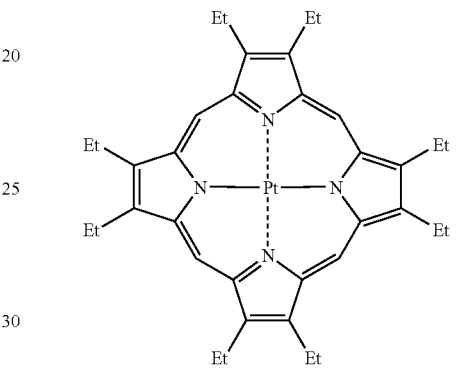

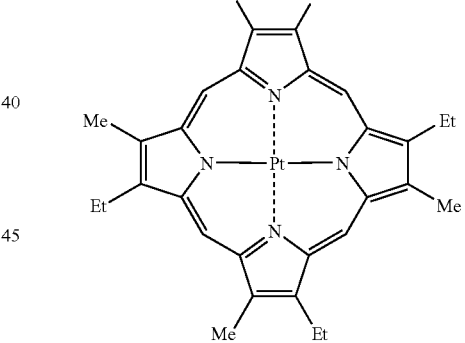

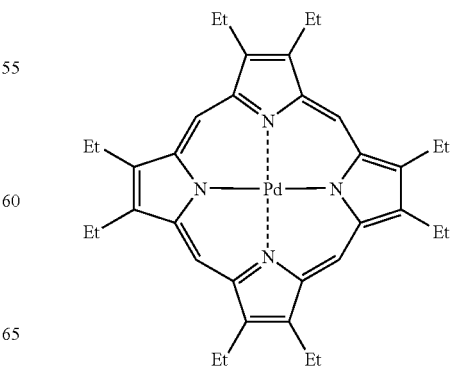

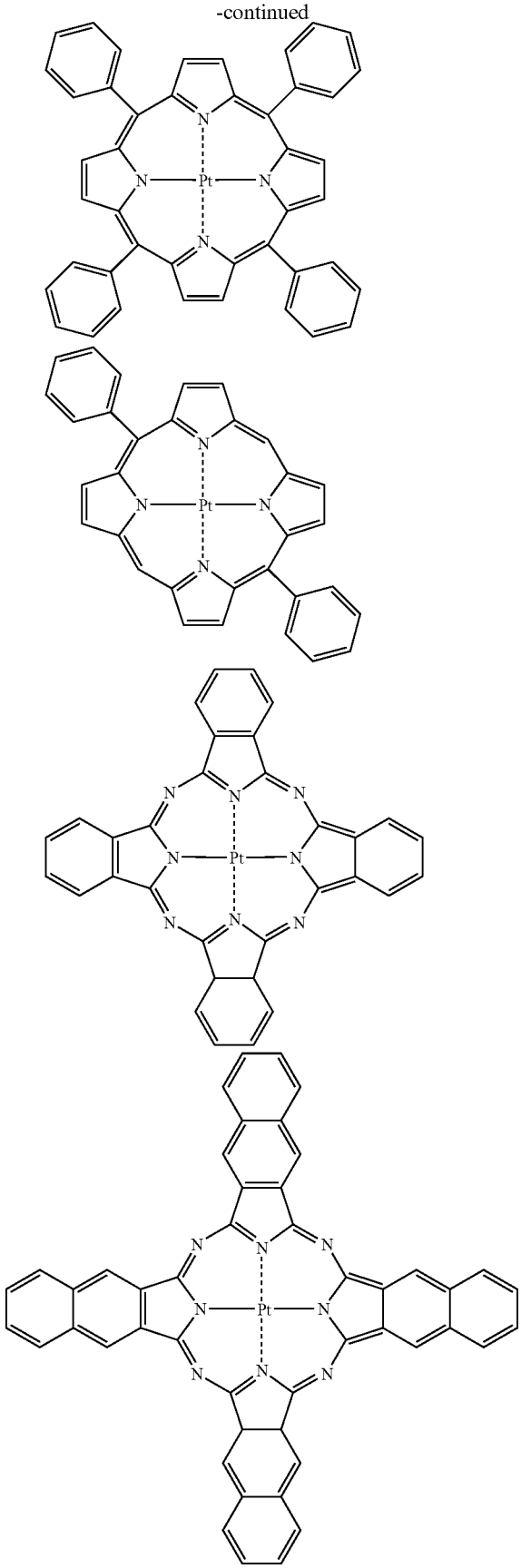

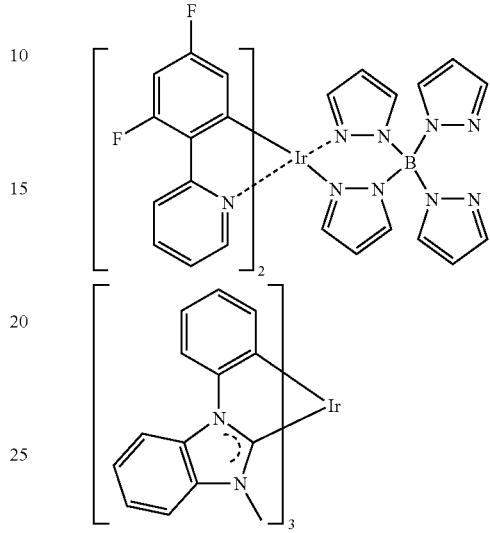

[Chemical Formula 58]

In addition, phosphorescent organometallic complexes containing a metal selected from metals belonging to Group 7 to Group 11 of the periodic table also include the following compound:

The molecular weight of such a phosphorescent dopant material is usually 4,000 or less, preferably 3,000 or less, and more preferably 2,000 or less and is usually 200 or more, preferably 300 or more, and more preferably 400 or more. If the molecular weight exceeds the upper limit, there might result seriously reduced sublimability which can cause troubles when vapor deposition is employed in the production of an electroluminescent device or might result a decreased solubility in an organic solvent which makes it difficult to conduct high purification (removal of substances causing deterioration) with an increase in the amount of impurities formed in the synthesizing steps. On the other hand, if the molecular weight is less than the lower limit, there results a reduced glass transition temperature, a reduced melting point, and a reduced gasification temperature, which may seriously spoil heat resistance.

When two or more different dopant materials are used, the hole blocking material in the hole blocking layer preferably has an oxidation potential greater than the greatest oxidation potential of the two or more different dopant materials.

When a light-emitting layer uses such an organometallic complex as a dopant material and emits phosphorescence, each of the organic compounds according to the present invention can be used alone or in combination as a host material for the light-emitting layer. The host material for use in the light-emitting layer giving phosphorescent emission may further include, in combination with one or more organic compounds according to the present invention, one or more of the materials having been described as host materials to be used in the light-emitting layer giving fluorescent emission (including aromatic amine compounds), carbazole derivatives such as 4,4'-N,N'-dicarbazolebiphenyl (PCT International Publication Number WO 00/70655), tris(8-hydroxyquinoline)aluminum (U.S. Pat. No. 6,303,238), 2,2',2"-(1,3,5-benzenetolyl)tris[1-phenyl-1H-benzimidazole] (Appl. Phys. Lett., vol. 78, p. 1622, 2001), and polyvinylcarbazoles (Japanese Unexamined Patent Application Publication No. 2001-257076). The content of such other host materials, if contained in the light-emitting layer in combination with one or more organic compounds according to the present invention, is preferably 50 percent by weight or less relative to the organic compounds according to the present invention.

The amount of the organometallic complex to be contained as a dopant material in the light-emitting layer is preferably 0.1 percent by weight or more, and is preferably 30 percent by weight or less. If the amount is less than the lower limit, the complex might fail to contribute to the improvement of the luminous efficiency of the device whereas, if the complex exceeds the upper limit, there arises the possibility that concentration quenching takes place due typically to formation of a dimmer of the organometallic complex, leading to reduction of luminous efficiency.

There is a tendency that the amount of a dopant material in the light-emitting layer showing phosphorescent light emission is preferably somewhat larger than the amount of a fluorescent dye contained in the light-emitting layer in a device utilizing conventional fluorescence (singlet). When a fluorescent dye is contained in the light-emitting layer together with a phosphorescent dopant material, the amount of the fluorescent dye is preferably 0.05 percent by weight or more, more preferably 0.1 percent by weight or more, and is preferably 10 percent by weight or less, more preferably 3 percent by weight or less.

The thickness of the light-emitting layer 5 is usually 3 nm or more, preferably 5 nm or more, and is usually 200 nm or less, preferably 100 nm or less.

The light-emitting layer 5 can also be formed in the same manner as with the hole transport layer 4.

An organic compound according to the present invention as a host material for the light-emitting layer may be doped with the above-mentioned fluorescent dye and/or the phosphorescent dye (phosphorescent dopant material) as a dopant material, for example, in the following manner.

When the light-emitting layer 5 is formed by coating, a coating composition is prepared by dissolving the organic compound according to the present invention, a dopant material, and, as needed, a binder resin which does not function as a trap of electrons or as a emitted light-quenching agent in a solvent, and the coating composition is applied to the hole transport layer 4 typically by spin coating, followed by drying to form the light-emitting layer 5. Examples of the binder resin include polycarbonates, polyarylates, and polyesters. When added in a large amount, the binder resin may reduce the hole/electron mobility and, therefore, a smaller amount of the binder resin is desirable, with 50 percent by weight or less in terms of content in the light-emitting layer being preferred.

When the light-emitting layer 5 is formed by vacuum deposition, an organic compound according to the present invention is placed in a crucible placed in a vacuum container, a dopant material is placed in a different crucible, and the inside of the vacuum container is evacuated to a degree of vacuum of about $10^{-4}$ Torr using a proper vacuum pump. Thereafter, the crucibles are heated at the same time to evaporate them and form a layer on the substrate which is placed facing the crucibles. As an alternative process, the above-mentioned materials are mixed in a predetermined ratio to yield a mixture and the mixture is evaporated using one crucible.

When each dopant material is introduced into the light-emitting layer 5 by doping, it is uniformly distributed in a thickness direction of the light-emitting layer. However, there may be a concentration distribution of the dopant material in the thickness direction. For example, doping may be conducted, only in the vicinity of the interface with the hole transport layer 4 or, reversely, may be conducted in the vicinity of the hole blocking layer 6.

The light-emitting layer 5 can be formed in the same manner as with the hole transport layer 4 but, usually, is formed by vacuum deposition.

The light-emitting layer 5 may further contain other components in addition to the above-mentioned components, within ranges not adversely affecting the performance according to the present invention.

Hole Blocking Layer

In the device shown in FIG. 1, a hole blocking layer 6 is arranged on the light-emitting layer 5 so as to be in contact with one of the interfaces of the light-emitting layer 5 near to the cathode.

The hole blocking layer 6 is preferably formed by a compound which serves to prevent holes migrating from the hole transport layer 4 from reaching the cathode 8 and which can effectively transport electrons injected from the cathode 8 toward the light-emitting layer 5. Physical properties required for a material constituting the hole blocking layer 6 include a high electron mobility and a low hole mobility. The hole blocking layer 6 has the function of confining holes and electrons within the light-emitting layer 5 to thereby improve luminous efficiency.

The ionization potential of the hole blocking layer 6 to be arranged in an organic electroluminescent device according to the present invention is preferably larger than the ionization potential of the light-emitting layer 5 (when the light-emitting layer 5 contains both a host material and a dopant material, the ionization potential of the host material) by 0.1 eV or more. The ionization potential is defined in terms of energy necessary to release an electron at HOMO (highest occupied molecular orbital) level of a substance to a vacuum level. The ionization potential can be directly defined by the photo-electron spectrometry. Alternatively, it can be determined by correcting an electrochemically measured oxidation potential based on a reference electrode. In the latter process using, for example, a saturated calomel electrode (SCE) as the reference electrode, the ionization potential is defined according to the following equation (Molecular Semiconductors, Springer-Verlag, 1985, p. 98):

Ionization potential=(Oxidation potential (vs. SCE))+ 4.3 eV

Further, electron affinity (EA) of the hole blocking layer 6 to be arranged in an organic electroluminescent device according to the present invention is preferably equal to or more than the electron affinity of the light-emitting layer 5 (when the light-emitting layer 5 contains both a host material and a dopant material, the electron affinity of the host material). The electron affinity is defined in terms of energy released when an electron in a vacuum level falls to LUMO (lowest unoccupied molecular orbital) level to stabilize with taking the vacuum level as a standard as with the ionization potential. The electron affinity is similarly determined by subtracting an optical band gap from the ionization potential or determining from an electrochemical reduction potential according to the following equation:

Electron affinity=(Reduction potential (vs. SCE))+4.3 eV

Therefore, the hole blocking layer 6 to be arranged in an organic electroluminescent device according to the present invention can also be expressed as follows using oxidation potential and reduction potential:

(Oxidation potential of the hole blocking material)− (Oxidation potential of the light-emitting layer material)≧0.1 V (Reduction potential of the hole blocking material)≧ (Reduction potential of the light-emitting layer material)

Further, in a device having an electron transport layer 7 to be described below, the electron affinity of the hole blocking layer 6 is preferably equal to or lower than the electron affinity of the electron transport layer 7. Accordingly, the following condition is preferably satisfied:

(Reduction potential of the electron transporting material)≧(Reduction potential of the hole blocking material)≧(Reduction potential of the light-emitting layer material)

In this condition, when two or more different electron transporting materials, two or more different hole blocking materials, or two or more different light-emitting layer materials are used, one having the smallest reduction potential is employed for comparison in the formula; and when the light-emitting layer 5 contains both host materials and dopant materials, one of the host materials having the smallest reduction potential is employed for comparison in the formula.

A preferred example of hole blocking materials satisfying such conditions includes a mixed ligand complex represented by following Formula (VII):

[Chemical Formula 59]

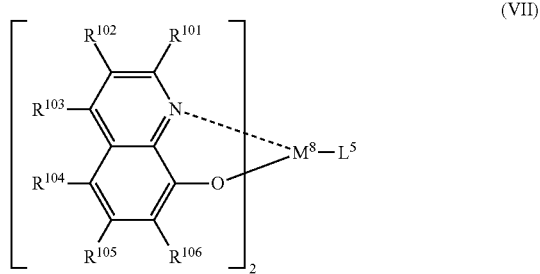

(VII)

wherein $R^{101}$, $R^{102}$, $R^{103}$, $R^{104}$, $R^{105}$, and $R^{106}$ each independently represent a hydrogen atom or an arbitrary substituent; $M^8$ represents a metal atom selected from aluminum, gallium, and indium; and $L^5$ is represented by any one of following Formulae (VIIa), (VIIb), and (VIIc):

[Chemical Formula 60]

—O—Ar$^{51}$ (VIIa)

—O—C(=O)—Ar$^{52}$ (VIIb)

—O—Z$^3$(Ar$^{53}$)(Ar$^{54}$)—Ar$^{55}$ (VIIc)

wherein Ar$^{51}$, Ar$^{52}$, Ar$^{53}$, Ar$^{54}$, and Ar$^{55}$ each independently represent an aromatic hydrocarbon group which may be substituted or an aromatic heterocyclic group which may be substituted; and $Z^3$ represents silicon or germanium.

In Formula (VII), $R^{101}$ to $R^{106}$ each independently represent a hydrogen atom or an arbitrary substituent. Preferred examples of $R^{101}$ to $R^{106}$ include hydrogen atom; halogen atoms such as chlorine and bromine; alkyl groups having one to six carbon atoms, such as methyl group and ethyl group; aralkyl groups such as benzyl group; alkenyl groups having two to six carbon atoms, such as vinyl group; cyano group; amino groups; acyl groups; alkoxy groups having one to six carbon atoms, such as methoxy group and ethoxy group; alkoxycarbonyl groups having two to six carbon atoms, such as methoxycarbonyl group and ethoxycarbonyl group; carboxyl group; aryloxy groups such as phenoxy group and benzyloxy group; dialkylamino groups such as diethylamino group and diisopropylamino group; diaralkylamino groups such as dibenzylamino group and diphenethylamino group; α-haloalkyl groups such as trifluoromethyl group; hydroxy group; aromatic hydrocarbon groups which may be substituted, such as phenyl group and naphthyl group; and aromatic heterocyclic groups which may be substituted, such as thienyl group and pyridyl group.

Examples of substituents which the aromatic hydrocarbon groups and aromatic heterocyclic groups may have include halogen atoms such as fluorine atom; alkyl groups having one to six carbon atoms, such as methyl group and ethyl group; alkenyl groups having two to six carbon atoms, such as vinyl group; alkoxycarbonyl groups having two to six carbon atoms, such as methoxycarbonyl group and ethoxycarbonyl group; alkoxy groups having one to six carbon atoms, such as methoxy group and ethoxy group; aryloxy groups such as phenoxy group and benzyloxy group; dialkylamino groups such as dimethylamino group and diethylamino group; acyl groups such as acetyl group; haloalkyl groups such as trifluoromethyl group; and cyano group.

More preferred examples of $R^{101}$ to $R^{106}$ include hydrogen atom, alkyl groups, halogen atoms, and cyano group. As $R^{104}$, cyano group is especially preferred.

Specific examples of Ar$^{51}$ to Ar$^{55}$ in Formulae (VIIa), (VIIb), and (VIIc) include aromatic hydrocarbon groups which may be substituted, such as phenyl group, biphenyl group, and naphthyl group; and aromatic heterocyclic groups which may be substituted, such as thienyl group and pyridyl group.

Preferred specific examples of the compounds represented by Formula (VII) will be illustrated below, which are, however, by no means limitative.

[Chemical Formula 61]

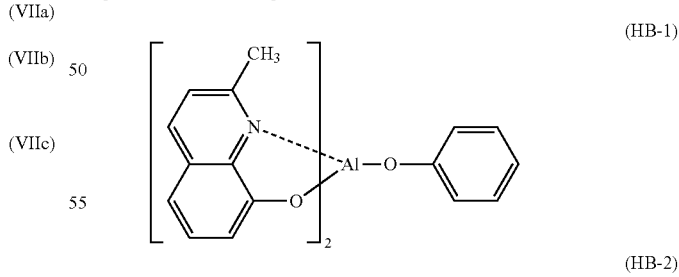

(HB-1)

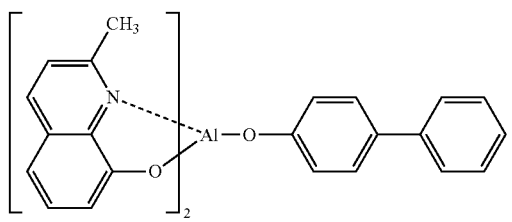

(HB-2)

(HB-3)
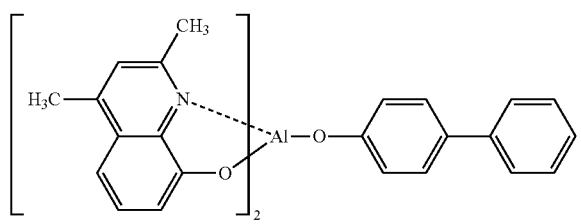
(HB-4)
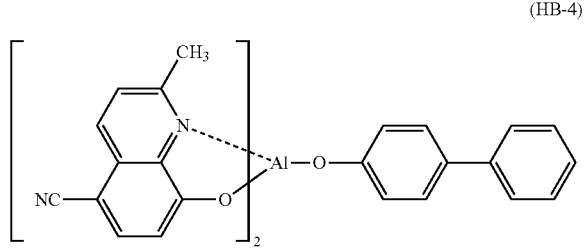
(HB-5)
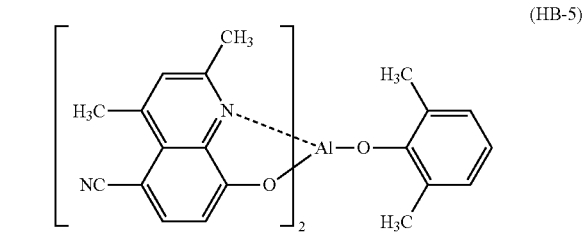
(HB-6)
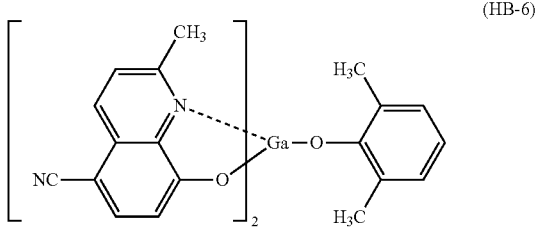
(HB-7)
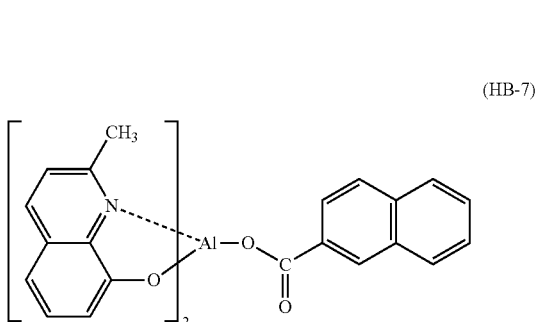
(HB-8)
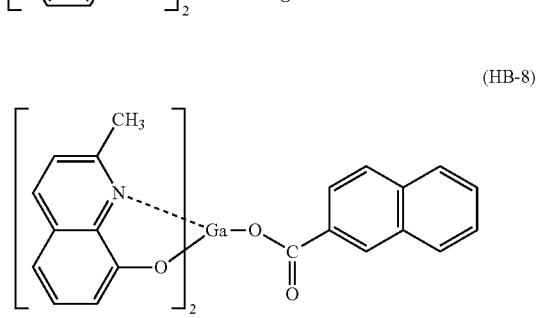
(HB-9)
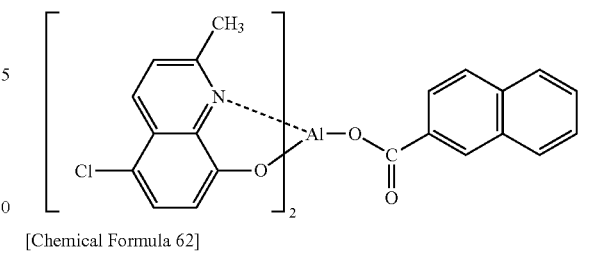
(HB-10)
(HB-11)
[Chemical Formula 62]
(HB-12)
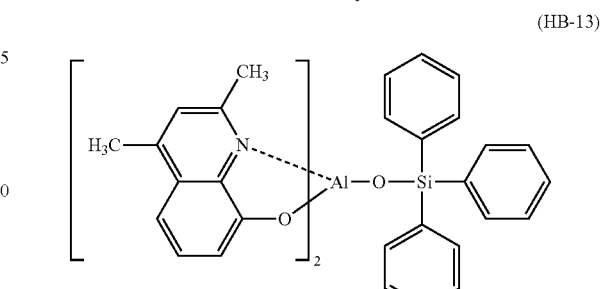
(HB-13)
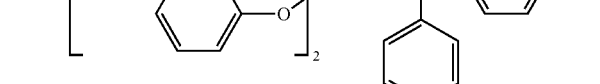
(HB-14)
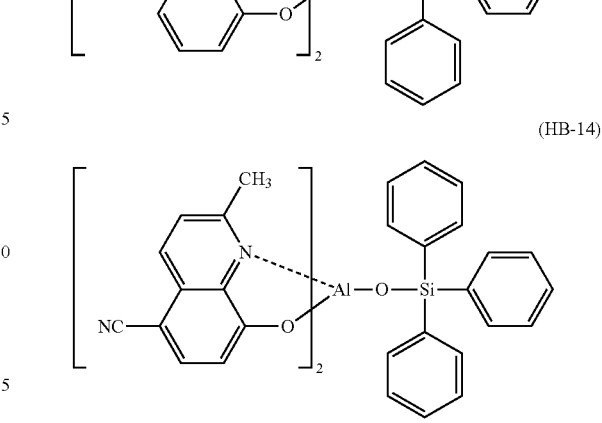

(HB-15)
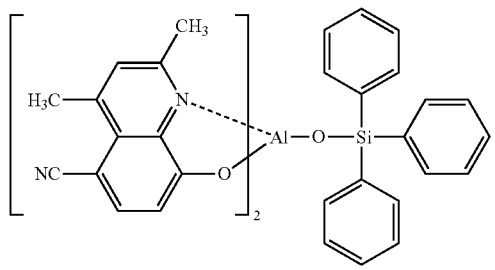

(HB-16)
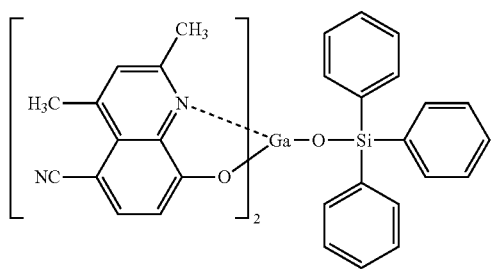

(HB-17)
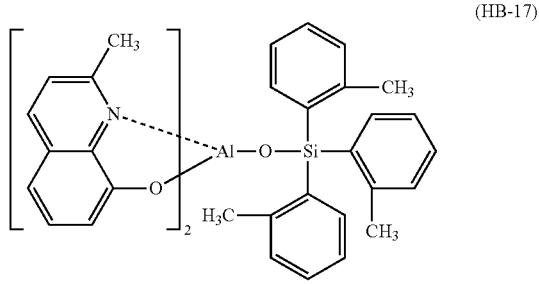

(HB-18)
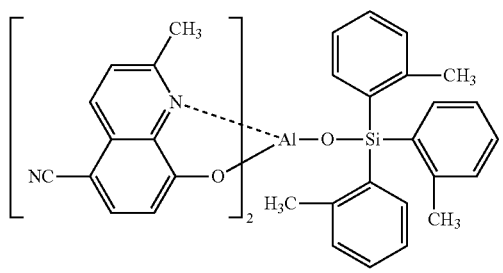

(HB-19)
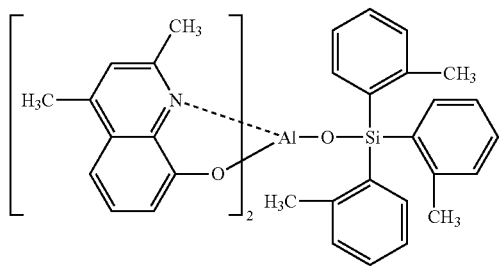

(HB-20)
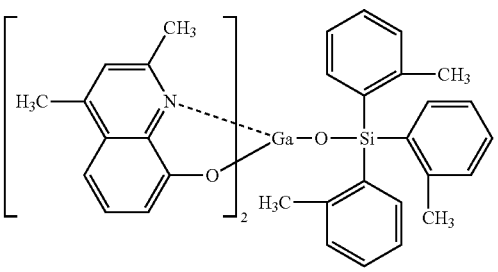

Each of these compounds can be used alone or in combination according to necessity in the hole blocking layer 6.

Such hole blocking materials also include, in addition to the mixed ligand complexes represented by Formula (VII), compounds having at least one residue derived from 1,2,4-triazole ring and represented by the following structural formula:

[Chemical Formula 63]

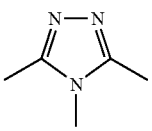

Specific examples of the compounds having at least one residue derived from 1,2,4-triazole ring and represented by the structural formula will be illustrated below, which are, however, by no means limitative.

[Chemical Formula 64]

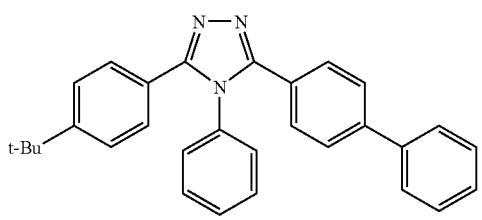

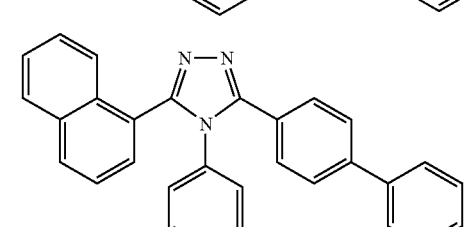

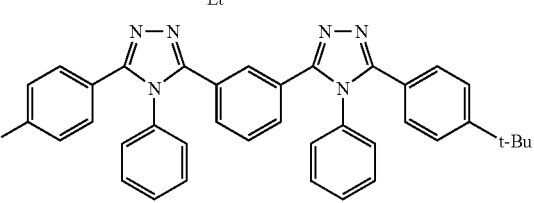

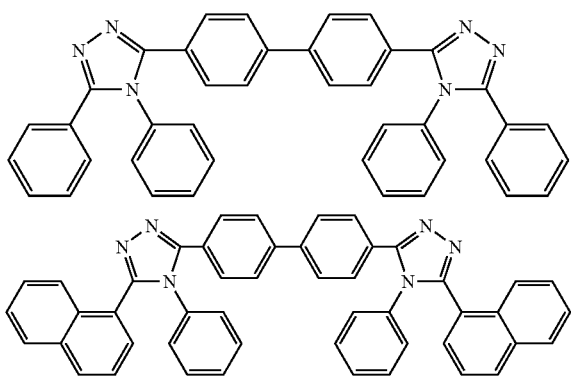

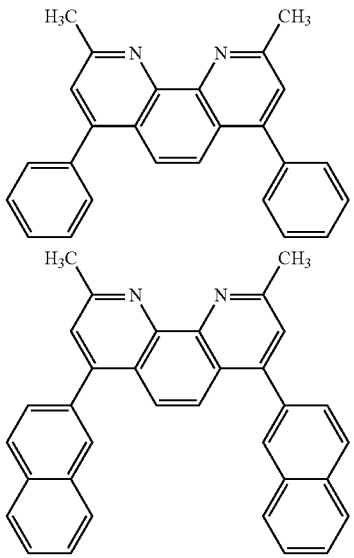

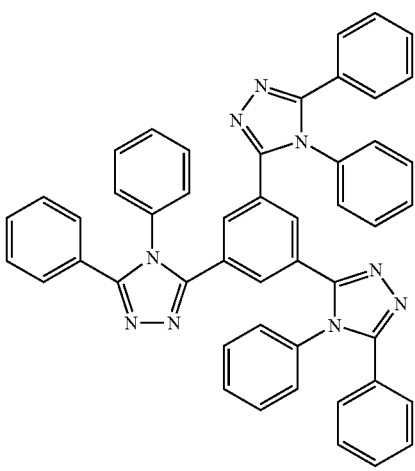

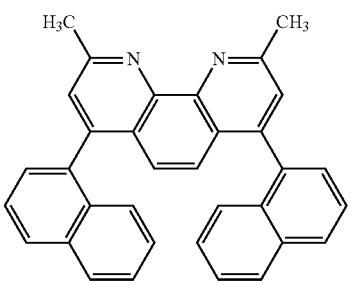

Hole blocking materials further include compounds having at least one phenanthroline ring represented by the following structural formula:

[Chemical Formula 65]

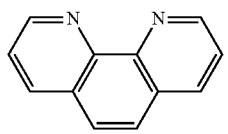

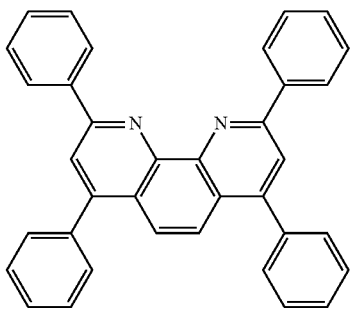

Specific examples of the compounds having at least one phenanthroline ring represented by the structural formula will be illustrated below, which are, however, by no means limitative.

[Chemical Formula 66]

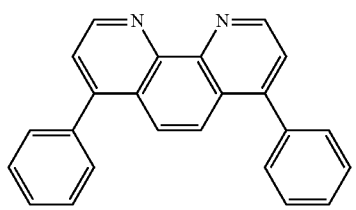

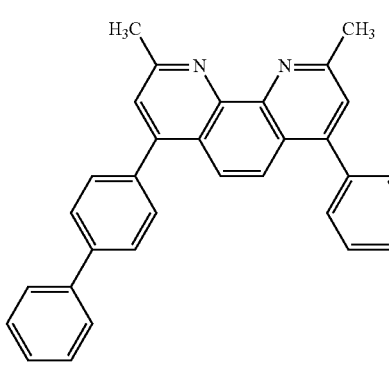

A compound including a pyridine ring intramolecularly having substituents at the 2-, 4-, and 6-positions is also preferably used as a hole blocking material. Specific examples of such compounds are as follows.

99
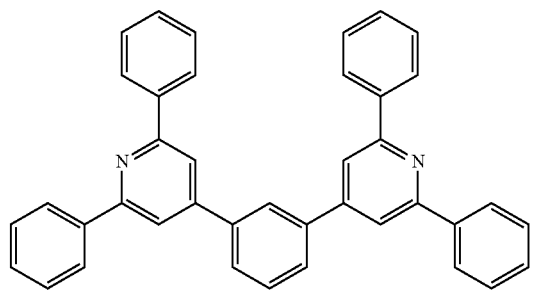
100
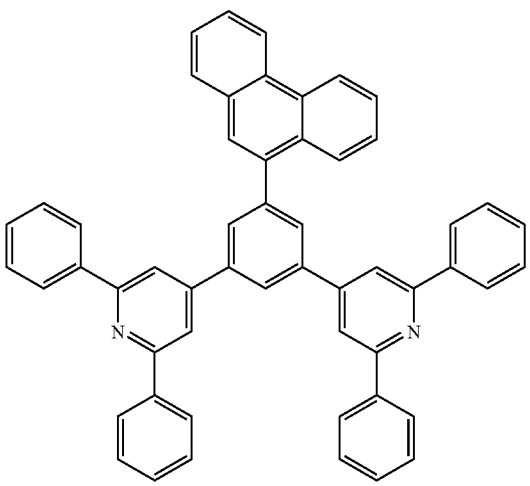
[Chemical Formula 67]
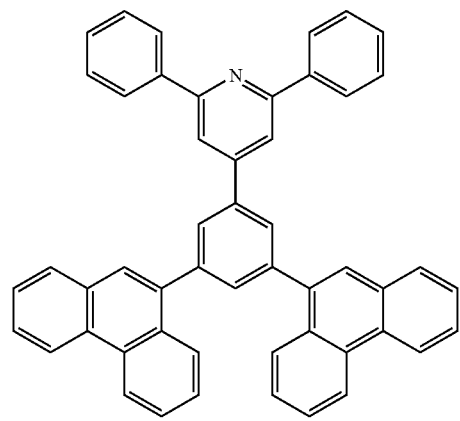
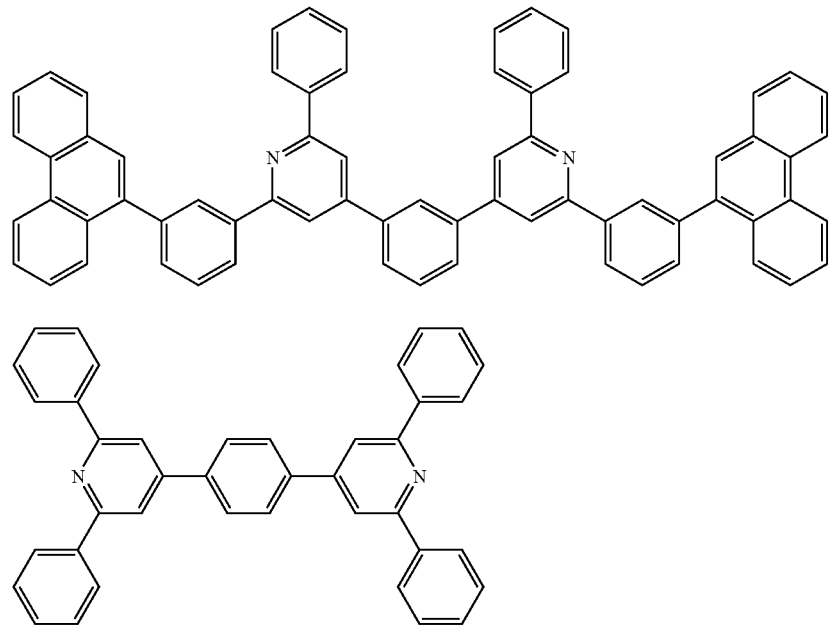

-continued
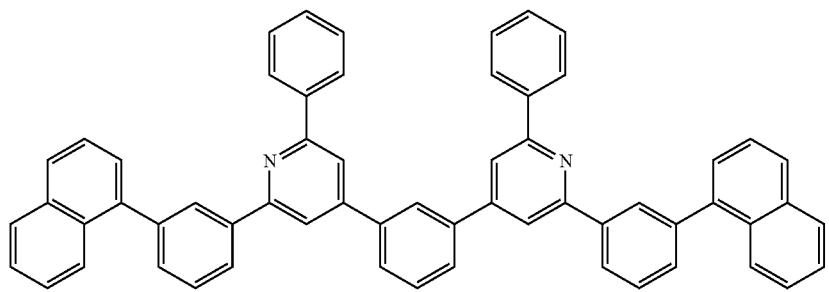
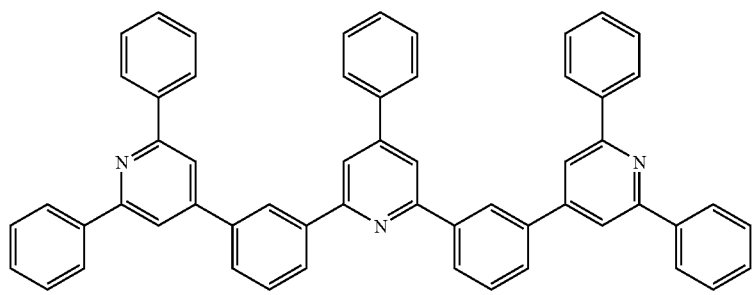
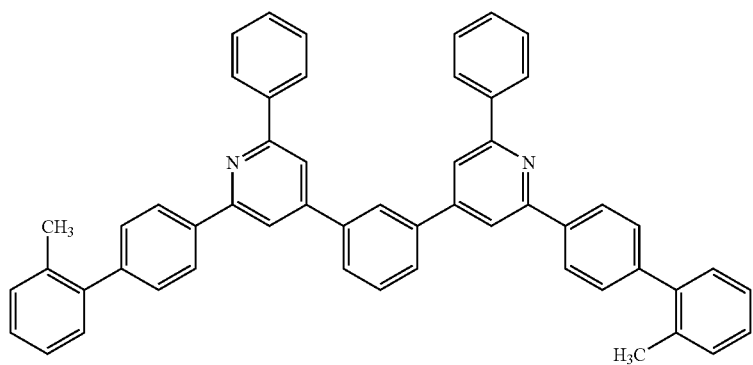
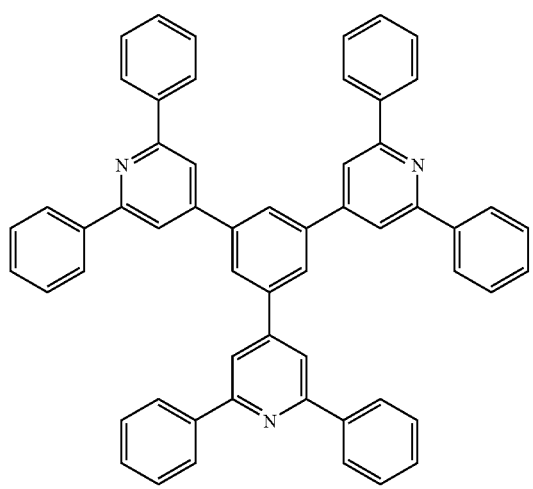

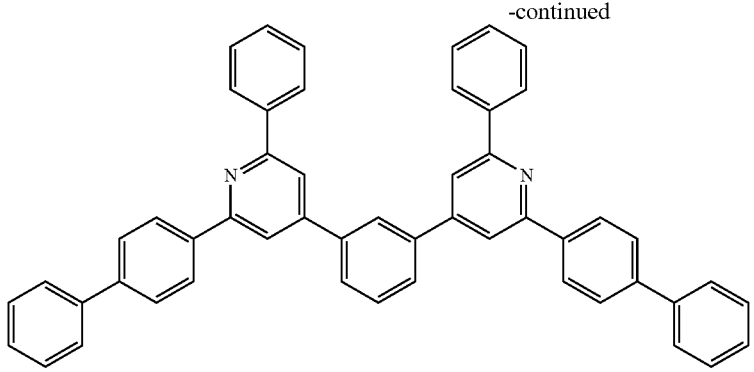

The thickness of the hole blocking layer 6 is generally 0.3 nm or more, preferably 0.5 nm or more and is generally 100 nm or less, preferably 50 nm or less.

The hole blocking layer 6 can be formed in the same manner as with the hole transport layer 4, but it is generally formed by vacuum deposition.

An organic electroluminescent device according to the present invention, however, can exhibit sufficiently satisfactory properties even when no hole blocking layer is provided, as described in after-mentioned Examples. This is because the organic compound for use in the present invention is excellent as a host material in a light-emitting layer of such an organic electroluminescent device.

Cathode

The cathode 8 serves to inject electrons into the light-emitting layer 5 through the hole blocking layer 6. As the material to be used as the cathode 8, those materials which are used for the anode 2 may be employed but, in order to inject electrons with a high efficiency, metals having a low work function are preferred. Thus, suitable metals such as tin, magnesium, indium, calcium, aluminum and silver or alloys thereof are used. Specific examples thereof include electrodes of alloys having a low work function, such as a magnesium-silver alloy, a magnesium-indium alloy and a aluminum-lithium alloy.

The thickness of the cathode 8 is generally as with the anode 2.

A metal layer having a high work function and stable in the atmosphere may be arranged on the cathode 8 in order to protect the cathode 8 including such a metal having a low work function. This improves the stability of the device. For this purpose, metals such as aluminum, silver, copper, nickel, chromium, gold and platinum are used.

Further, in order to improve efficiency of the device, it is also an effective technique to arrange an extremely thin insulating film of LiF, $MgF_2$ or $Li_2O$ at the interface between the cathode 8 and the light-emitting layer 5 or the electron transport layer 7 (Appl. Phys. Lett., vol. 70, p. 152, 1997; Japanese Unexamined Patent Application Publication No. 10-74586; and IEEE Trans. Electron. Devices, vol. 44, p. 1245, 1997).

Electron Transport Layer

For further improving luminous efficiency of the device, an electron transport layer 7 may be arranged between the hole blocking layer 6 and the cathode 8 as shown in FIGS. 2 and 3. The electron transport layer 7 is formed from a compound which can efficiently transport electrons injected from the cathode 8 toward the hole blocking layer 6 between the energized electrodes.

Examples of the material satisfying such conditions include metal complexes such as aluminum complex of 8-hydroxyquinoline (Japanese Unexamined Patent Application Publication No. 59-194393); metal complexes of 10-hydroxybenzo[h]quinoline; oxadiazole derivatives; distyrylbiphenyl derivatives; silole derivatives; metal complexes of 3- or 5-hydroxyflavone; metal complexes of benzoxazole; metal complexes of benzothiazole; trisbenzimidazolylbenzene (U.S. Pat. No. 5,645,948), quinoxaline compounds (Japanese Unexamined Patent Application Publication No. 6-207169); phenanthroline derivatives (Japanese Unexamined Patent Application Publication No. 5-331459); 2-t-butyl-9,10-N,N'-dicyanoanthraquinonediimine; n-type hydrogenated amorphous silicon carbide; n-type zinc sulfide; and n-type zinc selenide.

It is preferred to dope the electron transporting material described above with an alkali metal (described typically in Japanese Unexamined Patent Application Publications No. 10-270171, No. 2002-100478, and No. 2002-100482) since it serves to improve the electron transporting ability.

When the electron transport layer 7 is arranged, the hole blocking layer 6 preferably has an electron affinity equal to or lower than the electron affinity of the electron transport layer 7.

The reduction potentials of the light-emitting layer material for use in the light-emitting layer 5, the hole blocking material in the hole blocking layer 6, and the electron transporting material in the electron transport layer preferably satisfy the following condition, for adjusting light emitting regions and reducing the drive voltage.

(Reduction potential of the electron transporting material)≧(Reduction potential of the hole blocking material)≧(Reduction potential of the light-emitting layer material)

In this connection, when two or more different electron transporting materials, two or more different hole blocking materials, or two or more different light-emitting layer materials are used, one having the smallest reduction potential is used for comparison in the formula; and when the light-emitting layer 5 contains both host materials and dopant materials, one of the host materials having the smallest reduction potential is used for comparison in the formula.

The above-mentioned hole blocking materials may be used in the electron transport layer 7. In this case, each of the hole blocking materials can be used alone or in combination to form the electron transport layer 7.

The thickness of the electron transport layer 7 is generally 5 nm or more, preferably 10 nm or more and is generally 200 nm or less, preferably 100 nm or less.

The electron transport layer 7 may be formed on the hole blocking layer 6 by coating or vacuum deposition, in the same manner as with the hole transport layer 4. The electron transport layer 7 is generally formed by vacuum deposition.

In this connection, the electron transport layer 7 may be arranged between the light-emitting layer 5 and the cathode 8, without arranging the hole blocking layer 6.

Hole Injection Layer

A hole injection layer 3 may be arranged between the hole transport layer 4 and the anode 2 (FIGS. 3 and 4), for further improving efficiency of injecting holes and improving adhesion of the whole organic layers onto the anode 2. Arrangement of the hole injection layer 3 serves to provide the effect of reducing the initial drive voltage of the device and, at the same time, depressing an increase in voltage upon continuous driving of the device at a constant current.

As to requirements for materials to be used in the hole injection layer 3, the materials are required to have a good contact with the anode 2, form a uniform thin film, and be thermally stable. Specifically, they preferably have a high melting point and a high glass transition temperature, with the melting point being preferably 300° C. or higher, and the glass transition temperature being 100° C. or higher. In addition, the materials are required to have a sufficiently low ionization potential to facilitate injection of holes from the anode 2 and have a large hole mobility.

As materials for the hole injection layer 3 to be arranged for this purpose, there have been reported organic compounds such as porphyrin derivatives or phthalocyanine derivatives (Japanese Unexamined Patent Application Publication No. 63-295695), hydrazone compounds, alkoxy-substituted aromatic diamine derivatives, p-(9-anthryl)-N,N'-di-p-tolylaniline, polythienylenevinylenes and poly-p-phenylenevinylenes, polyanilines (Appl. Phys. Lett., vol. 64, p. 1245, 1994), polythiophenes (Optical Materials, vol. 9, p. 125, 1998) and star-burst type aromatic triamines (Japanese Unexamined Patent Application Publication No. 4-308688); sputtered carbon films (Synth. Met., vol. 91, p. 73, 1997); and metal oxides such as vanadium oxide, ruthenium oxide, and molybdenum oxide (J. Phys. D, vol. 29, p. 2750, 1996).

There may also be employed a layer containing a hole injecting and transporting, low-molecular organic compound and an electron acceptive compound (described typically in Japanese Unexamined Patent Application Publications No. 11-251067 and No. 2000-159221), a layer including an aromatic amino group-containing, non-conjugated high-molecular compound doped with, as needed, an electron acceptive compound (e.g., Japanese Unexamined Patent Application Publications No. 11-135262, No. 11-283750, No. 2000-36390, No. 2000-150168, and No. 2001-223084; and POT International Publication Number WO 97/33193) and a layer containing a conductive polymer such as a polythiophene (Japanese Unexamined Patent Application Publication No. 10-92584) which, however, are not limitative at all.

As materials for the hole injection layer 3, either of low-molecular compounds and high-molecular compounds may be used.

Of the low-molecular compounds, porphine compounds and phthalocyanine compounds are popularly used. These compounds may have a central metal or may be metal-free. Preferred examples of these compounds include the following compounds:
porphine,
5,10,15,20-tetraphenyl-21H,23H-porphine,
5,10,15,20-tetraphenyl-21H,23H-porphine cobalt(II),
5,10,15,20-tetraphenyl-21H,23H-porphine copper(II),
5,10,15,20-tetraphenyl-21H,23H-porphine zinc(II),
5,10,15,20-tetraphenyl-21H,23H-porphine vanadium(IV) oxide,
5,10,15,20-tetra(4-pyridyl)-21H,23H-porphine,
29H,31H-phthalocyanine,
copper(II) phthalocyanine,
zinc(II) phthalocyanine,
titanium phthalocyanine oxide,
magnesium phthalocyanine,
lead phthalocyanine, and
copper(II) 4,4'4'',4'''-tetraaza-29H,31H-phthalocyanine A thin film constituting the hole injection layer 3 may be formed in the same manner as with the hole transport layer 4. When an inorganic material is used, the thin film can also be formed by sputtering, electron-beam evaporation, or plasma chemical vapor deposition (plasma CVD).

When formed from a low-molecular compound, the thickness of the hole injection layer 3 is such that the lower limit is generally about 3 nm, preferably about 10 nm, and the upper limit is generally about 100 nm, preferably about 50 nm.

When a polymer compound is used as a material for the hole injection layer 3, the hole injection layer 3 may be formed, for example, by dissolving in a solvent the polymer compound, the electron acceptive compound and, as needed, a binder resin and/or an additive such as a coating property-improving agent (e.g., a leveling agent) which does not function as a trap of holes, for example, to prepare a coating composition, and applying the coating composition to the anode 2 according to a common coating procedure such as spray coating, printing, spin coating, dip coating, or die coating or by an ink jet process, followed by drying to form the hole injection layer 3. Examples of the binder resin include polycarbonates, polyarylates, and polyesters. When added in a large amount, the binder resin might reduce the hole mobility, and hence the amount is preferably small, with 50 percent by weight or less in terms of content in the hole injection layer 3 being usually preferred.

It is also possible to previously form a thin film on a medium such as a film, a supporting substrate or a roll according to the thin film-forming process and transferring the thin film from the medium onto the anode 2 by applying heat or pressure to thereby form a thin film.

The lower limit of the thickness of the hole injection layer 3 formed as described hereinbefore is usually about 5 nm, preferably about 10 nm, and the upper limit is usually about 1,000 nm, preferably about 500 nm.

Layer Structure

An organic electroluminescent device according to the present invention can have a reverse structure to that shown in FIG. 1. In the reverse structure, on a substrate 1, there are arranged a cathode 8, a hole blocking layer 6, a light-emitting layer 5, a hole transport layer 4, and an anode 2 in this order. An organic electroluminescent device according to the present invention can also be arranged between two substrates, one of which is optically highly transparent, as described above. Likewise, the components can be laminated in reverse order to those described in FIGS. 2 to 4, respectively. The layer structures shown in FIGS. 1 to 4 may each further include any arbitrary layer or layers, in addition to the layers mentioned above, within ranges not departing from the scope and spirit of the present invention. In addition, modifications and variations can be made as appropriate. For example, a layer structure can be simplified by arranging a layer having the functions of two or more of the above-mentioned layers.

Further, it is possible to employ a top emission structure or to use transparent electrodes as the cathode and the anode to prepare a transparent device or, further, to employ a layer structure wherein a plurality of the layer structures shown in FIG. 1 are stacked (a structure wherein a plurality of the light-emitting units are stacked). In this case, V₂O₅, for example, is preferably used as a charge generating layer (CGL) instead of the interface layers (when ITO and aluminum (Al) are used as the anode and the cathode, respectively, the two layers of the anode and the cathode) between the units (light-emitting units). This serves to reduce barrier between the units, thus being more preferred in view of luminous efficiency and drive voltage.

The present invention can be applied to any of structures of organic luminescent devices, such as a structure in which the organic electroluminescent device includes a single device, a structure which includes devices arranged in an array form, and a structure wherein the anode and the cathode are arranged in an X-Y matrix pattern.

EXAMPLES

Next, the present invention will be illustrated in further detail with reference to several examples below, which, however, are not limitative at all, as long as not exceeding the scope and the spirit of the present invention.

[Synthesis Examples of Organic Compounds]

Organic compounds useable as organic compounds according to the present invention and charge transporting materials according to the present invention may be synthetically prepared, for example, according to the following Synthesis Examples. In the following examples, the glass transition temperature was determined by differentiation scanning calorimetry (DSC), the gasification temperature was determined by thermogravimetry/differential thermal analysis (TG-DTA), and the melting point was determined by differentiation scanning calorimetry (DSC) or thermogravimetry/differential thermal analysis (TG-DTA).

Synthesis Example 1

Syntheses of Target Compounds 1 to 3

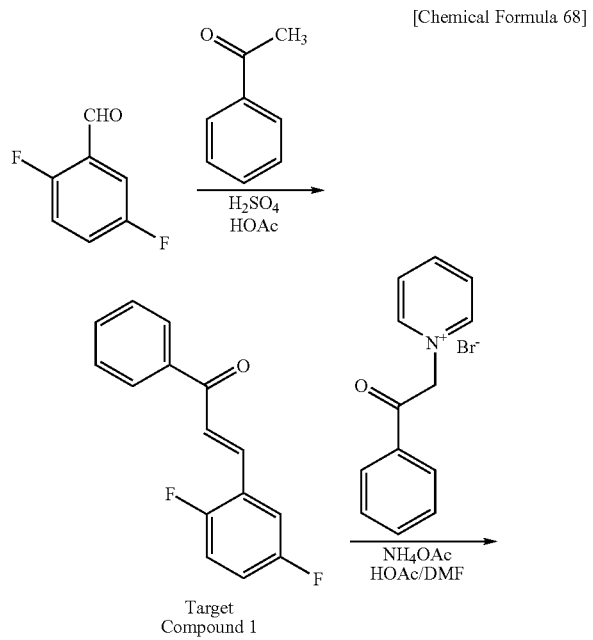

[Chemical Formula 68]

Target Compound 1

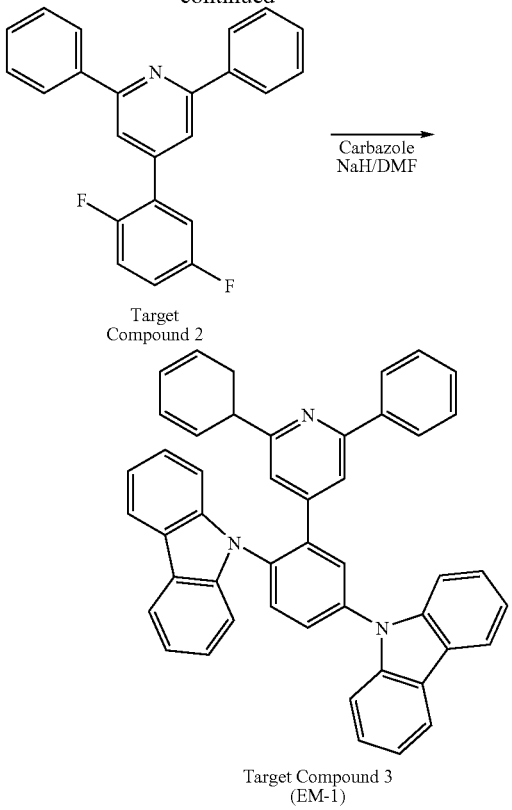

Target Compound 2

Target Compound 3 (EM-1)

Concentrated sulfuric acid (11.6 ml) was added to a mixture as a solution of 2,5-difluorobenzaldehyde (10.24 g), acetophenone (8.66 g), and acetic acid (100 ml) in a dry air atmosphere, followed by stirring at 35° C. for seven hours. The mixture was combined with methanol (5 ml) and water (150 ml) to yield a precipitate, and the precipitate was collected by filtration and washed with water. This was washed in a suspended state in methanol with heating under reflux and thereby yielded Target Compound 1 (10.94 g).

Target Compound 1 (6.34 g), 1-phenacylpyridinium bromide (10.83 g), ammonium acetate (50.0 g), and acetic acid (220 ml), and N,N-dimethylformamide (220 ml) were stirred with heating under reflux in a dry air atmosphere for six hours. The resulting mixture was combined with water (440 ml) to yield a precipitate, and the precipitate was collected by filtration and washed with methanol. This was purified by washing in a suspended state in methanol and reprecipitation from chloroform-methanol and thereby yielded Target Compound 2 (2.71 g).

Carbazole (3.10 g) was added to a suspension of sodium hydride (55%, 0.81 g) in anhydrous N,N-dimethylformamide (50 ml) in a nitrogen stream, followed by stirring at 80° C. for sixty minutes. The resulting mixture was combined with Target Compound 2 (2.44 g) and was stirred with heating under reflux for three hours. This was cooled to ice temperature, was combined with 50 ml of water to yield a precipitate, and the precipitate was separated by filtration and washed with methanol to yield a solid. The solid was extracted with chloroform, washed in a suspended state in ethanol with heating under reflux, purified by silica gel column chromatography, and thereby yielded Target Compound 3 (EM-1) (4.25 g).

This was identified as Target Compound 3 through desorption electron ionization-mass spectrometry (DEI-MS) (m/z=637 (M⁺)).

This compound had a glass transition temperature of 116° C., a vaporization temperature of 456° C., and a melting point of 262° C.

Synthesis Example 2

Syntheses of Target Compounds 4 to 7

[Chemical Formula 69]

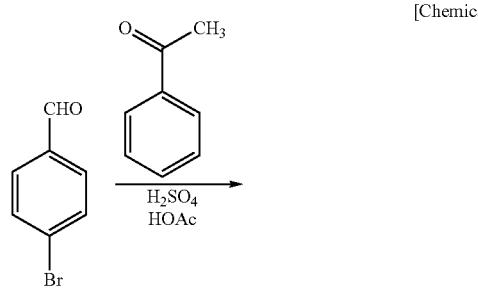

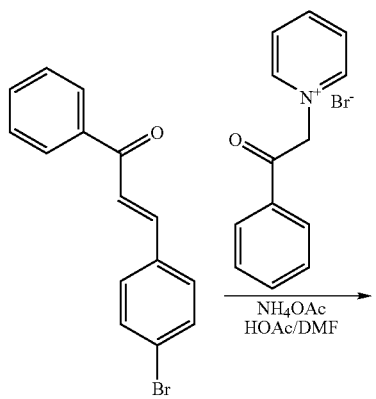

Target Compound 4

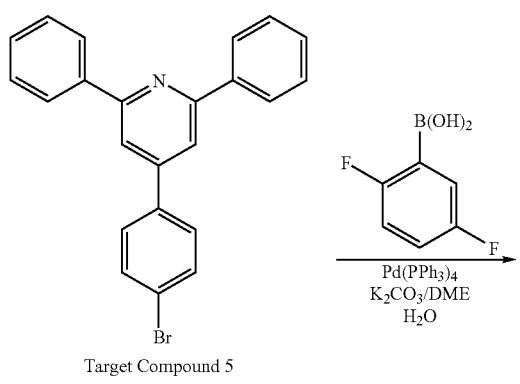

Target Compound 5

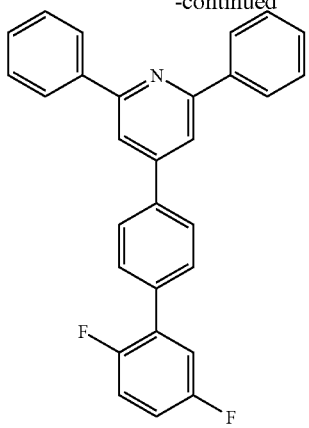

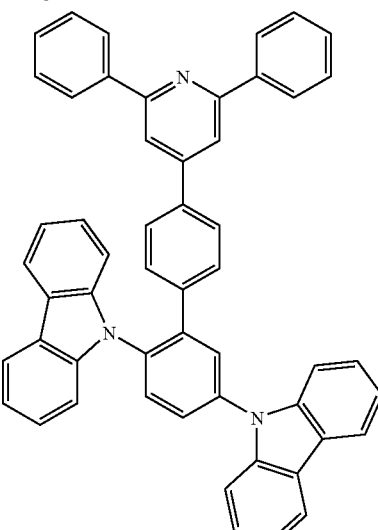

Target Compound 6

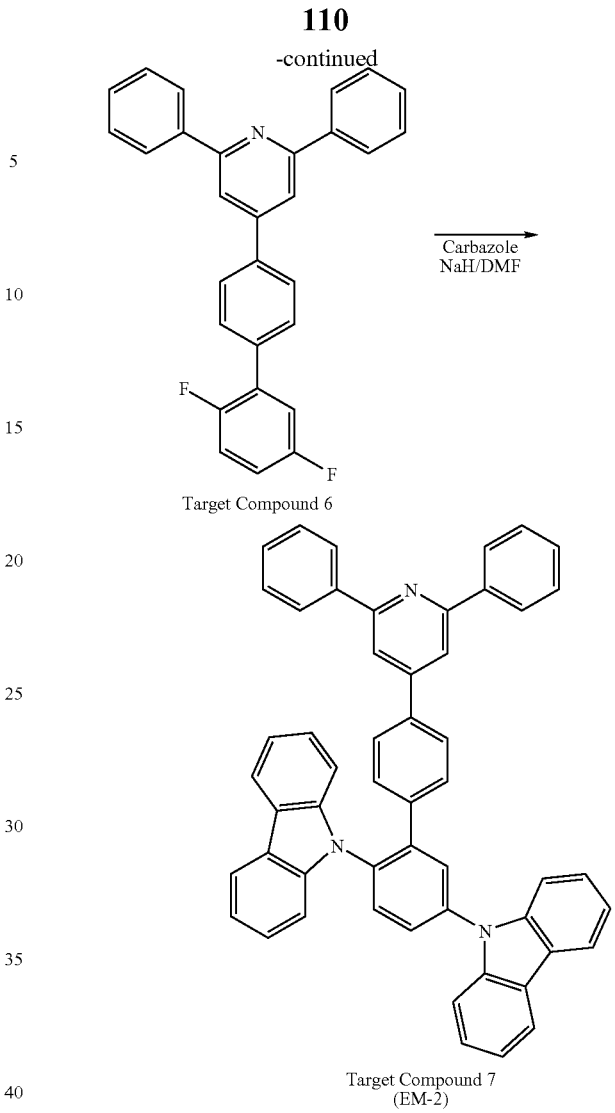

Target Compound 7
(EM-2)

Concentrated sulfuric acid (11.4 ml) was added to a mixture as a solution of 4-bromobenzaldehyde (12.90 g), acetophenone (8.37 g), and acetic acid (100 ml), followed by stirring at 40° C. in a dry air atmosphere for five hours. The mixture was combined with methanol (100 ml) to yield a precipitate, and the precipitate was collected by filtration and washed with methanol. This was washed in a suspended state in methanol and thereby yielded Target Compound 4 (8.72 g).

Target Compound 4 (8.62 g), 1-phenacylpyridinium bromide (12.52 g), ammonium acetate (57.8 g), acetic acid (257 ml), and N,N-dimethylformamide (257 ml) were stirred with heating under reflux in a dry air atmosphere for 5.5 hours, followed by pouring into water (600 ml) with ice cooling to yield a precipitate. The precipitate was collected by filtration and washed with a mixed solvent of ethanol/water. This was purified by washing in a suspended state in ethanol with heating under reflux and thereby yielded Target Compound 5 (8.22 g).

To a mixture of Target Compound 5 (3.09 g), 2,3-difluorophenylboronic acid (1.64 g), dimethoxyethane (80 ml), and water (12 ml) were sequentially added tetrakis(triphenylphosphine)palladium (0.37 g) and potassium carbonate (3.32 g) in a nitrogen stream, followed by stirring with heating under reflux for 5.7 hours. The resulting solution was combined with brine (aqueous sodium chloride solution) (80 ml), extracted with dichloromethane (100 ml), and the organic layer was dried over magnesium sulfate, filtrated, and the filtrate was concentrated to yield a solid. The solid was purified by silica gel column chromatography and thereby yielded Target Compound 6 (3.20 g).

Carbazole (2.51 g) was added to a suspension of sodium hydride (55%, 0.66 g) in anhydrous N,N-dimethylformamide (50 ml) in a nitrogen stream, followed by stirring at 70° C. for one hundred and five minutes. The mixture was combined with Target Compound 6 (2.10 g), followed by stirring with heating under reflux for 4.3 hours. This was combined with water (50 ml) and methanol (50 ml) to yield a precipitate, and the precipitate was collected by filtration and washed with ethanol to yield a solid. The solid was extracted with chloroform, subjected to washing in a suspended state in a mixed solvent of toluene-ethanol-chloroform with heating under reflux, further purified by recrystallization from chloroform-ethanol, and thereby yielded Target Compound 7 (EM-2) (1.57 g).

This was identified as Target Compound 7 through DEI-MS (m/z=713 (M$^+$)).

This compound had a glass transition temperature of 149° C. and a vaporization temperature of 501° C. and did not have a detectable melting point.

Synthesis Example 3

Syntheses of Target Compounds 8 to 9

[Chemical Formula 70]

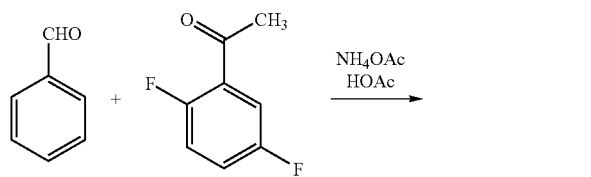

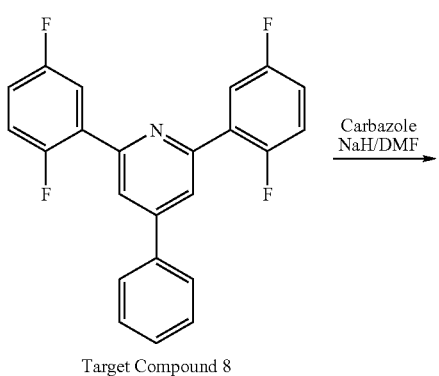

Target Compound 8

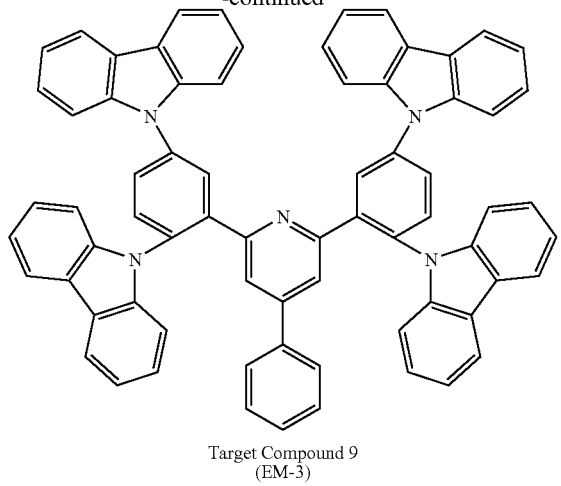

Target Compound 9
(EM-3)

Benzaldehyde (2.12 g), 2',5'-difluoroacetophenone (6.25 g), ammonium acetate (19.7 g), and acetic acid (50 ml) were stirred at 100° C. in the atmosphere for five hours, followed by cooling with ice. The mixture was combined with methanol and water to yield a precipitate, and the precipitate was separated by filtration, purified by washing in a suspended state in methanol, dried with heating under reduced pressure, and thereby yielded Target Compound 8 (1.15 g).

Carbazole (3.03 g) was added to a suspension of sodium hydride (55%, 0.79 g) in anhydrous N,N-dimethylformamide (54 ml) in a nitrogen stream, followed by stirring at 80° C. for sixty minutes. The mixture was combined with Target Compound 8 (1.15 g) and stirred with heating under reflux for 4.8 hours. This was combined with water (50 ml) and methanol (50 ml) under cooling with ice to yield a precipitate, and the precipitate was separated by filtration and washed with methanol to yield a solid. The solid was extracted with chloroform (300 ml), concentrated, purified by washing in a suspended state in a mixed solvent of ethanol-chloroform with heating under reflux, dried with heating under reduced pressure, and thereby yielded Target Compound 9 (EM-3) (2.29 g).

This was identified as Target Compound 9 through DEI-MS (m/z=967 (M$^+$)).

This compound had a glass transition temperature of 160° C. and a vaporization temperature of 535° C. and did not have a detectable melting point.

Synthesis Example 4

Syntheses of Target Compounds 10 to 13

[Chemical Formula 71]

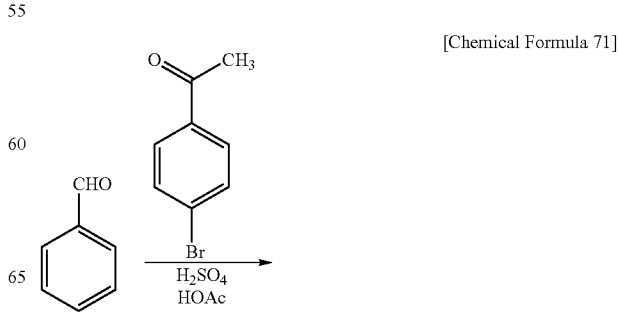

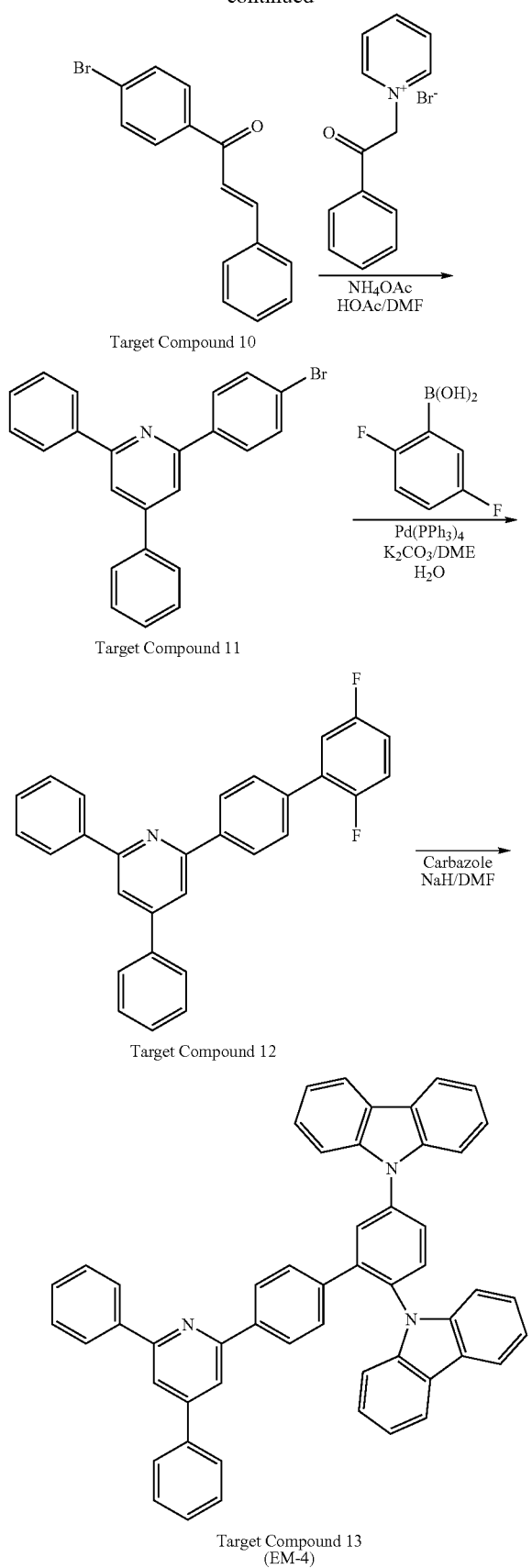

Target Compound 10

Target Compound 11

Target Compound 12

Target Compound 13
(EM-4)

Concentrated sulfuric acid (11.3 ml) was added to a mixture as a solution of benzaldehyde (7.43 g), 4'-bromoacetophenone (13.93 g), and acetic acid (100 ml) in the atmosphere, followed by stirring at 35° C. for 5.3 hours. The resulting mixture was combined with methanol (100 ml) to yield a precipitate, and the precipitate was collected by filtration and washed with methanol. This was washed in a suspended state in ethanol and thereby yielded Target Compound 10 (11.86 g).

Target Compound 10 (11.66 g), 1-phenacylpyridinium bromide (16.94 g), ammonium acetate☐(78.26 g), acetic acid (350 ml), and N,N-dimethylformamide (350 ml) were stirred with heating under reflux in the atmosphere for 6.5 hours, followed by pouring into water (700 ml) under cooling with ice to yield a precipitate. The precipitate was collected by filtration and washed with ethanol. This was purified by recrystallization from a mixed solvent of ethanol-chloroform and thereby yielded Target Compound 11 (11.14 g).

To a mixture of Target Compound 11 (5.79 g), 2,5-difluorophenylboronic acid (3.08 g), dimethoxyethane (150 ml), and water (23 ml) were sequentially added tetrakis(triphenylphosphine)palladium (0.69 g) and potassium carbonate (6.22 g) in a nitrogen stream, followed by stirring with heating under reflux for 3.5 hours. The resulting solution was combined with brine, extracted with dichloromethane, and the organic layer was combined with anhydrous magnesium sulfate and activated clay, stirred, filtrated, and concentrated to yield a solid. The solid was purified by silica gel column chromatography and thereby yielded Target Compound 12 (6.01 g).

A suspension of sodium hydride (55%, 1.31 g) in anhydrous N,N-dimethylformamide (100 ml) was combined with carbazole (5.02 g) in a nitrogen stream, followed by stirring at 80° C. for thirty-five minutes. The mixture was combined with Target Compound 12 (4.19 g) and stirred with heating under reflux for 3.3 hours. This was combined with water (50 ml) and methanol (70 ml) to yield a precipitate, and the precipitate was separated by filtration and washed with methanol to yield a solid. The solid was combined with chloroform to dissolve soluble components, followed by addition of activated clay. The mixture was stirred, filtrated, and concentrated to yield a solid. The solid was purified by recrystallization from a mixed solvent of ethanol-chloroform and recrystallization from a mixed solvent of acetone-ethanol-water-methanol, and thereby yielded Target Compound 13 (EM-4) (2.91 g).

This was identified as Target Compound 13 through DEI-MS (m/z=713 (M$^+$)).

This compound had a glass transition temperature of 148° C., a crystallization temperature of 223° C., a vaporization temperature of 507° C., and a melting point of 300° C.

Synthesis Example 5

Syntheses of Target Compounds 14 to 17

[Chemical Formula 72]

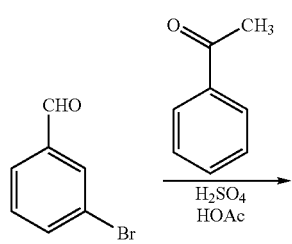

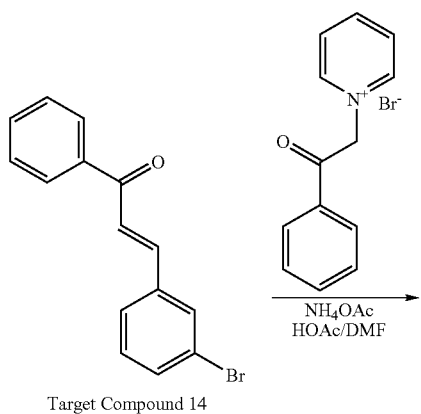

Target Compound 14

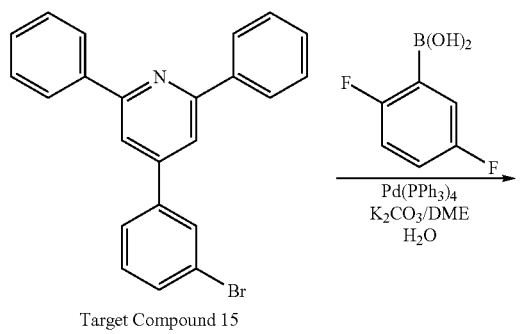

Target Compound 15

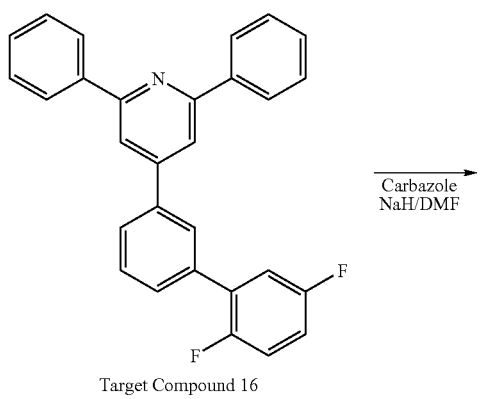

Target Compound 16

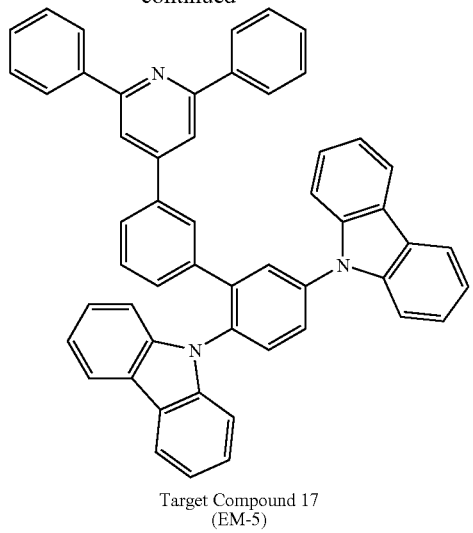

Target Compound 17
(EM-5)

A mixture as a solution of 3-bromobenzaldehyde (15.5 g), acetophenone (10.1 g), and acetic acid (120 ml) was combined with concentrated sulfuric acid (13.5 ml) in a dry air atmosphere, followed by stirring at 40° C. for five hours. The mixture was combined with water (240 ml) to yield a precipitate, and the precipitate was collected by filtration and washed with methanol. This was washed in a suspended state in methanol and thereby yielded Target Compound 14 (14.4 g).

Target Compound 14 (14.4 g), 1-phenacylpyridinium bromide (21.6 g), ammonium acetate (96.6 g), acetic acid (400 ml), and N,N-dimethylformamide (400 ml) were stirred with heating under reflux in the atmosphere for 5.5 hours, and the mixture was poured into ice-water (800 ml) to yield a precipitate. The precipitate was collected by filtration and washed with ethanol. This was purified by recrystallization from toluene-ethanol and thereby yielded Target Compound 15 (8.92 g).

To a mixture of Target Compound 15 (5.80 g), 2,5-difluorophenylboronic acid (3.40 g), dimethoxyethane (150 ml), and water (22.5 ml) were sequentially added tetrakis(triphenylphosphine)palladium (0.69 g) and potassium carbonate (6.22 g) in a nitrogen stream, followed by stirring with heating under reflux for 5.3 hours. The resulting solution was combined with brine (100 ml) under cooling with ice, extracted with dichloromethane (150 ml), and the organic layer was combined with magnesium sulfate and activated clay, followed by stirring. The mixture was filtrated through a silica gel column, concentrated, and thereby yielded Target Compound 16 (6.37 g).

In a nitrogen stream, a suspension of sodium hydride (55%, 2.62 g) in anhydrous N,N-dimethylformamide (100 ml) was combined with carbazole (10.0 g) and stirred at 90° C. for thirty minutes. The resulting solution was combined with a solution of Target Compound 16 (6.37 g) in anhydrous N,N-dimethylformamide (100 ml), followed by stirring with heating under reflux for five hours. This was combined with water (100 ml) and ethanol (30 ml) under cooling with ice to yield a precipitate, and the precipitate was separated by filtration and washed with ethanol to yield a solid. The solid was extracted with chloroform. The extract was combined with activated clay and stirred, the mixture was filtrated through a silica gel column, and the filtrate was concentrated to yield a solid. The solid was purified by recrystallization from N,N-dimethylformamide and ethanol, purified by gel permeation chromatography (GPC), further purified by sublimation with heating a highest temperature of 360° C. at a degree of vacuum of 1×10⁻³ Pa, and thereby yielded Target Compound 17 (EM-5) (1.23 g).

This was identified as Target Compound 17 through DEI-MS (m/z=713 (M⁺)).

This compound had a glass transition temperature of 131° C., a melting point of 241° C., and a vaporization temperature of 498° C.

Synthesis Example 6

Syntheses of Target Compounds 18 to 21

[Chemical Formula 73]

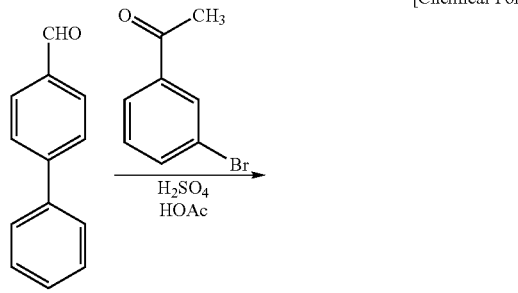

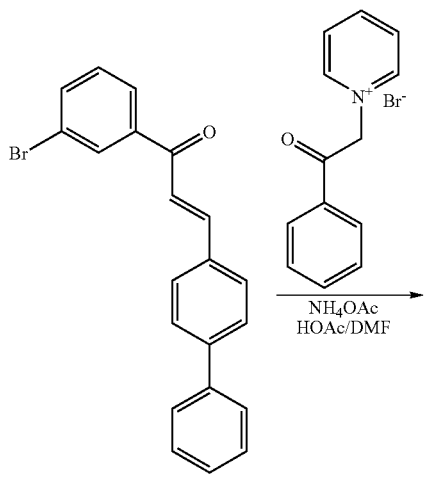

Target Compound18

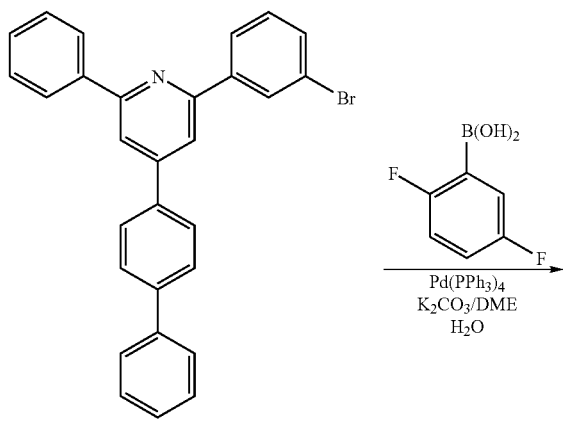

Target Compound19

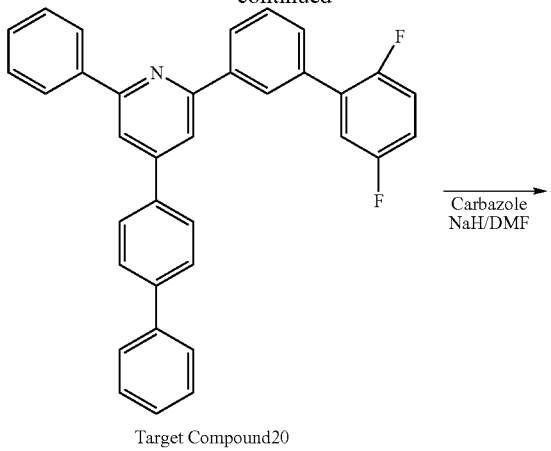

Target Compound20

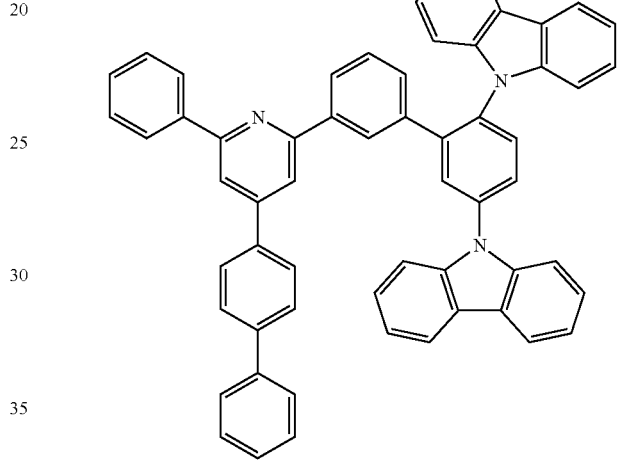

Target Compound21
(EM-7)

A mixture as a solution of 4-phenylbenzaldehyde (10.93 g), 3'-bromoacetophenone (12.54 g), and acetic acid (205 ml) was combined with concentrated sulfuric acid (9.65 ml), followed by stirring at 40° C. in the atmosphere for 5.8 hours. The mixture was combined with methanol (70 ml) and water (120 ml) to yield a precipitate, and the precipitate was collected by filtration, and washed with methanol and ethanol. This was purified by recrystallization from a mixed solvent of ethanol-toluene and thereby yielded Target Compound 18 (16.6 g).

Target Compound 18 (16.6 g), 1-phenacylpyridinium bromide (19.1 g), ammonium acetate (88 g), acetic acid (392 ml), and N,N-dimethylformamide (392 ml) were stirred with heating under reflux in the atmosphere for 5.7 hours, the mixture was poured into ice-water (500 ml) to yield a precipitate. The precipitate was collected by filtration and washed with methanol. This was purified by recrystallization from a mixed solvent of ethanol-toluene and thereby yielded Target Compound 19 (11.2 g).

To a mixture of Target Compound 19 (4.62 g), 2,5-difluorophenylboronic acid (2.21 g), dimethoxyethane (100 ml), and water (15 ml) were sequentially added tetrakis(triphenylphosphine)palladium (0.46 g) and potassium carbonate (4.15 g) in a nitrogen stream, followed by stirring with heating under reflux for 4.3 hours. The resulting solution was combined with ethanol (100 ml) and water (70 ml), from which the supernatant was removed to yield a solid. The solid was purified by recrystallization from a mixed solvent of ethanol-chloroform and thereby yielded Target Compound 20 (3.42 g).

A suspension of sodium hydride (55%, 1.2 g) in anhydrous N,N-dimethylformamide (100 ml) was combined with carbazole (4.59 g) in a nitrogen stream, stirred at 80° C. for sixty minutes, further combined with Target Compound 20 (3.4 g), and stirred with heating under reflux for 3.5 hours. After standing to cool, the mixture was combined with sodium hydride (55%, 0.9 g) and further stirred with heating under reflux for 3.5 hours. After standing to cool, this was combined with water (100 ml) and methanol (100 ml) on an ice bath to yield a precipitate, and the precipitate was separated by filtration and washed with methanol to yield a solid. The solid was combined with dichloromethane (120 ml) to dissolve soluble components, and this was combined with anhydrous magnesium sulfate and activated clay, stirred, filtrated, and concentrated to yield a solid. The solid was purified by silica gel column chromatography, further purified by sublimation with heating at a highest temperature of 410° C. at a degree of vacuum of $1\times10^{-3}$ Pa, and thereby yielded Target Compound 21 (EM-7) (0.89 g).

This was identified as Target Compound 21 through DEI-MS (m/z=789 (M$^+$)).

This compound had a glass transition temperature of 146° C. and a vaporization temperature of 522° C. and did not have detectable crystallization temperature and melting point.

Synthesis Example 7

Syntheses of Target Compounds 22 to 24

[Chemical Formula 74]

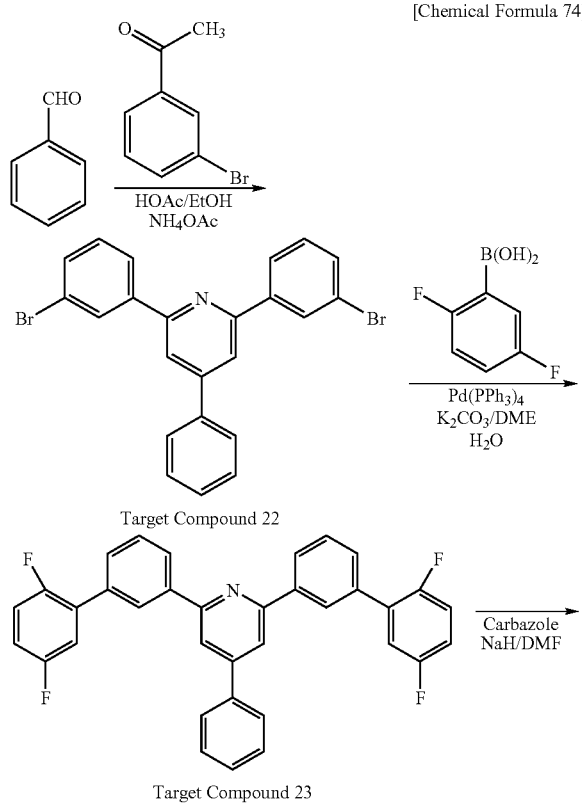

Target Compound 22

Target Compound 23

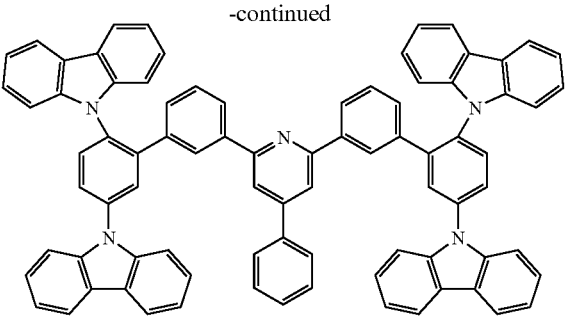

Target Compound 24
(EM-6)

In the atmosphere, 3'-bromoacetophenone (39.8 g), benzaldehyde (10.6 g), ammonium acetate☐(98.7 g), acetic acid (170 ml), and ethanol (170 ml) were stirred with heating under reflux for 4.5 hours, followed by standing to cool to room temperature to yield crystals. The crystals were collected by filtration, washed with ethanol, purified by recrystallization from a mixed solvent of toluene-ethanol, and thereby yielded Target Compound 22 (4.48 g).

To a mixture of Target Compound 22 (2.33 g), 2,5-difluorophenylboronic acid (2.21 g), dimethoxyethane (100 ml), and water (15 ml) were sequentially added tetrakis(triphenylphosphine)palladium (0.46 g) and potassium carbonate (4.15 g) in a nitrogen stream, followed by stirring with heating under reflux for 8.5 hours. The resulting solution was combined with brine (100 ml), extracted with methylene chloride (100 ml), and the organic layer was combined with anhydrous magnesium sulfate and activated clay and filtrated. The filtrate was concentrated to yield a solid, and the solid was purified by recrystallization from toluene-ethanol and thereby yielded Target Compound 23 (2.54 g).

A suspension of sodium hydride (55%, 1.25 g) in anhydrous N,N-dimethylformamide (100 ml) was combined with carbazole (4.78 g) and stirred at 80° C. in a nitrogen stream for forty minutes, further combined with Target Compound 23 (2.53 g), followed by stirring with heating under reflux for seven hours. After standing to cool, the mixture was combined with sodium hydride (55%, 0.96 g) and further stirred with heating under reflux for 5.5 hours. This was combined with ice-water (80 ml) and methanol (80 ml) on an ice bath to yield a precipitate, and the precipitate was separated by filtration and washed with methanol to yield a solid. The solid was combined with dichloromethane (120 ml) to dissolve soluble components, and this was combined with anhydrous magnesium sulfate and activated clay, stirred, filtrated, and the filtrate was concentrated to yield a solid. The solid was purified by sequentially subjecting to recrystallization from a mixed solvent of chloroform-ethanol, silica gel column chromatography, reprecipitation from methylene chloride-methanol, and sublimation purification, and thereby yielded Target Compound 24 (EM-6) (0.65 g).

This was identified as Target Compound 24 through DEI-MS (m/z=1119 (M$^+$)).

This compound did not have a detectable crystallization temperature and a detectable melting point and had a glass transition temperature of 184° C. and a vaporization temperature of 565° C.

[Preparation Examples of Organic Electroluminescent Devices]

Preparation examples of organic electroluminescent devices according to the present invention will be illustrated below.

Part of the prepared organic electroluminescent devices were subjected to the following driving lifetime tests.

<Driving Lifetime Test>

Temperature: room temperature

Driving method: direct-current driving (DC driving)

Initial luminance: 2,500 cd/m$^2$

In the tests, each device was allowed to continuously emit light by supplying a constant current, and a time required for luminance to decrease by 20% (L/L$_0$=0.8) was determined to compare. Relative times of the devices were determined taking the time for Referential Device 2 of Referential Example 2 as 1.00.

Referential Example 1

Preparation of Referential Device 1

An organic electroluminescent device having the structure shown in FIG. 3 was prepared in the following manner.

An Indium-tin oxide (ITO) transparent electroconductive film deposited to a thickness of 150 nm on a glass substrate 1 (sputtered film; sheet resistance: 15Ω) was patterned in a 2-mm width stripe pattern using a common photolithography technique and etching with hydrochloric acid, thereby forming an anode 2. The thus patterned ITO substrate was washed by applying ultrasonic waves in acetone, washed with pure water, then washed by applying ultrasonic waves in isopropyl alcohol, followed by drying using a nitrogen blow and washing by applying UV rays and ozone.

As a material for a hole injection layer 3, a non-conjugated polymeric compound (PB-1, having a weight-average molecular weight of 29400 and a number-average molecular weight of 12600) having an aromatic amino group of the following structural formula was applied by spin coating together with an electron acceptor (A-2) having the following structural formula under the following conditions.

[Chemical Formula 75]

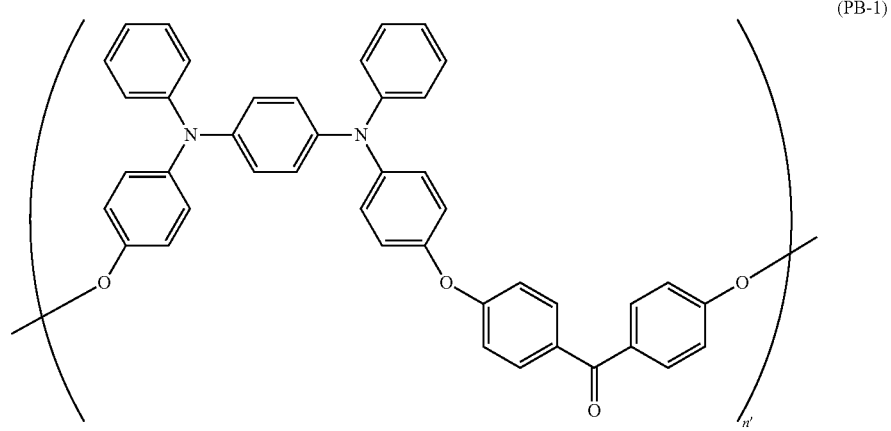

(PB-1)

[Chemical Formula 76]

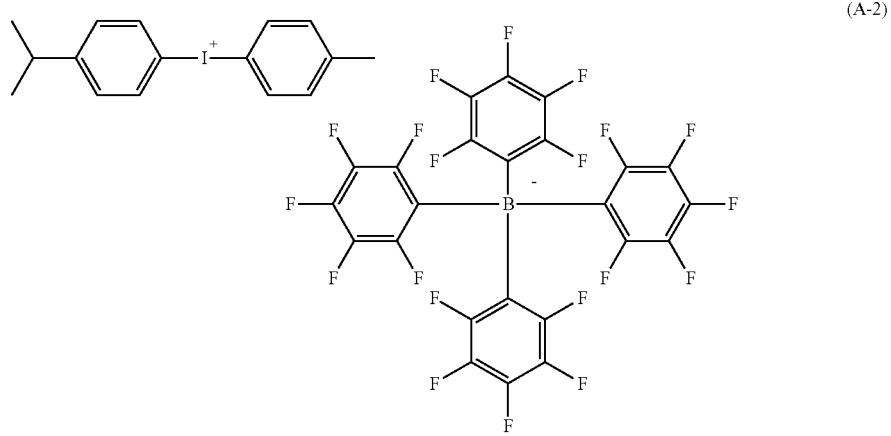

(A-2)

Condition of Spin Coating

Solvent: ethyl benzoate;

Concentration of coating composition: 2 percent by weight;

Ratio of PB-1 to A-2: 10:2 (by weight);

Revolution number of spinner: 1500 [rpm];

Rotation time of spinner: 30 [sec.]; and

Drying condition; 230 [° C.] for 15 [min.]

A uniform thin film 30 nm thick was formed by the spin coating.

Next, the substrate bearing the formed hole injection layer 3 was placed in a vacuum deposition chamber. After roughly evacuating the chamber using an oil rotary pump, the inside of the chamber was evacuated to a vacuum degree of 6.2×10$^{-5}$ Pa (about 4.7×10$^{-7}$ Torr) or less by using a cryogenic pump. An arylamine compound (H-1) shown below was placed in a ceramic crucible placed within the chamber and was heated through a tantalum wire heater disposed around the crucible to conduct vacuum deposition. The temperature of the crucible in this procedure was controlled within the range of from 313° C. to 334° C. The vacuum deposition was conducted at a vacuum degree of $7.0 \times 10^{-5}$ Pa (about $5.3 \times 10^{-7}$ Torr) and a vacuum deposition rate of 0.21 nm per second and thereby yielded a hole transport layer 4 having a thickness of 40 nm.

[Chemical Formula 77]

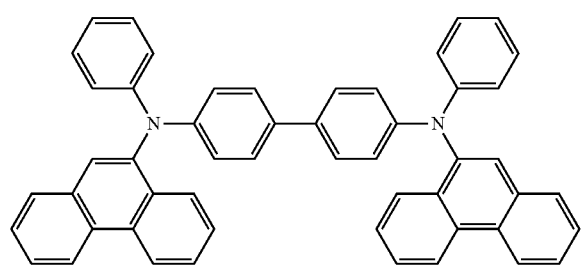

(H-1)

Subsequently, a carbazole derivative (CBP) shown below as a major component (host material) and an organic iridium complex (D-1) shown below as a minor component (dopant) of a light-emitting layer 5 were placed in different ceramic crucibles, and film formation was carried out by binary vacuum deposition.

[Chemical Formula 78]

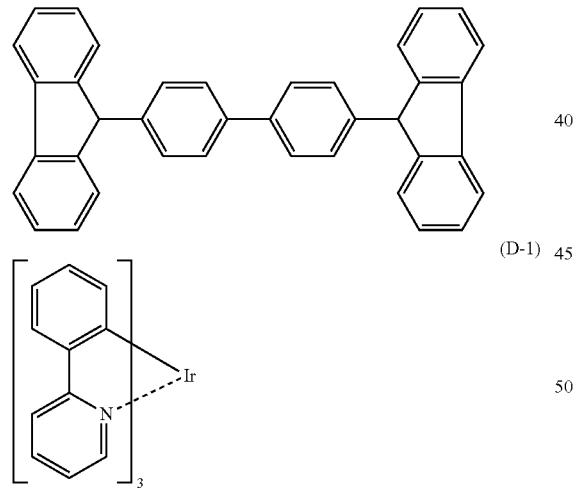

(CBP)

(D-1)

The crucible temperature and the vacuum deposition rate for the compound (CBP) were controlled to be 295° C. to 299° C. and 0.11 nm per second, respectively, while the crucible temperature for the compound (D-1) was controlled to be 252° C. to 255° C. Thus, a light-emitting layer 5 having a thickness of 30 nm and containing about 6 percent by weight of the compound (D-1) was stacked on the hole transport layer 4. The degree of vacuum upon vacuum deposition was $6.7 \times 10^{-5}$ Pa (about $5.0 \times 10^{-7}$ Torr).

Further, the following pyridine derivative (HB-1) was stacked as a hole blocking layer 6 in a thickness of 5 nm at a crucible temperature of 211° C. to 215° C. and a vacuum deposition rate of 0.09 nm per second. The degree of vacuum upon vacuum deposition was $6.2 \times 10^{-5}$ Pa (about $4.7 \times 10^{-7}$ Torr).

[Chemical Formula 79]

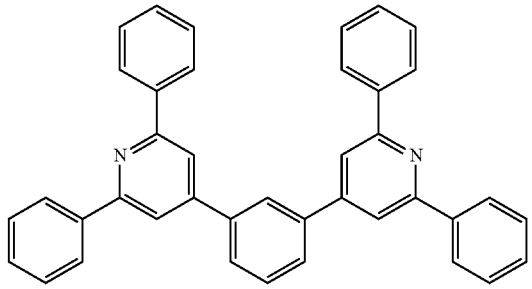

(HB-1)

On the hole blocking layer 6 was deposited, as an electron transport layer 7, the following aluminum 8-hydroxyquinoline complex (ET-1) in the same manner. The temperature of the crucible for the aluminum 8-hydroxyquinoline complex in this procedure was controlled within the range of from 234° C. to 245° C. The vacuum deposition was carried out at a degree of vacuum of $6.0 \times 10^{-5}$ Pa (about $4.5 \times 10^{-7}$ Torr) and a vacuum deposition rate of 0.22 nm per second to yield a film 30 nm thick.

[Chemical Formula 80]

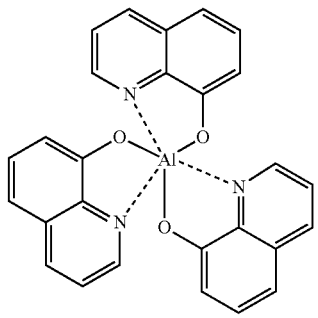

(ET-1)

The temperature of the substrate upon vacuum deposition of the hole injection layer 3, the hole transport layer 4, the light-emitting layer 5, the hole blocking layer 6, and the electron transport layer 7 was kept to room temperature.

The device which had been subjected to vacuum deposition up to the electron transport layer 7 was once taken out of the vacuum deposition chamber into the atmosphere. A 2-mm width striped shadow mask as a mask for vacuum deposition of a cathode was brought in close contact with the device perpendicularly to the ITO stripe of the anode 2, and the device was placed in a different vacuum deposition chamber. The chamber was evacuated to a degree of vacuum of $2.0 \times 10^{-6}$ Torr (about $2.7 \times 10^{-4}$ Pa) or less in the same manner as with the organic layers. As a cathode 8, initially, a film of lithium fluoride (LiF) was deposited to a thickness of 0.5 nm on the electron transport layer 7 at a vacuum deposition rate of 0.03 nm per second and a degree of vacuum of $2.8 \times 10^{-6}$ Torr (about $3.7 \times 10^{-4}$ Pa) using a molybdenum boat. Next, aluminum was heated in the same manner using a molybdenum boat and was deposited at a vacuum deposition rate of 0.46 nm per second and a degree of vacuum of $9.6 \times 10^{-6}$ Torr (about $1.3 \times 10^{-3}$ Pa) to yield an aluminum layer 80 nm thick. Thus, the cathode 3 was completed. The temperature of the substrate upon vacuum deposition of the two-layered cathode 8 was kept to room temperature.

Thus, an organic electroluminescent device having a light-emitting area of 2 mm wide and 2 mm long was obtained. The light emitting properties of the device are as follows, Current efficiency: 24.7 [cd/A] at 2.5 mA/cm$^2$;

Voltage: 6.0 [V] at 2.5 mA/cm$^2$;

Luminous efficiency: 20.7 [1 m/w] at 100 cd/m$^2$, and

Luminance holding ratio: 0.97 at 250 mA/cm$^2$

The luminance holding ratio herein is a value obtained by dividing L by $L_0$, wherein L is the luminance fifty seconds into driving at 250 mA/cm2; and $L_0$ is the luminance at the beginning of driving. The luminance holding ratio is an index of driving stability.

The maximal wavelength in emission spectrum of the device was 512 nm, which was identified to be from the organic iridium complex (D-1). The chromaticity in terms of CIE (x, y) was (0.30, 0.59).

Referential Example 2

Preparation of Referential Device 2

A device having the structure shown in FIG. 4 was prepared by the procedure as with Referential Device 1, except for not forming a hole blocking layer containing the pyridine derivative (HB-1). The light emitting properties of the device are shown in Table 1. The light emitting properties in Table 1 are relative values taxing the values of Referential Device 1 as 1.00, respectively.

The maximal wavelength in emission spectrum of the device was 512 nm with chromaticity in terms of CIE (x, y) of (0.29, 0.60), which was identified to be from the organic iridium complex (D-1). Referential Device 2 gave light emission from the organic iridium complex even though it did not have a hole blocking layer, but this device showed a lower luminous efficiency and a higher drive voltage than those of Referential Device 1.

Example 1

A device was prepared by the procedure as with Referential Device 1 in Referential Example 1, except for using following Target Compound 3 (EM-1) synthetically prepared according to Synthesis Example 1 as a major component (host material) of the light-emitting layer 5 instead of the carbazole derivative (CBP).

The light emitting properties and lifetime properties of the device are shown in Table 1.

The maximal wavelength in emission spectrum of the device was 514 nm with chromaticity in terms of CIE (x, y) of (0.30, 0.61), which was identified to be from the organic iridium complex (D-1).

This device had a higher luminous efficiency than that of Referential Device 1 and showed a longer lifetime than that of Referential Device 2.

[Chemical Formula 81]

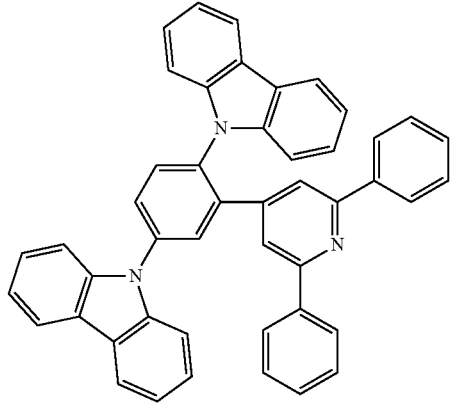

(EM-1)

Example 2

A device was prepared by the procedure as with Referential Device 2 in Referential Example 2, except for using EM-1 as a major component (host material) of the light-emitting layer 5 instead of the carbazole derivative (CBP).

The light emitting properties and lifetime properties of the device are shown in Table 1.

The maximal wavelength in emission spectrum of the device was 514 nm with chromaticity in terms of CIE (x, y) of (0.30, 0.61), which was identified to be from the organic iridium complex (D-1).

This device showed a higher luminous efficiency than that of Referential Device 1.

In comparison between the properties of Referential Devices 1 and 2 and those of the devices according to Examples 1 and 2, the devices according to Examples 1 and 2 using the organic compound according to the present invention do not show significant decrease in luminous efficiency even without providing a hole blocking layer. This indicates that these devices have a high luminous efficiency and a low drive voltage, regardless of the presence or absence of a hole blocking layer and can be said as stable devices.

Example 3

A device was prepared by the procedure as with Referential Device 1 in Referential Example 1, except for using following Target Compound 7 (EM-2) synthetically prepared according to Synthesis Example 2 as a major component (host material) of the light-emitting layer 5 instead of the carbazole derivative (CBP).

The light emitting properties and lifetime properties of the device are shown in Table 1.

The maximal wavelength in emission spectrum of the device was 513 nm with chromaticity in terms of CIE (x, y) of (0.31, 0.61), which was identified to be from the organic iridium complex (D-1).

This device was very excellent in lifetime properties.

[Chemical Formula 82]

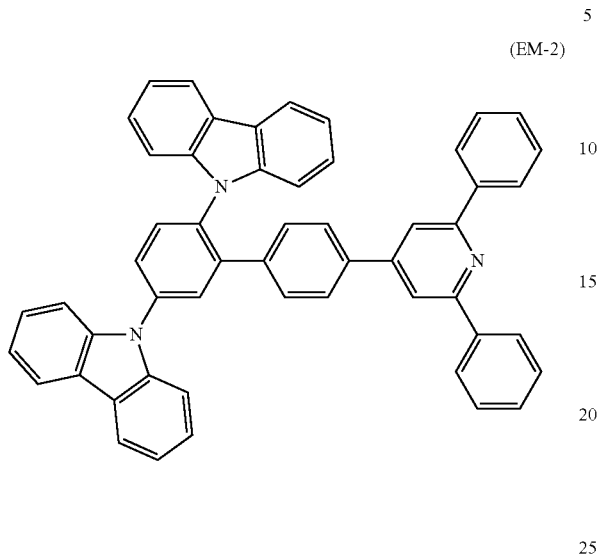

(EM-2)

[Chemical Formula 83]

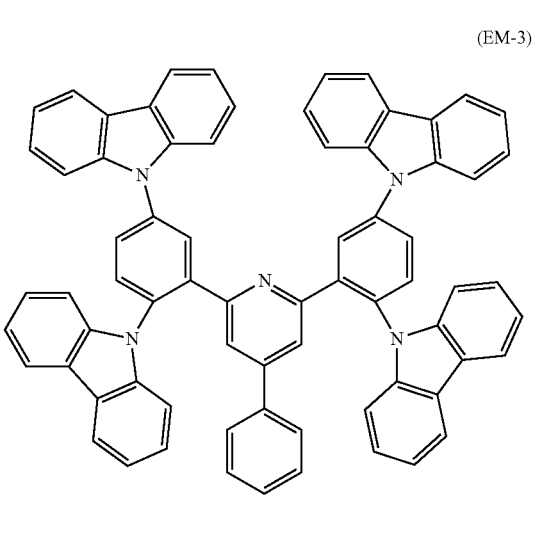

(EM-3)

Example 4

A device was prepared by the procedure as with Referential Device 2 in Referential Example 2, except for using EM-2 as a major component (host material) of the light-emitting layer 5 instead of the carbazole derivative (CBP).

The light emitting properties and lifetime properties of the device are shown in Table 1.

The maximal wavelength in emission spectrum of the device was 513 nm with chromaticity in terms of CIE (x, y) of (0.31, 0.61), which was identified no be from the organic iridium complex (D-1). This device showed a longer lifetime than that of Referential Devices.

Example 5

A device was prepared by the procedure as with Referential Device 1 in Referential Example 1, except for using following Target Compound 9 (EM-3) synthetically prepared according to Synthesis Example 3 as a major component (host material) of the light-emitting layer 5 instead of the carbazole derivative (CBP).

The light emitting properties of the device are shown in Table 1.

The maximal wavelength in emission spectrum of the device was 514 nm with chromaticity in terms of CIE (x, y) of (0.31, 0.61), which was identified to be from the organic iridium complex (D-1).

This device emitted light with a higher efficiency and was driven at a lower voltage than those of Referential Device 1.

Example 6

A device was prepared by the procedure as with Referential Device 2 in Referential Example 2, except for using EM-3 as a major component (host material) of the light-emitting layer 5 instead of the carbazole derivative (CBP).

The light emitting properties of the device are shown in Table 1.

The maximal wavelength in emission spectrum of the device was 514 nm with chromaticity in terms of CIE (x, y) of (0.31, 0.61), which was identified to be from the organic iridium complex (D-1).

This device emitted light with a higher efficiency and was driven at a lower voltage than those of Referential Device 1, even though it had no hole blocking layer.

Example 7

A device was prepared by the procedure as with Referential Device 1 in Referential Example 1, except for using following Target Compound 13 (EM-4) synthetically prepared according to Synthesis Example 4 as a major component (host material) of the light-emitting layer 5 instead of the carbazole derivative (CBP).

The light emitting properties of the device are shown in Table 1.

The maximal wavelength in emission spectrum of the device was 514 nm with chromaticity in terms of CIE (x, y) of (0.30, 0.61), which was identified to be from the organic iridium complex (D-1).

The device emitted light with a higher efficiency and was driven at a lower voltage than those of Referential Device 1.

[Chemical Formula 84]

(EM-4)

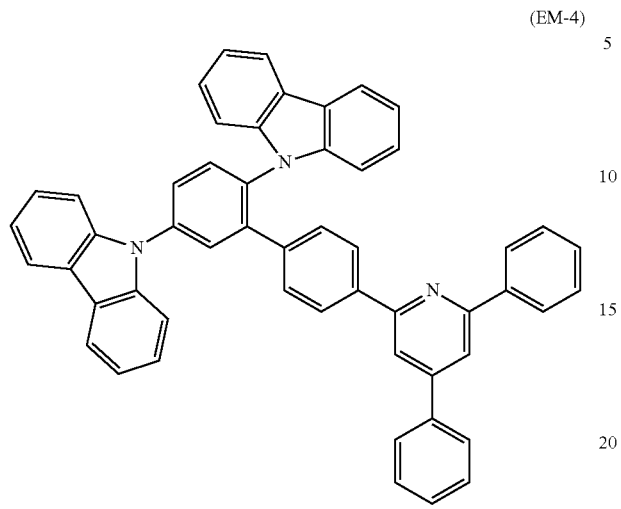

[Chemical Formula 85]

(EM-5)

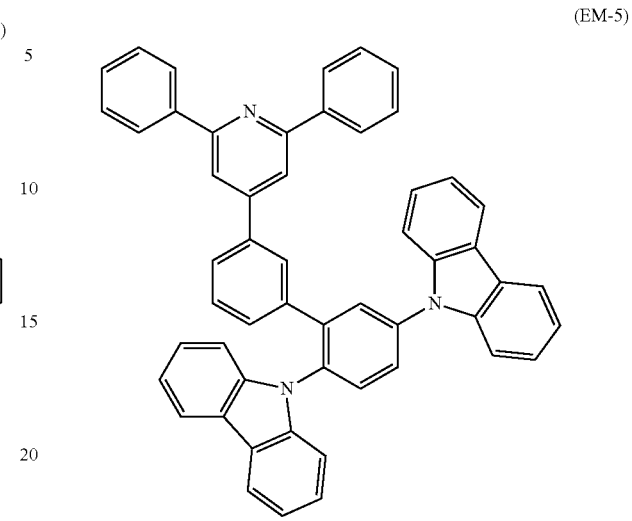

Example 8

A device was prepared by the procedure as with Referential Device 2 in Referential Example 2, except for using EM-4 as a major component (host material) of the light-emitting layer 5 instead of the carbazole derivative (CBP).

The light emitting properties of the device are shown in Table 1.

The maximal wavelength in emission spectrum of the device was 514 nm with chromaticity in terms of CIE (x, y) of (0.30, 0.61), which was identified to be from the organic iridium complex (D-1).

This device emitted light with a higher efficiency and was driven at a lower voltage than those of Referential Device 1, even though it had no hole blocking layer.

Example 9

A device was prepared by the procedure as with Referential Device 1 in Referential Example 1, except for using following Target Compound 17 (EM-5) synthetically prepared according to Synthesis Example 5 as a major component (host material) of the light-emitting layer 5 instead of the carbazole derivative (CBP).

The light emitting properties of the device are shown in Table 1.

The maximal wavelength in emission spectrum of the device was 514 nm with chromaticity in terms of CIE (x, y) of (0.30, 0.62), which was identified to be from the organic iridium complex (D-1).

This device emitted light with a higher efficiency than that of Referential Device 1.

Example 10

A device was prepared by the procedure as with Referential Device 2 in Referential Example 2, except for using EM-5 as a major component (host material) of the light-emitting layer 5 instead of the carbazole derivative (CBP).

The maximal wavelength in emission spectrum of the device was 514 nm with chromaticity in terms of CIE (x, y) of (0.30, 0.62), which was identified to be from the organic iridium complex (D-1).

Example 11

A device was prepared by the procedure as with Referential Device 1 in Referential Example 1, except for using following Target Compound 24 (EM-6) synthetically prepared according to Synthesis Example 7 as a major component (host material) of the light-emitting layer 5 instead of the carbazole derivative (CBP).

The light emitting properties of the device are shown in Table 1.

The maximal wavelength in emission spectrum of the device was 515 nm with chromaticity in terms of CIE (x, y) of (0.30, 0.61), which was identified to be from the organic iridium complex (D-1).

The device emitted light with a higher efficiency and was driven at a lower voltage than those of Referential Device 1.

[Chemical Formula 86]

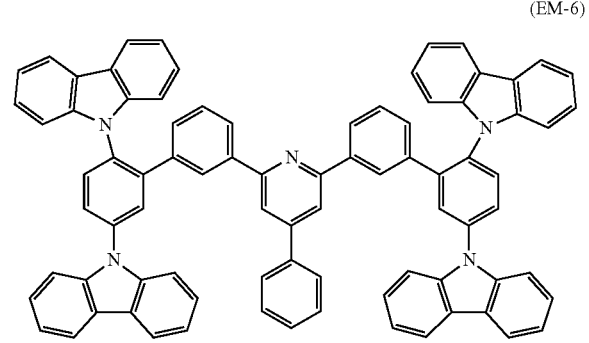

(EM-6)

[Chemical Formula 87]

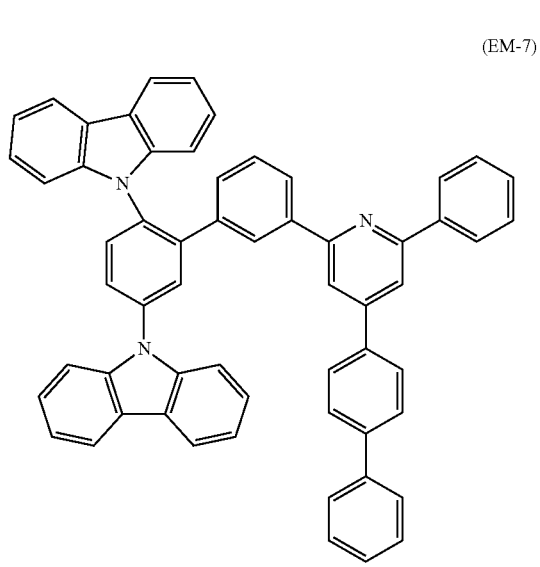

(EM-7)

Example 12

A device was prepared by the procedure as with Referential Device 2 In Referential Example 2, except for using EM-6 as a major component (host material) of the light-emitting layer 5 instead of the carbazole derivative (CBP).

The light emitting properties of the device are shown in Table 1.

The maximal wavelength in emission spectrum of the device was 514 nm with chromaticity in terms of CIE (x, y) of (0.31, 0.61), which was identified to be from the organic iridium complex (D-1).

This device emitted light with a higher efficiency and was driven at a lower voltage than those of Referential Devices, even though it had no hole blocking layer.

Example 13

A device was prepared by the procedure as with Referential Device 1 in Referential Example 1, except for using following Target Compound 21 (EM-7) synthetically prepared according to Synthesis Example 6 as a major component (host material) of the light-emitting layer 5 instead of the carbazole derivative (CBP).

The maximal wavelength in emission spectrum of the device was 515 nm with chromaticity in terms of CIE (x, y) of (0.30, 0.61), which was identified to be from the organic iridium complex (D-1).

Example 14

A device was prepared by the procedure as with Referential Device 2 in Referential Example 2, except for using EM-7 as a major component (host material) of the light-emitting layer 5 instead of the carbazole derivative (CBP).

The maximal wavelength in emission spectrum of the device was 514 nm with chromaticity in terms of CIE (x, y) of (0.31, 0.61), which was identified to be from the organic iridium complex (D-1).

Comparative Example 1

A device was prepared by the procedure as with Referential Device 1 in Referential Example 1, except for using following EM-11 as a major component (host material) of the light-emitting layer 5 instead of the carbazole derivative (CBP).

The light emitting properties and lifetime properties of the device are shown in Table 1.

The maximal wavelength in emission spectrum of the device was 514 nm with chromaticity in terms of CIE (x, y) of (0.31, 0.61), which was identified to be from the organic iridium complex (D-1).

[Chemical Formula 88]

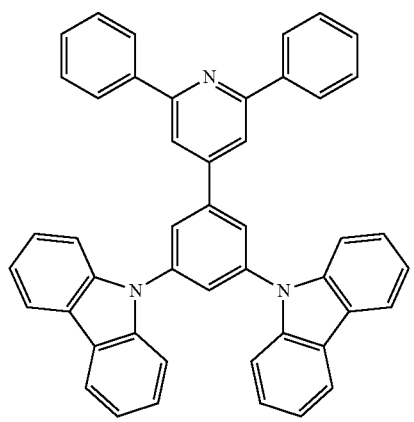

(EM-11)

Comparative Example 2

A device was prepared by the procedure as with Referential Device 2 in Referential Example 2, except for using EM-11 as a major component (host material) of the light-emitting layer 5 instead of the carbazole derivative (CBP).

The light emitting properties and lifetime properties of the device are shown in Table 1.

The maximal wavelength in emission spectrum of the device was 514 nm with chromaticity in terms of CIE (x, y) of (0.31, 0.61), which was identified to be from the organic iridium complex (D-1).

These results demonstrate that the devices according no Comparative Examples 1 and 2 using EM-11 show a lower luminous efficiency and a significantly shorter lifetime than those of Referential Device 1 and the devices according typically to Examples 1 and 2, regardless of the presence or absence of a hole blocking layer.

changes and modifications may be made without departing from the spirit and scope of the present invention.

The present invention is based on Japanese Patent Application No. 2004-373981 filed on Dec. 24, 2004, the entire contents of which being incorporated herein by reference.

The invention claimed is:

1. An organic compound represented by following Formula (I):

(I)

wherein $Cz^1$ and $Cz^2$ each represent a carbazolyl group;

Z represents a direct bond or an arbitrary linkage group enabling the conjugation of nitrogen atoms in the carbazole rings of $Cz^1$ and $Cz^2$ with each other;

each of $Cz^1$, $Cz^2$, and Z may be substituted;

Q represents a direct bond connecting to "G" in following Formula (II):

(II)

wherein Ring $B^1$ represents a six-membered aromatic heterocyclic ring having "n" nitrogen atom(s) as hetero atom(s);

"n" represents an integer of from 1 to 3;

Gs connect to carbon atoms at an ortho position and a para position with respect to the nitrogen atom(s) in Ring $B^1$;

G represents a direct bond or an arbitrary linkage group connecting to Q when G connects to Q;

TABLE 1

| | Component of device | | Properties of device | | | | |
| --- | --- | --- | --- | --- | --- | --- | --- |
| | Host material of light-emitting layer | Hole blocking material | Current efficiency (@2.5 mA/cm$^2$) | Voltage (@2.5 mA/cm$^2$) | Luminous efficiency (@100 cd/m$^2$) | Luminance holding ratio (@250 mA/cm$^2$) | Driving lifetime (@2,500 cd/m$^2$) |
| Referential Device 1 | CBP | HB-1 | 1.00 | 1.00 | 1.00 | 1.00 | |
| Referential Device 2 | CBP | — | 0.60 | 1.15 | 0.52 | 1.03 | 1.00 |
| Example 1 | EM-1 | HB-1 | 1.20 | 0.97 | 1.24 | 0.99 | 1.14 |
| Example 2 | EM-1 | — | 1.03 | 0.91 | 1.13 | 0.99 | 0.93 |
| Example 3 | EM-2 | HB-1 | 0.99 | 1.12 | 0.88 | 0.98 | 1.50 |
| Example 4 | EM-2 | — | 0.93 | 1.01 | 0.92 | 0.98 | 1.13 |
| Example 5 | EM-3 | HB-1 | 1.09 | 0.75 | 1.45 | 0.95 | |
| Example 6 | EM-3 | — | 1.13 | 0.7 | 1.61 | 0.95 | |
| Example 7 | EM-4 | HB-1 | 1.10 | 0.96 | 1.10 | 0.95 | |
| Example 8 | EM-4 | — | 1.07 | 0.91 | 1.05 | 0.96 | |
| Example 9 | EM-5 | HB-1 | 1.23 | 1.02 | 1.22 | 1.00 | |
| Example 10 | EM-5 | — | 1.15 | 0.89 | 1.34 | 0.96 | |
| Example 11 | EM-6 | HB-1 | | | | | |
| Example 12 | EM-6 | — | 1.13 | 0.90 | 1.01 | 0.98 | |
| Com. Ex. 1 | EM-11 | HB-1 | 0.84 | 1.13 | 0.74 | 0.96 | 0.66 |
| Com. Ex. 2 | EM-11 | — | 0.85 | 1.04 | 0.81 | 0.97 | 0.66 |

While the present invention has been shown and described in detail with reference to specific embodiments thereof, it will be understood by those skilled in the art that various G represents an aromatic hydrocarbon group when G does not connect to Q;

"m" represents an integer of from 3 to 5;

plural Gs in one molecule may be the same as or different from one another; and

Ring $B^1$ may have one or more substituents in addition to Gs, wherein said arbitrary linkage group, if present, represents -(Ph)$_p$-, wherein Ph represents a phenylene group which may be substituted; and "p" represents an integer of from 1 to 8.

2. An organic compound represented by following Formula (I):

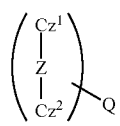
(I)

wherein $Cz^1$ and $Cz^2$ each represent a carbazolyl group;

Z represents an aromatic hydrocarbon group enabling the conjugation of nitrogen atoms in the carbazole rings of $Cz^1$ and $Cz^2$ with each other;

each of $Cz^1$, $Cz^2$, and Z may be substituted;

Q represents a direct bond connecting to "G" in following Formula (II):

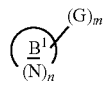
(II)

wherein Ring $B^1$ represents a six-membered aromatic heterocyclic ring having "n" nitrogen atom(s) as hetero atom(s);

"n" represents an integer of from 1 to 3;

Gs connect to carbon atoms at an ortho position and a para position with respect to the nitrogen atom(s) in Ring $B^1$;

G represents a direct bond or an arbitrary linkage group connecting to Q when G connects to Q;

G represents an aromatic hydrocarbon group when G does not connect to Q;

"m" represents an integer of from 3 to 5;

plural Gs in one molecule may be the same as or different from one another; and

Ring $B^1$ may have one or more substituents in addition to Gs, wherein a moiety of the partial structure represented by Formula (I), except for the moiety of Formula (II), is one selected from following V-1, V-7, V-9, V-13, V-14, and V-15:

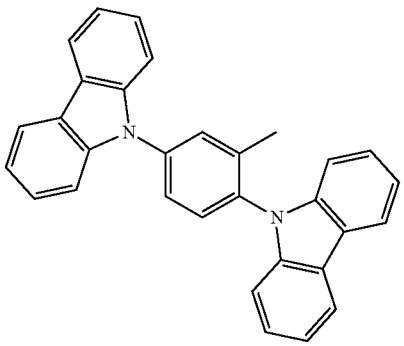
V-1

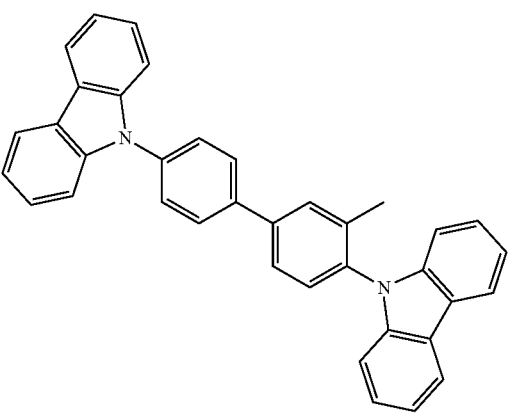
V-7

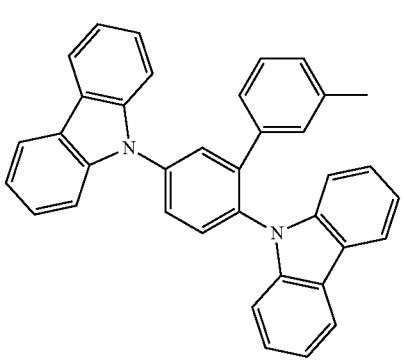
V-9

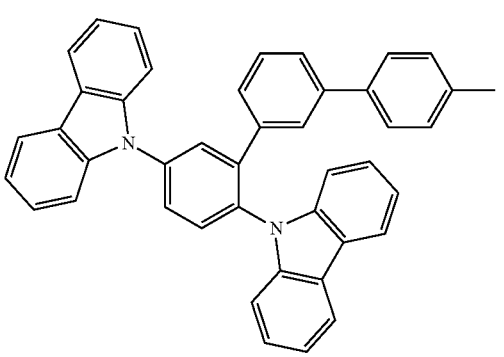
V-13

-continued
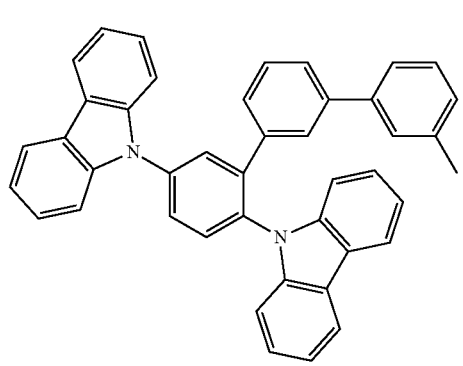
V-14
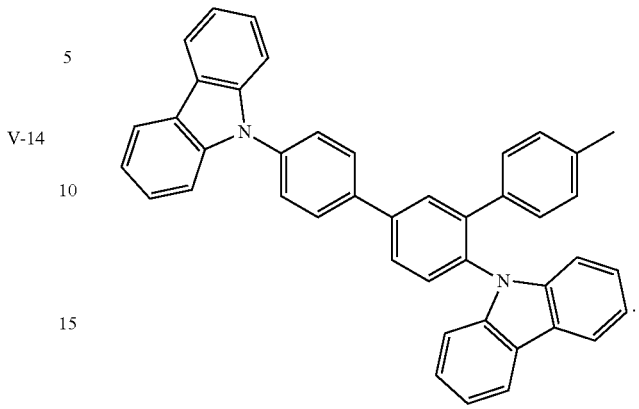
V-15
3. An organic compound represented by any one of following structural formulae, wherein —N-Cz represents an N-carbazolyl group:
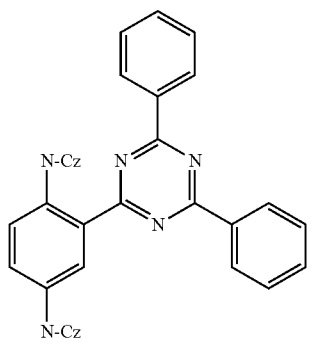
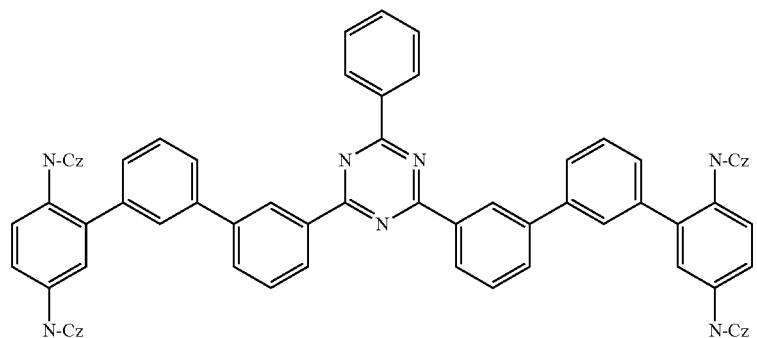
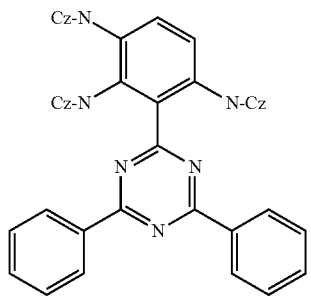
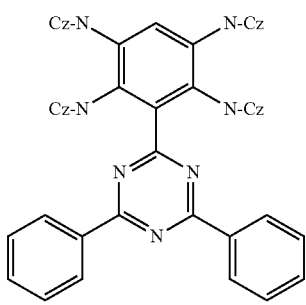
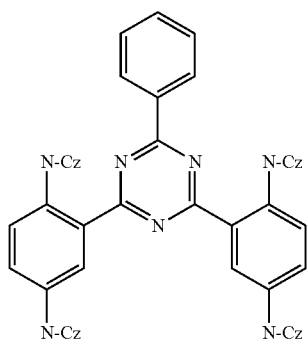
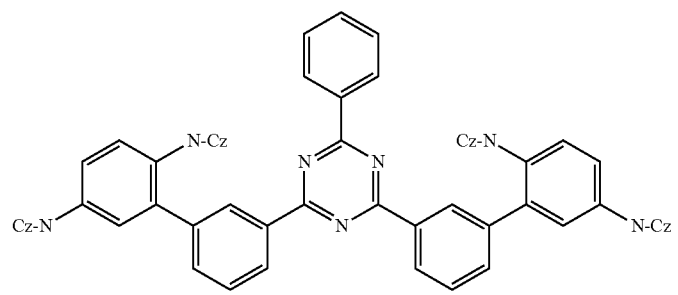

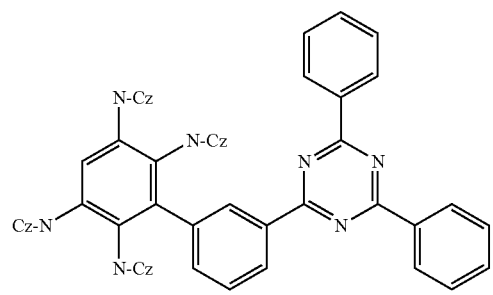
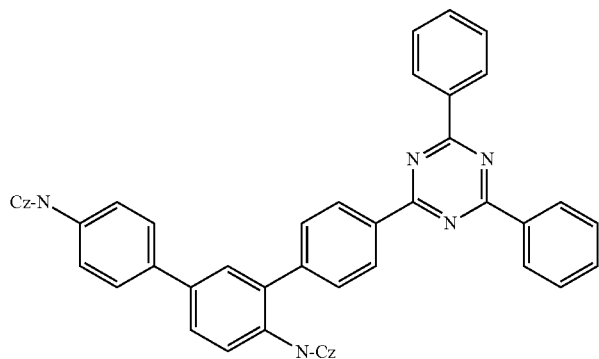
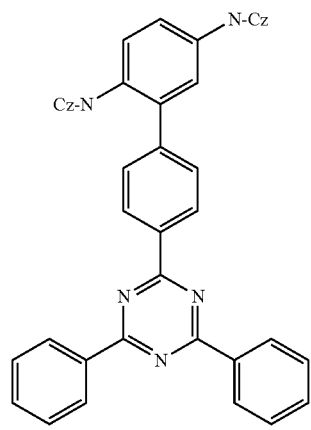
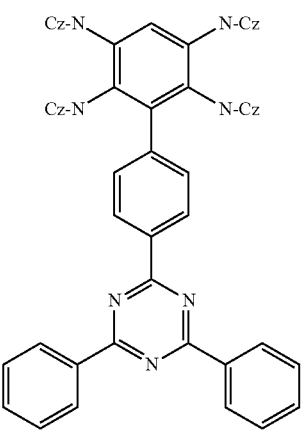
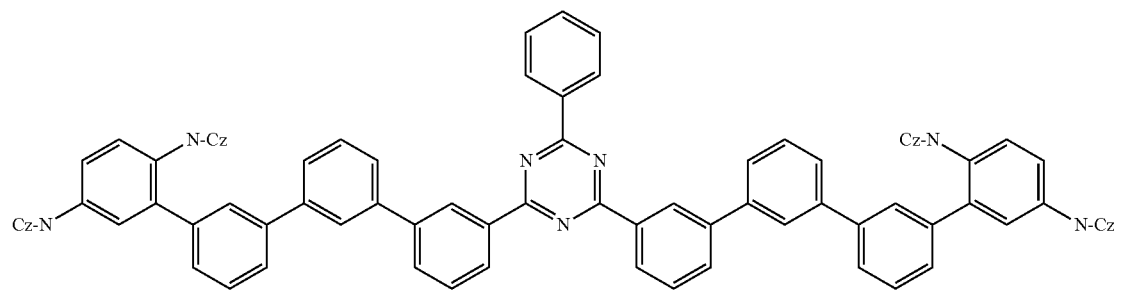
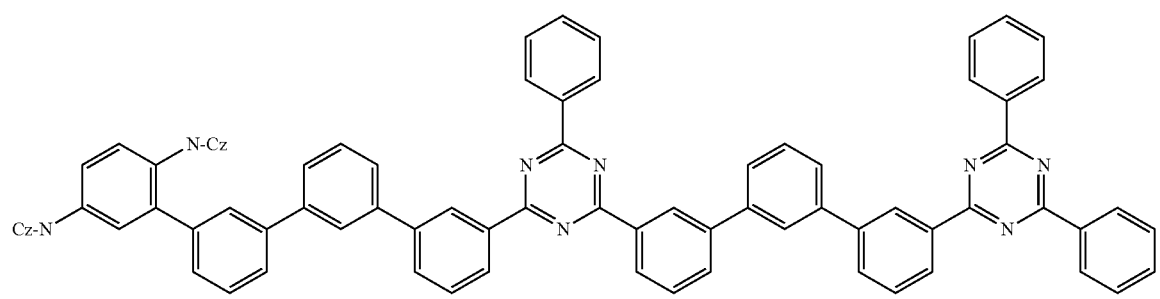

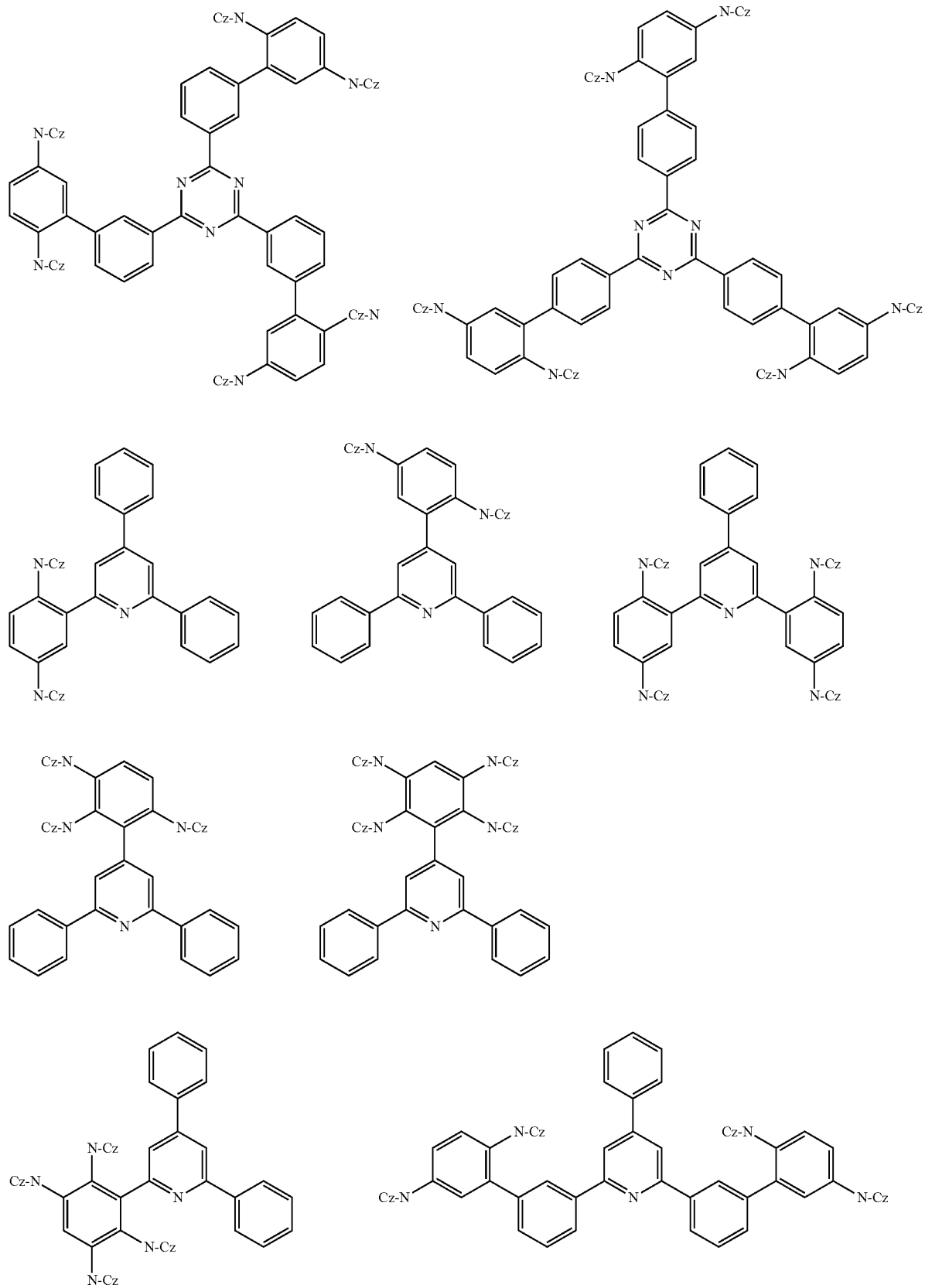

143
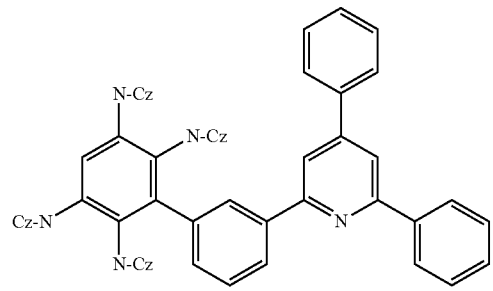
144
-continued
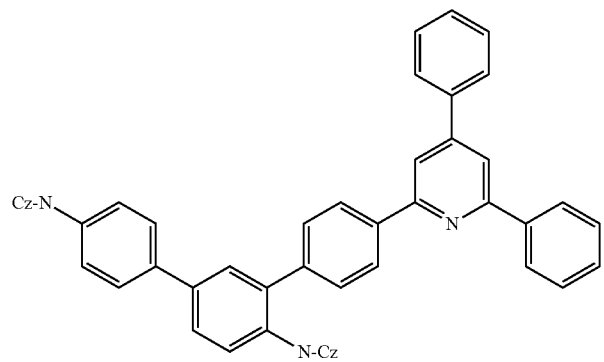
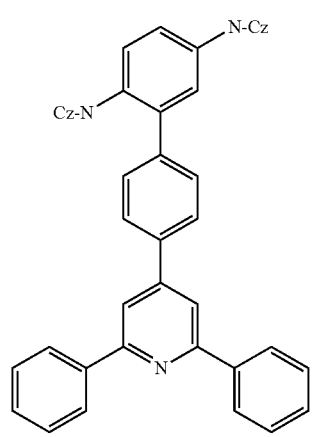
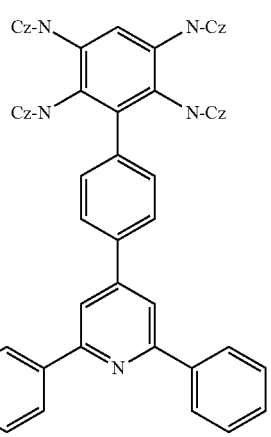
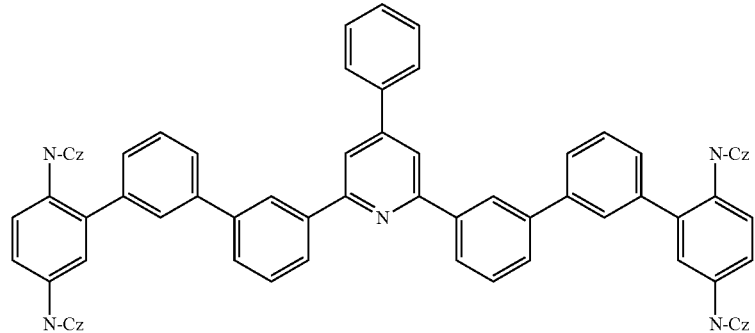
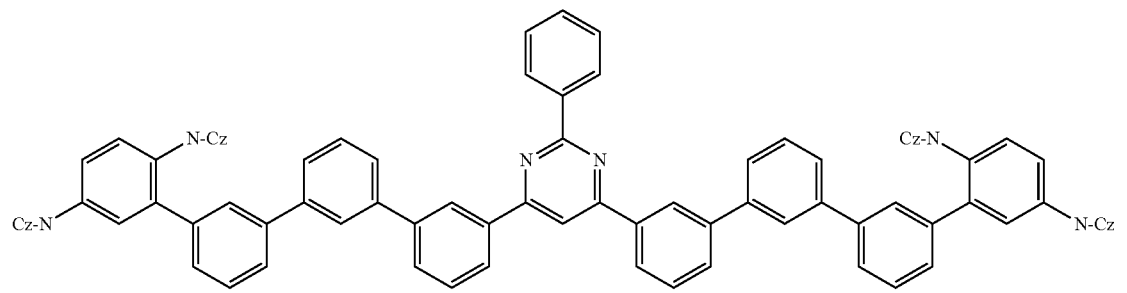
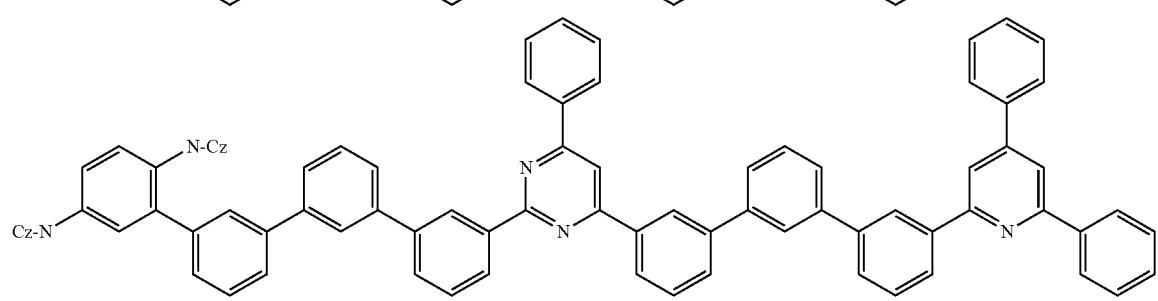

-continued
145
146
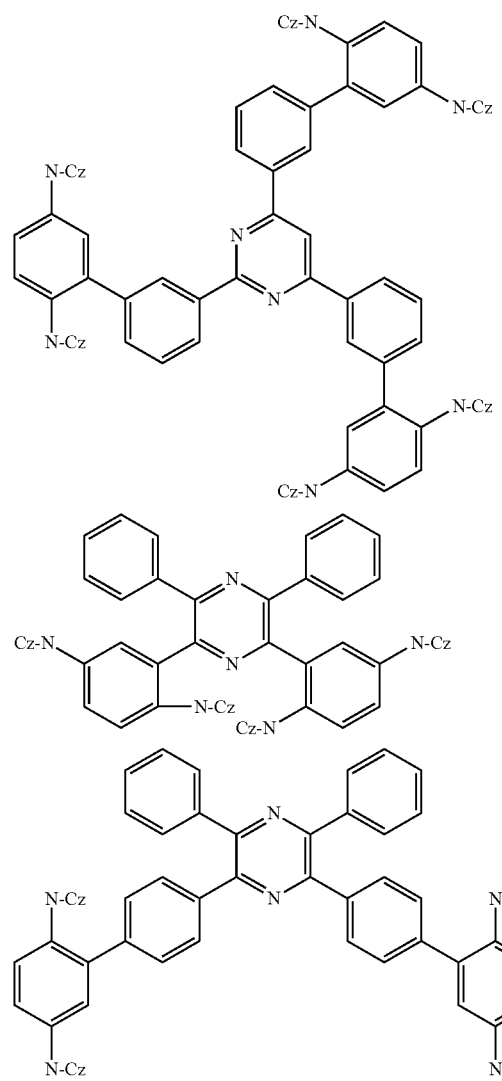
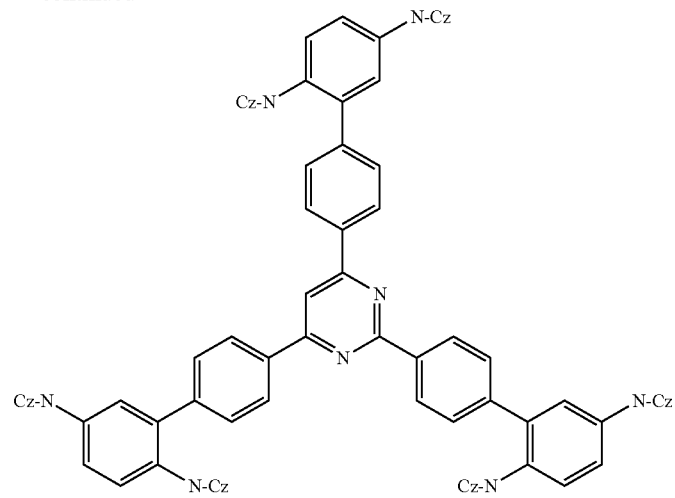
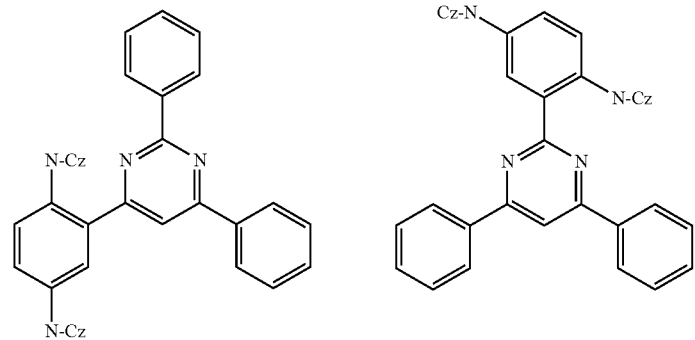
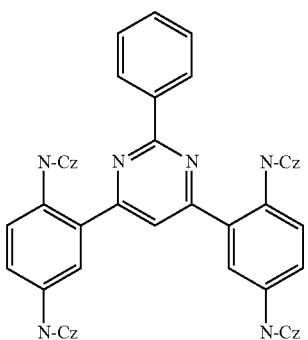
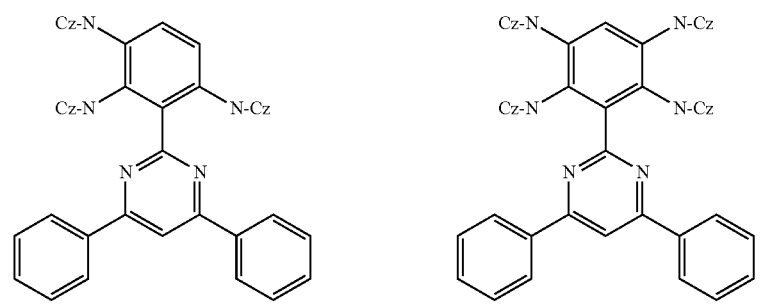

147 148
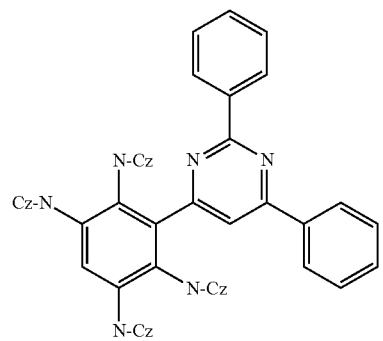
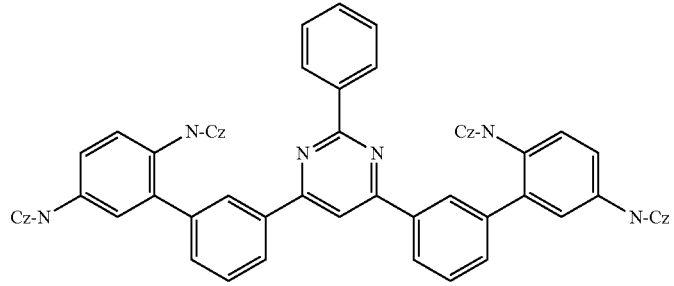
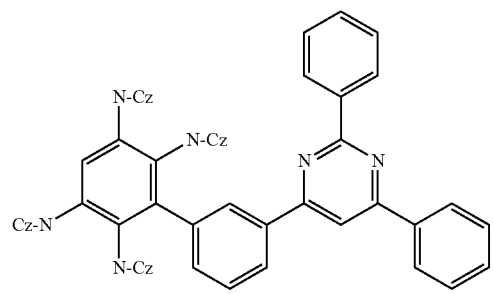
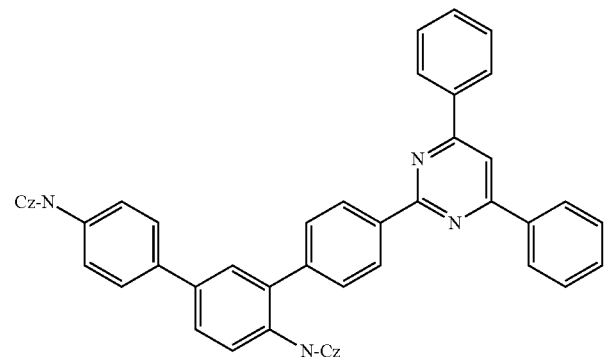
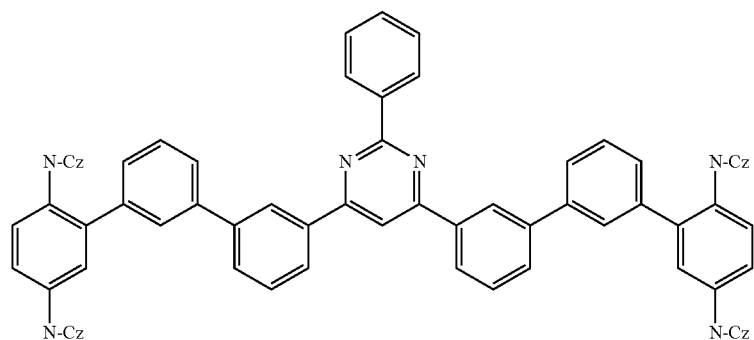
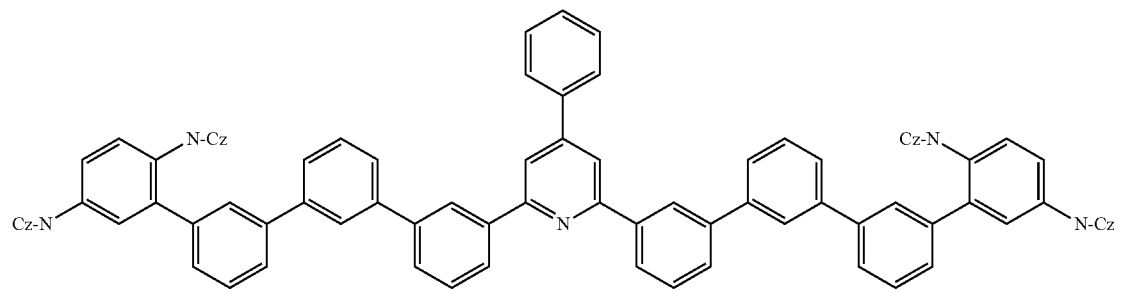
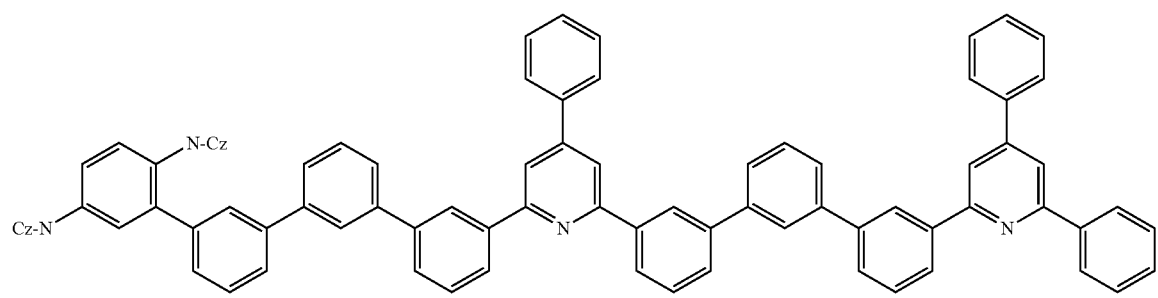

149 150
-continued
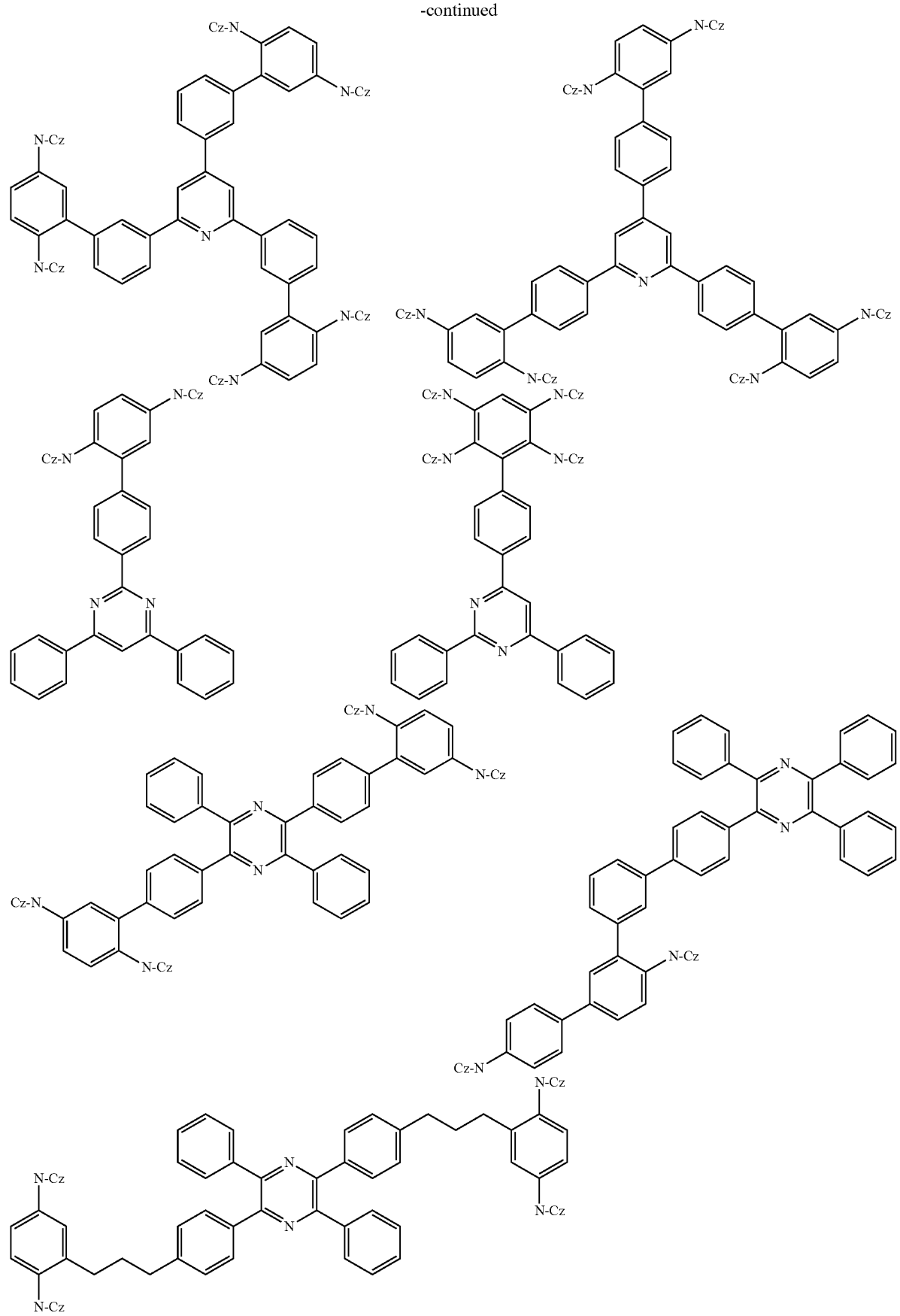

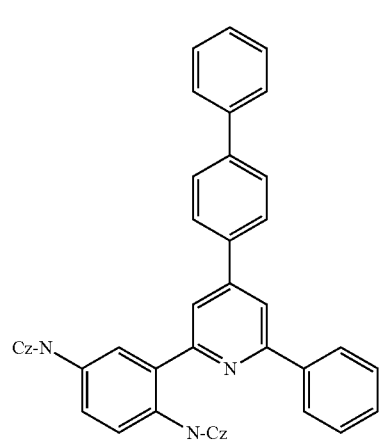
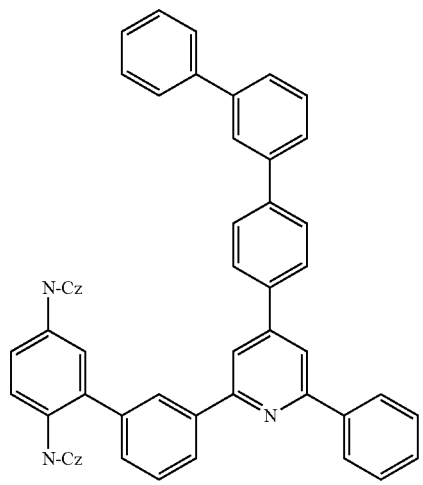
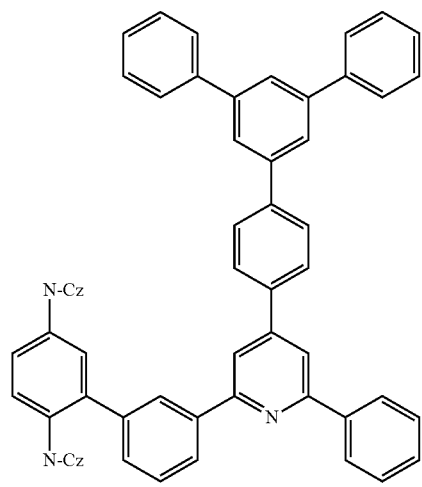
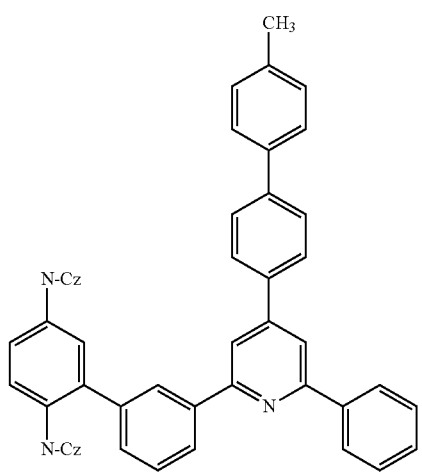
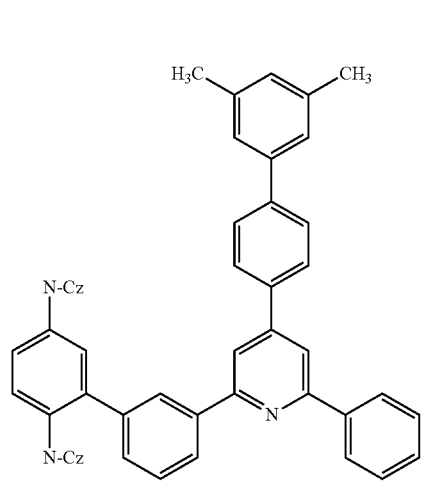
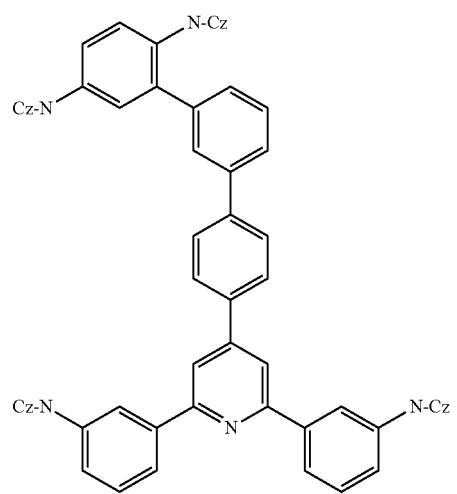

153 154
-continued
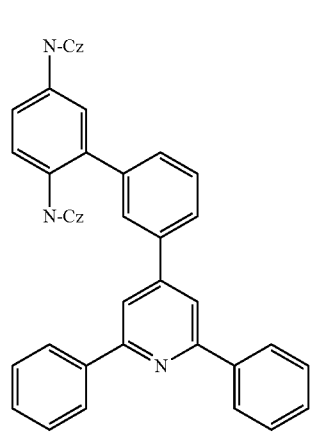
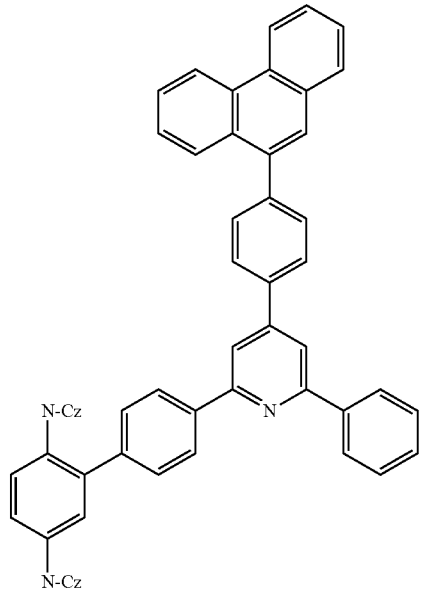
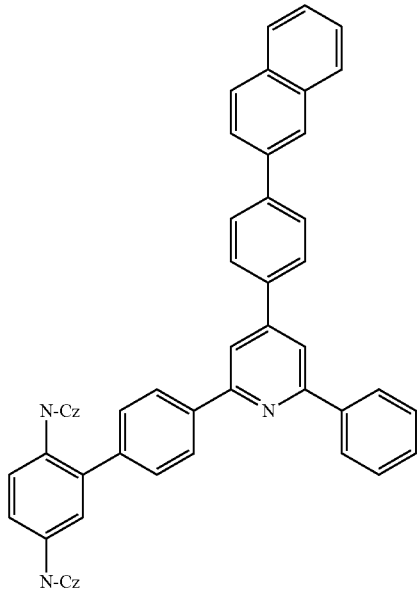
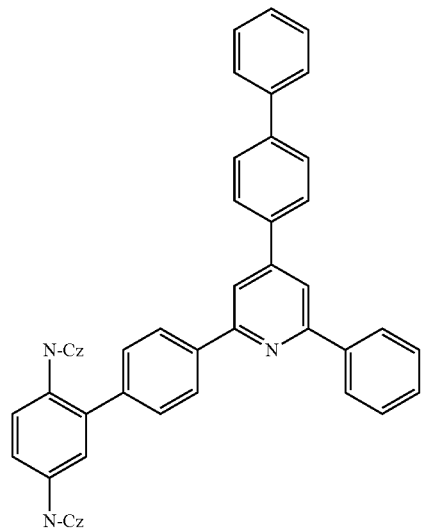
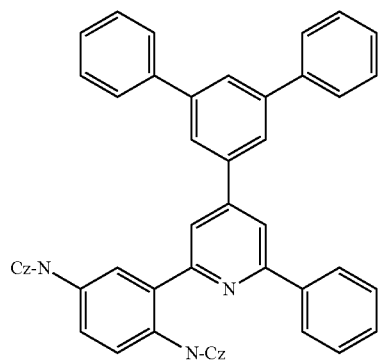
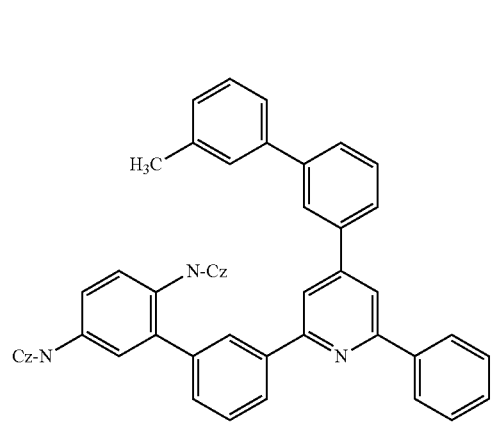
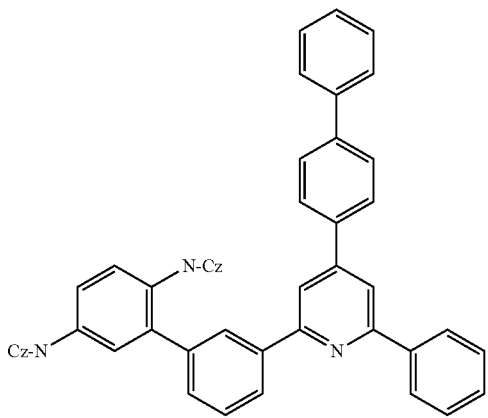

155
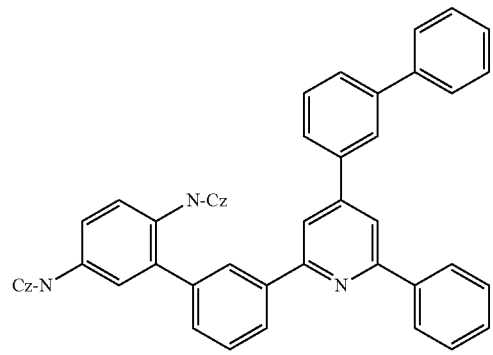
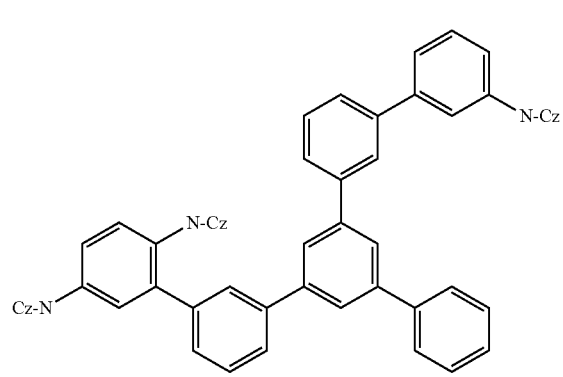
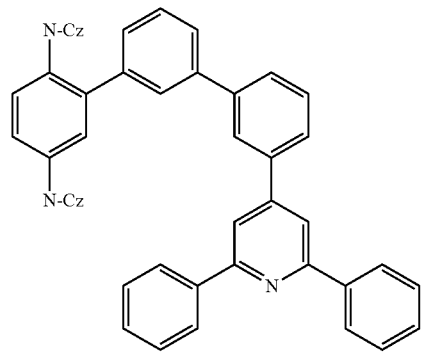
156
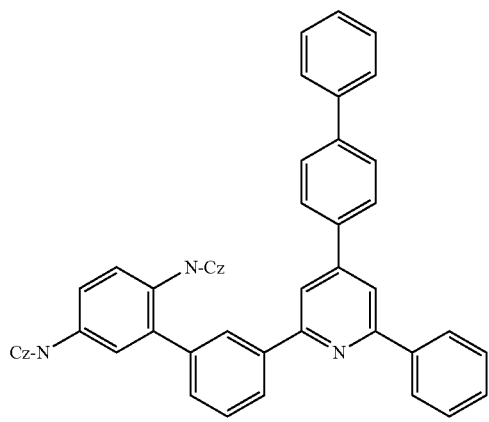
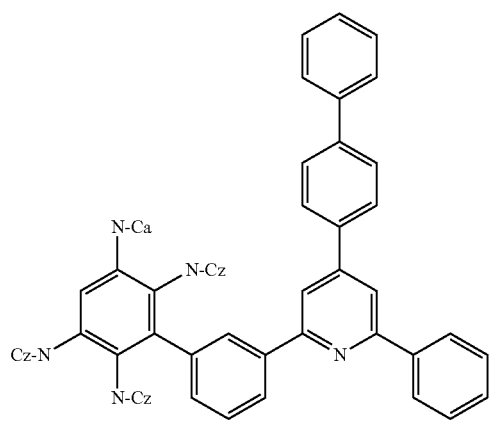
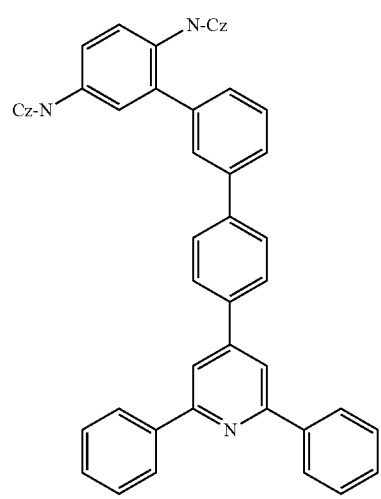

157 158
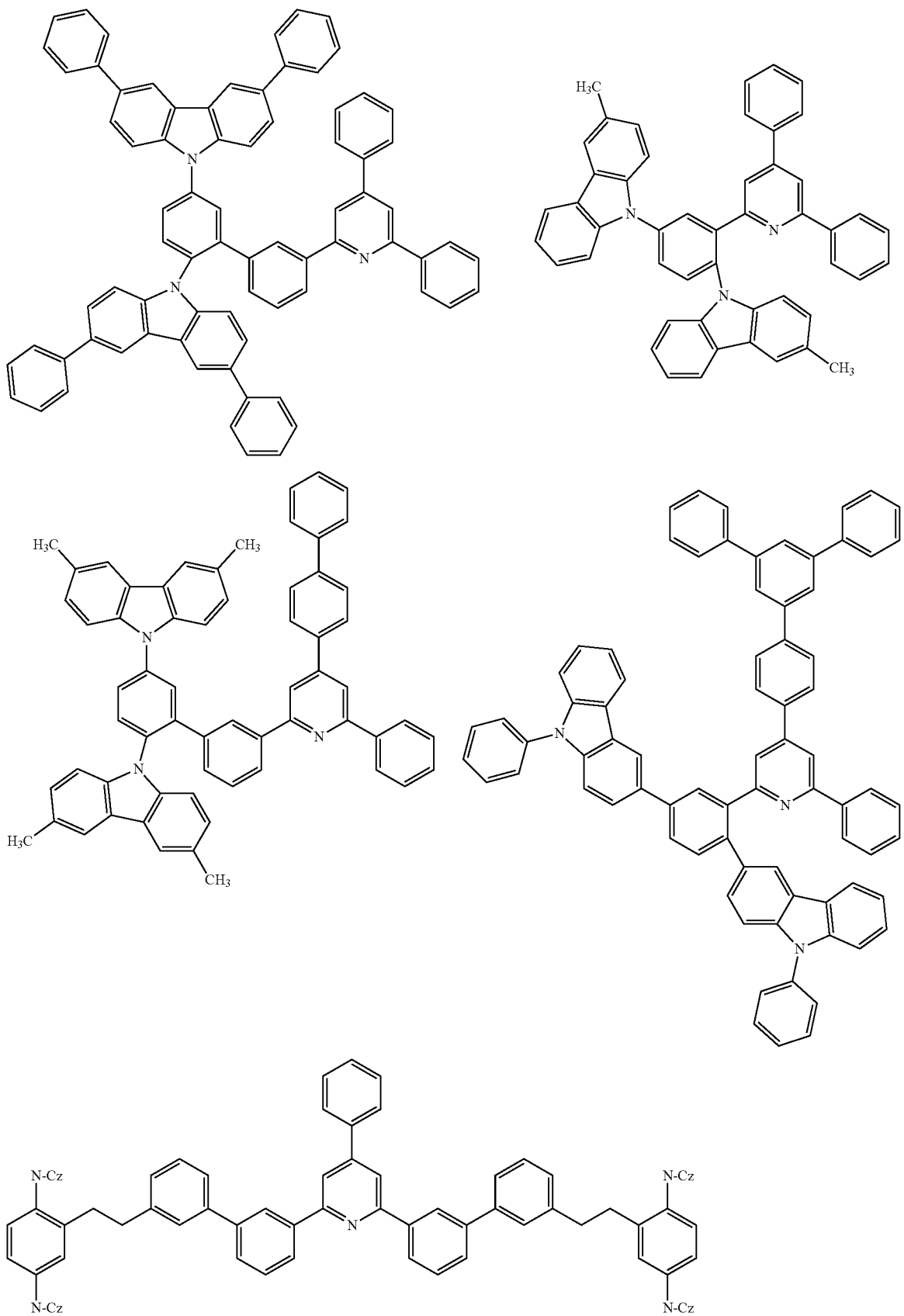
-continued

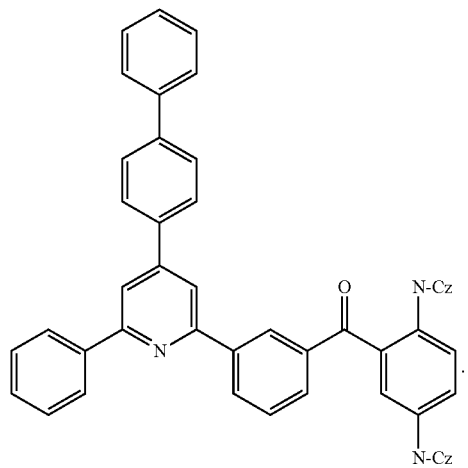

4. An organic compound represented by the following structural formula (EM-1):

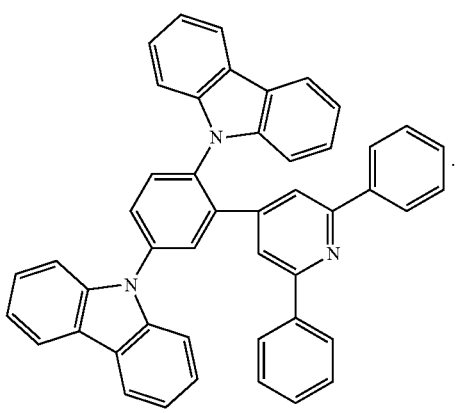

(EM-1)

5. An organic compound represented by the following structural formula (EM-2):

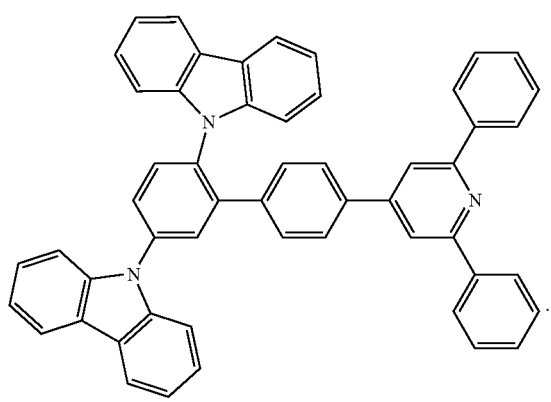

(EM-2)

6. An organic compound represented by the following structural formula (EM-3):

(EM-3)

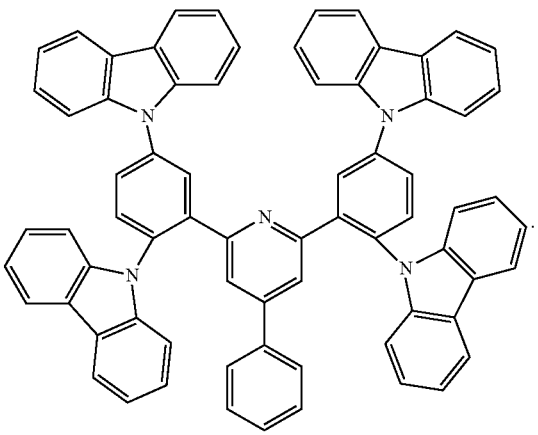

7. An organic compound represented by the following structural formula (EM-4):

(EM-4)

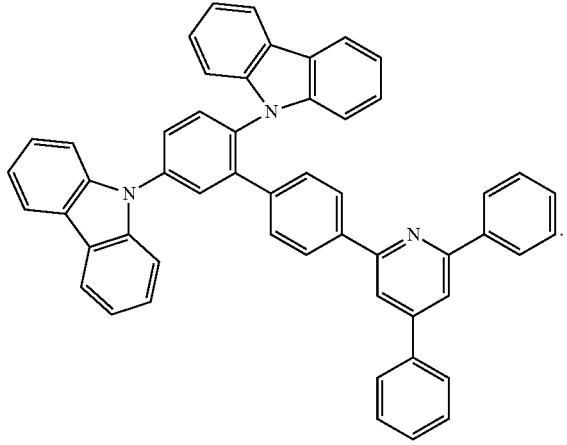

8. An organic compound represented by the following structural formula (EM-5):

(EM-5)

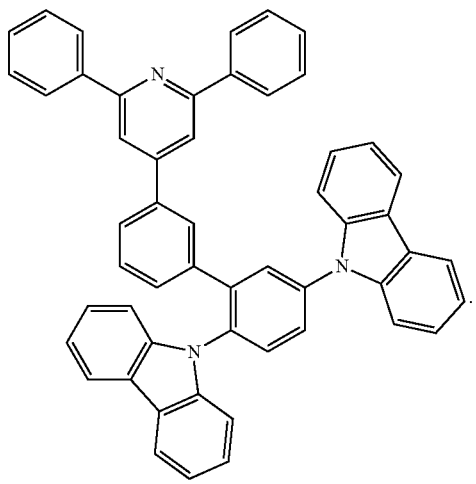

9. An organic compound represented by the following structural formula (EM-6):

(EM-6)

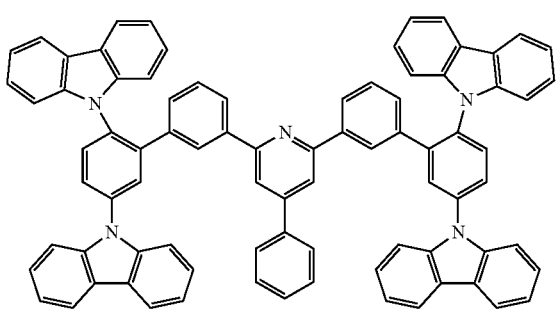

10. An organic compound represented by the following structural formula (EM-7):

(EM-7)

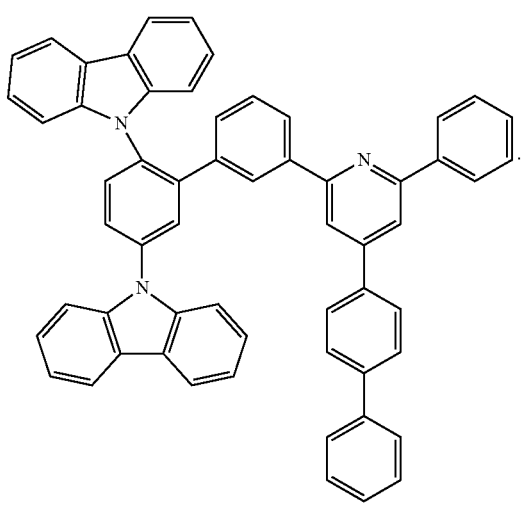

11. An organic compound represented by following Formula (I):

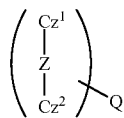

(I)

wherein $Cz^1$ and $Cz^2$ each represent a carbazolyl group;
each of $Cz^1$ and $Cz^2$ may be substituted;
Q represents a direct bond connecting to "G" in following Formula (II):

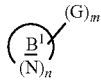

(II)

wherein Ring $B^1$ represents a six-membered aromatic heterocyclic ring having "n" nitrogen atom(s) as hetero atom(s);
"n" represents an integer of from 1 to 3;
Gs connect to carbon atoms at an ortho position and a para position with respect to the nitrogen atom(s) in Ring $B^1$;
G represents a direct bond or an arbitrary linkage group connecting to Q when G connects to Q;
G represents an aromatic hydrocarbon group when G does not connect to Q;
"m" represents an integer of from 3 to 5;
plural Gs in one molecule may be the same as or different from one another; and
Ring $B^1$ may have one or more substituents in addition to Gs,
wherein Z represents a direct bond enabling the conjugation of nitrogen atoms in the carbazole rings of $Cz^1$ and $Cz^2$ with each other.

12. An organic compound represented by following Formula (I):

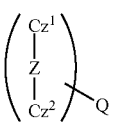

(I)

wherein $Cz^1$ and $Cz^2$ each represent a carbazolyl group;
each of $Cz^1$ and $Cz^2$ may be substituted;
Q represents a direct bond connecting to "G" in following Formula (II):

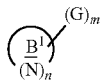

(II)

wherein Ring $B^1$ represents a six-membered aromatic heterocyclic ring having "n" nitrogen atom(s) as hetero atom(s);
"n" represents an integer of from 1 to 3;
Gs connect to carbon atoms at an ortho position and a para position with respect to the nitrogen atom(s) in Ring $B^1$;

G represents a direct bond or an arbitrary linkage group connecting to Q when G connects to Q;

G represents an aromatic hydrocarbon group when G does not connect to Q;

"m" represents an integer of from 3 to 5;

plural Gs in one molecule may be the same as or different from one another; and

Ring $B^1$ may have one or more substituents in addition to Gs, wherein Z represents an aromatic hydrocarbon group enabling the conjugation of nitrogen atoms in the carbazole rings of $Cz^1$ and $Cz^2$ with each other.

13. The organic compound according to claim 12, wherein the aromatic hydrocarbon group represents a bivalent linkage group including one to eight benzene rings bound to each other.

* * * * *

UNITED STATES PATENT AND TRADEMARK OFFICE
CERTIFICATE OF CORRECTION

PATENT NO. : 8,324,403 B2  Page 1 of 1
APPLICATION NO. : 11/722760
DATED : December 4, 2012
INVENTOR(S) : Masayoshi Yabe et al.

It is certified that error appears in the above-identified patent and that said Letters Patent is hereby corrected as shown below:

On the title page, Item (30), the Foreign Application Priority Data is omitted. Item (30) Should read.

--(30)    Foreign Application Priority Data

Dec. 24, 2004   (JP).............................. 2004-373981--

Signed and Sealed this
Twelfth Day of March, 2013

Teresa Stanek Rea
*Acting Director of the United States Patent and Trademark Office*